US012692296B2

(12) United States Patent
Hirano et al.

(10) Patent No.: US 12,692,296 B2
(45) Date of Patent: Jul. 28, 2026

(54) T CELL RECEPTORS AND METHODS OF USE THEREOF

(71) Applicant: University Health Network, Toronto (CA)

(72) Inventors: Naoto Hirano, Toronto (CA); Kenji Murata, Toronto (CA); Kayoko Saso, Toronto (CA)

(73) Assignee: University Health Network, Toronto (CA)

( * ) Notice: Subject to any disclaimer, the term of this patent is extended or adjusted under 35 U.S.C. 154(b) by 1128 days.

(21) Appl. No.: 17/436,931

(22) PCT Filed: Mar. 3, 2020

(86) PCT No.: PCT/IB2020/051808
§ 371 (c)(1),
(2) Date: Sep. 7, 2021

(87) PCT Pub. No.: WO2020/178739
PCT Pub. Date: Sep. 10, 2020

(65) Prior Publication Data
US 2022/0152104 A1     May 19, 2022

Related U.S. Application Data

(60) Provisional application No. 62/813,642, filed on Mar. 4, 2019.

(51) Int. Cl.
| | |
|---|---|
| *C07K 14/725* | (2006.01) |
| *A61K 40/11* | (2025.01) |
| *A61K 40/32* | (2025.01) |
| *A61K 40/42* | (2025.01) |
| *A61K 45/06* | (2006.01) |
| *A61P 35/02* | (2006.01) |
| *A61P 35/04* | (2006.01) |
| *C07K 14/705* | (2006.01) |
| *C07K 14/71* | (2006.01) |
| *C07K 14/74* | (2006.01) |
| *C12N 5/0783* | (2010.01) |
| *C12N 15/113* | (2010.01) |

(52) U.S. Cl.
CPC .......... *C07K 14/7051* (2013.01); *A61K 40/11* (2025.01); *A61K 40/32* (2025.01); *A61K 40/4269* (2025.01); *A61K 45/06* (2013.01); *A61P 35/02* (2018.01); *A61P 35/04* (2018.01); *C07K 14/70539* (2013.01); *C07K 14/71* (2013.01); *C12N 5/0636* (2013.01); *C12N 15/1138* (2013.01); *A61K 2239/48* (2023.05); *C07K 2319/21* (2013.01); *C07K 2319/33* (2013.01); *C12N 2310/14* (2013.01)

(58) Field of Classification Search
CPC .......... C07K 14/7051; C07K 14/70539; C07K 14/71; C07K 2319/21; C07K 2319/33; C07K 2319/00; C07K 2319/03; C07K 16/2809; C07K 16/30; C07K 2317/31; C07K 2317/622; A61K 40/11; A61K 40/32; A61K 40/4269; A61K 45/06; A61K 2239/48; A61K 38/20; A61K 35/17; A61P 35/02; A61P 35/04; A61P 35/00; C12N 5/0636; C12N 15/1138; C12N 2310/14; C12N 2510/00; C12N 2740/13043; C12N 15/62; C12N 9/22; G01N 2333/70539; G01N 33/505; G01N 33/56972
See application file for complete search history.

(56) References Cited

U.S. PATENT DOCUMENTS

| | | | |
|---|---|---|---|
| 2010/0273213 A1 | 10/2010 | Mineno et al. | |
| 2013/0287748 A1 | 10/2013 | June et al. | |
| 2016/0317633 A1 | 11/2016 | Yee et al. | |
| 2022/0152104 A1 | 5/2022 | Hirano et al. | |

(Continued)

FOREIGN PATENT DOCUMENTS

| | | |
|---|---|---|
| CN | 106632660 A | 5/2017 |
| EP | 3118322 A1 | 1/2017 |

(Continued)

OTHER PUBLICATIONS

Okamoto S, et al. A Promising Vector for TCR Gene Therapy: Differential Effect of siRNA, 2A Peptide, and Disulfide Bond on the Introduced TCR Expression. Mol Ther Nucleic Acids. Dec. 18, 2012;1(12):e63. doi: 10.1038/mtna.2012.52. PMID: 23250361; PMCID: PMC3528300. (Year: 2012).*

(Continued)

*Primary Examiner* — Misook Yu
*Assistant Examiner* — Alec Jon Peters
(74) *Attorney, Agent, or Firm* — Sterne, Kessler, Goldstein & Fox P.L.L.C.

(57) ABSTRACT

The present disclosure is directed recombinant T cell receptors capable of binding an NY-ESO-1 epitope and nucleic acid molecules encoding the same. In some embodiments, the nucleic acid molecules further comprise a second nucleotide sequence, wherein the second nucleotide sequence or the polypeptide encoded by the second nucleotide sequence inhibits the expression of an endogenous TCR. Other aspects of the disclosure are directed to vectors comprising the nucleic acid molecule and cells comprising the recombinant TCR, the nucleic acid molecule, or the vector. Still other aspects of the disclosure are directed to methods of using the same. In some embodiments, the methods comprise treating a cancer in a subject in need thereof.

20 Claims, 9 Drawing Sheets
Specification includes a Sequence Listing.

(56) References Cited

U.S. PATENT DOCUMENTS

| | | | |
|---|---|---|---|
| 2022/0152105 A1 | 5/2022 | Hirano et al. | |
| 2022/0168345 A1 | 6/2022 | Hirano et al. | |
| 2022/0168346 A1 | 6/2022 | Hirano et al. | |
| 2022/0168347 A1 | 6/2022 | Hirano et al. | |
| 2022/0169695 A1 | 6/2022 | Hirano et al. | |
| 2022/0169696 A1 | 6/2022 | Hirano et al. | |
| 2022/0324938 A1 | 10/2022 | Hirano et al. | |

FOREIGN PATENT DOCUMENTS

| | | | | |
|---|---|---|---|---|
| KR | 20180135489 A | 12/2018 | | |
| WO | WO-1999045954 A1 | 9/1999 | | |
| WO | WO-2001030382 A1 | 5/2001 | | |
| WO | WO-0226778 A2 | 4/2002 | | |
| WO | WO-2008120202 A2 | 10/2008 | | |
| WO | WO-2010037395 A2 | 4/2010 | | |
| WO | WO-2010112962 A1 | 10/2010 | | |
| WO | WO-2011140284 A2 | 11/2011 | | |
| WO | WO-2012038055 A1 | 3/2012 | | |
| WO | WO-2014207708 A2 * | 12/2014 | ......... | A61K 39/0011 |
| WO | WO-2016073755 A2 | 5/2016 | | |
| WO | WO-2016199140 A1 | 12/2016 | | |
| WO | WO-2017076308 A1 | 5/2017 | | |
| WO | WO-2017120428 A2 | 7/2017 | | |
| WO | WO-2020178739 A1 | 9/2020 | | |

OTHER PUBLICATIONS

Poncette L, et al. Effective NY-ESO-1-specific MHC II-restricted T cell receptors from antigen-negative hosts enhance tumor regression. J Clin Invest. Jan. 2, 2019;129(1):324-335. doi: 10.1172/JCI120391. Epub Dec. 10, 2018. PMID: 30530988; PMCID: PMC6307948. (Year: 2019).*

Wang X., et al. Manufacture of tumor- and virus-specific T lymphocytes for adoptive cell therapies. Cancer Gene Ther. Mar. 2015;22(2):85-94. doi: 10.1038/cgt.2014.81. Epub Feb. 27, 2015. PMID: 25721207; PMCID: PMC4480367. (Year: 2015).*

Thomas, R., et al., "NY-ESO-1 Based Immunotherapy of Cancer: Current Perspectives," Front Immunol 9:947, Frontiers Media S.A., Switzerland (May 2018).

Huang, S., and Kamihira, M., et al., "Development of hybrid viral vectors for gene therapy," Biotechnol Adv. 31(2):208-223, Elsevier, Netherlands (Mar. 2013).

Hirano, N., et al., "Efficient presentation of naturally processed HLA class I peptides by artificial antigen-presenting cells for the generation of effective antitumor responses," Clin. Cancer Res. 12:2967-75, American Association for Cancer Research, United States (May 2006).

Butler, M., and Hirano, N., et al., "Human cell-based artificial antigen-presenting cells for cancer immunotherapy," Immunol. Rev. 257:191-209, Wiley, United States (Jan. 2014).

Kagoya, Y., et al., "DOT1L inhibition attenuates graft-versus-host disease by allogeneic T cells in adoptive immunotherapy models," Nat. Commun. 9:1915, Springer Nature, Germany (May 2018).

Anczurowski, M., et al., "Mechanisms underlying the lack of endogenous processing and CLIP-mediated binding of the invariant chain by HLA-DP 84Gly," Sci. Rep. 8:4804, Springer Nature, Germany (Mar. 2018).

Yamashita, Y., et al., "HLA-DP 84Gly constitutively presents endogenous peptides generated by the class I antigen processing pathway," Nat Commun. 8:15244, Springer Nature, Germany (May 2017).

International Search Report and Written Opinion for International Application No. PCT/IB2020/051808, Canadian Intellectual Property Office, Quebec, mailed on Jun. 30, 2020, 12 pages.

Mojic, M., et al., "The Dark Side of IFN-γ: Its Role in Promoting Cancer Immunoevasion," International Journal of Molecular Sciences 19(1):89, MDPI, Switzerland (Dec. 2017).

Okamoto, S., et al., "Improved expression and reactivity of transduced tumor-specific TCRs in human lymphocytes by specific silencing of endogenous TCR," Cancer Research 69(23):9003-9011, American Association for Cancer Research, United States (Dec. 2009).

Parvizpour, S., et al., "In silico design of a triple-negative breast cancer vaccine by targeting cancer testis antigens," Bioimpacts 9(1):45-56, Tabriz University of Medical Sciences, Iran (Jul. 2019).

Robbins, P.F., et al., "A pilot trial using lymphocytes genetically engineered with an NY-ESO-1-reactive T-cell receptor: long-term follow-up and correlates with response," Clinical Cancer Research 21(5):1019-1027, American Association for Cancer Research, United States (Mar. 2015).

* cited by examiner

Jurkat76/CD8 transduced with

None    B\*40:01/ NY-ESO-1$_{125-133}$ TCR    A\*02:01/ NY-ESO-1$_{157-165}$ TCR (1G4LY)

B\*40:01/ NY-ESO-1$_{125-133}$ multimer

B\*40:01/ HIV nef$_{92-100}$ multimer

B\*40:01/ unexchanged multimer

Multimer

CD8

Transduced with

None $B^*40:01/$ NY-ESO-1$_{125-133}$ TCR $B^*40:01/$ NY-ESO-1$_{125-133}$ multimer $B^*40:01/$ HIV nef$_{92-100}$ multimer

Multimer

CD8

|  |  | B*40:01 | NY-ESO-1 |
|---|---|---|---|
| ☐ | SK-MEL-21 | - | - |
| ▨ | A375 | - | + |
| ☰ | A375/B*40:01 | + | + |
| ■ | SK-MEL-28 | + | - |
| ▨ | SK-MEL-28/NY-ESO-1 | + | + |

SK-MEL-21     A375     SK-MEL-28     SK-MEL-28/NY-ESO-1

NY-ESO-1

1

T CELL RECEPTORS AND METHODS OF USE THEREOF

CROSS REFERENCE TO RELATED APPLICATIONS

This PCT application claims the priority benefit of U.S. Provisional Application No. 62/813,642, filed Mar. 4, 2019, which is incorporated herein by reference in its entirety.

REFERENCE TO SEQUENCE LISTING SUBMITTED ELECTRONICALLY VIA EFS-WEB

The content of the electronically submitted sequence listing (Name: 4285_0020001_Sequencelisting_ST25; Size: 24,350 bytes; Date of Creation: Aug. 5, 2025) is incorporated herein by reference in its entirety.

FIELD OF THE DISCLOSURE

The present disclosure provides recombinant T cell receptors ("TCRs") that specifically bind human NY-ESO-1 and uses thereof.

BACKGROUND OF THE DISCLOSURE

Immunotherapy has immerged as a critical tool in the battle against a variety of diseases, including cancer. T cell therapies are at the forefront of immunotherapeutic development, and adoptive transfer of antitumor T cells has been shown induce clinical responses in cancer patients. Though many T cell therapies target mutated tumor antigens, the vast majority of neoantigens are not shared and are unique to each patient.

Potential non-mutated antigens out number mutated antigens by multiple orders of magnitude. The elucidation of T cell epitopes derived from shared antigens may facilitate the robust development of efficacious and safe adoptive T cell therapies that are readily available to a larger cohort of cancer patients. However, the sheer number of non-mutated antigens and the high polymorphism of HLA genes may have hampered comprehensive analyses of the specificity of antitumor T cell responses toward non-mutated antigens.

The present disclosure provides novel epitopes for the non-mutated antigen NY-ESO-1 and TCRs capable of specifically binding the epitopes. These novel epitopes are associated with associated with particular HLA alleles. The use of these tumor-reactive HLA-restricted NY-ESO-1 TCRs stand to widen the applicability of anti-NY-ESO-1 TCR gene therapy, particularly in immuno-oncology.

SUMMARY OF THE DISCLOSURE

Certain aspects of the present disclosure are directed to a nucleic acid molecule comprising (i) a first nucleotide sequence encoding a recombinant T cell receptor (TCR) or an antigen binding portion thereof that specifically binds human NY-ESO-1 ("anti-NY-ESO-1 TCR"); and (ii) a second nucleotide sequence, wherein the second nucleotide sequence or the polypeptide encoded by the second nucleotide sequence inhibits the expression of an endogenous TCR, wherein the anti-NY-ESO-1 TCR cross competes for binding to human NY-ESO-1 with a reference TCR, which comprises an alpha chain and a beta chain, and wherein the alpha chain comprises an amino acid sequence as set forth in SEQ ID NO: 1 and the beta chain comprises an amino acid sequence as set forth in SEQ ID NO: 2.

Certain aspects of the present disclosure are directed to a nucleic acid molecule comprising (i) a first nucleotide sequence encoding a recombinant T cell receptor (TCR) or an antigen binding portion thereof that specifically binds human NY-ESO-1 ("anti-NY-ESO-1 TCR"); and (ii) a second nucleotide sequence, wherein the second nucleotide sequence or the polypeptide encoded by the second nucleotide sequence inhibits the expression of an endogenous TCR, wherein the anti-NY-ESO-1 TCR binds the same epitope or an overlapping epitope of human NY-ESO-1 as a reference TCR, which comprises an alpha chain and a beta chain, wherein the alpha chain comprises an amino acid sequence as set forth in SEQ ID NO: 1 and the beta chain comprises an amino acid sequence as set forth in SEQ ID NO: 2.

In some embodiments, the anti-NY-ESO-1 TCR binds to an epitope of NY-ESO-1 consisting of an amino acid sequence as set forth in SEQ ID NO: 13. In some embodiments, the epitope is complexed with an HLA class I molecule. In some embodiments, the HLA class I molecule is an HLA-B*40 allele. In some embodiments, the HLA class I molecule is selected from an HLA-B*40:01 allele, an HLA-B*40:02 allele, an HLA-B*40:03 allele, an HLA-B*40:04 allele, an HLA-B*40:05 allele, and an HLA-B*40:06 allele. In some embodiments, the HLA class I molecule is an HLA-B*40:01 allele.

In some embodiments, the anti-NY-ESO-1 TCR comprises an alpha chain and a beta chain, wherein the alpha chain comprises a variable region comprising an alpha chain CDR1, an alpha chain CDR2, and an alpha chain CDR3; and wherein the beta chain comprises variable domain comprising a beta chain CDR1, a beta chain CDR2, and a beta chain CDR3; wherein the alpha chain CDR3 comprises an amino acid sequence as set forth in SEQ ID NO: 7. In some embodiments, the beta chain CDR3 of the anti-NY-ESO-1 TCR comprises an amino acid sequence as set forth in SEQ ID NO: 10.

In some embodiments, the anti-NY-ESO-1 TCR comprises an alpha chain and a beta chain, wherein the alpha chain comprises a variable region comprising an alpha chain CDR1, an alpha chain CDR2, and an alpha chain CDR3; and wherein the beta chain comprises variable domain comprising a beta chain CDR1, a beta chain CDR2, and a beta chain CDR3; wherein the beta chain CDR3 of the anti-NY-ESO-1 TCR comprises an amino acid sequence as set forth in SEQ ID NO: 10. In some embodiments, the alpha chain CDR3 of the anti-NY-ESO-1 TCR comprises an amino acid sequence as set forth in SEQ ID NO: 7.

In some embodiments, the alpha chain CDR1 of the anti-NY-ESO-1 TCR comprises an amino acid sequence as set forth in SEQ ID NO: 5. In some embodiments, the beta chain CDR1 of the anti-NY-ESO-1 TCR comprises an amino acid sequence as set forth in SEQ ID NO: 8. In some embodiments, the alpha chain CDR2 of the anti-NY-ESO-1 TCR comprises an amino acid sequence as set forth in SEQ ID NO: 6. In some embodiments, the beta chain CDR2 of the anti-NY-ESO-1 TCR comprises an amino acid sequence as set forth in SEQ ID NO: 9.

In some embodiments, the alpha chain variable domain of the anti-NY-ESO-1 TCR comprises an amino acid sequence of a variable domain present in the amino acid sequence set forth SEQ ID NO: 1. In some embodiments, the beta chain variable domain of the anti-NY-ESO-1 TCR comprises an amino acid sequence of a variable domain present in the amino acid sequence set forth SEQ ID NO: 2.

In some embodiments, the alpha chain of the anti-NY-ESO-1 TCR further comprises a constant region, wherein the constant region is different from endogenous constant region of the alpha chain. In some embodiments, the alpha chain of the anti-NY-ESO-1 TCR further comprises a constant region, wherein the alpha chain constant region comprises an amino acid sequence having at least about 85%, at least about 90%, at least about 95%, at least about 96%, at least about 97%, at least about 98%, or at least about 99% sequence identity to a constant region present in the amino acid sequence set forth SEQ ID NO: 1. In some embodiments, the alpha chain constant region comprises an amino acid sequence comprising at least 1, at least 2, at least 3, at least 4, or at least 5 amino acid substitutions relative to a constant region present in the amino acid sequence set forth SEQ ID NO: 1. In some embodiments, the beta chain of the anti-NY-ESO-1 TCR further comprises a constant region, wherein the constant region is different from endogenous constant regions of the beta chain.

In some embodiments, the beta chain of the anti-NY-ESO-1 TCR further comprises a constant region, wherein the beta chain constant region comprises an amino acid sequence having at least about 85%, at least about 90%, at least about 95%, at least about 96%, at least about 97%, at least about 98%, or at least about 99% sequence identity to a constant region present in the amino acid sequence set forth SEQ ID NO: 2. In some embodiments, the beta chain constant region comprises an amino acid sequence comprising at least 1, at least 2, at least 3, at least 4, or at least 5 amino acid substitutions relative to a constant region present in the amino acid sequence set forth SEQ ID NO: 2. In some embodiments, the alpha chain of the anti-NY-ESO-1 TCR comprises an amino acid sequence as set forth in SEQ ID NO: 1.

In some embodiments, the beta chain of the anti-NY-ESO-1 TCR comprises an amino acid sequence as set forth in SEQ ID NO: 2. In some embodiments, the second nucleotide sequence is one or more siRNAs that reduce the expression of endogenous TCRs.

In some embodiments, the one or more siRNAs are complementary to a target sequence within a nucleotide sequence encoding a constant region of the endogenous TCRs. In some embodiments, the one or more siRNAs comprise one or more nucleotide sequences selected from the group consisting of SEQ ID NOs: 53-56.

In some embodiments, the second nucleotide sequence encodes Cas9.

In some embodiments, the anti-NY-ESO-1 TCR comprises an alpha chain constant region, a beta chain constant region, or both; and wherein the alpha chain constant region, the beta chain constant region, or both comprises an amino acid sequence having at least 1, at least 2, at least 3, at least 4, or at least 5 substitutions within the target sequence relative to the corresponding amino acid sequence of an endogenous TCR.

Certain aspects of the present disclosure are directed to a vector comprising a nucleic acid molecule disclosed herein. In some embodiments, the vector is a viral vector, a mammalian vector, or bacterial vector. In some embodiments, the vector is a retroviral vector. In some embodiments, the vector is selected from the group consisting of an adenoviral vector, a lentivirus, a Sendai virus vector, a baculoviral vector, an Epstein Barr viral vector, a papovaviral vector, a vaccinia viral vector, a herpes simplex viral vector, a hybrid vector, and an adeno associated virus (AAV) vector. In some embodiments, the vector is a lentivirus.

Certain aspects of the present disclosure are directed to a T cell receptor (TCR) or an antigen binding portion thereof comprising an alpha chain variable domain of the anti-NY-ESO-1 TCR disclosed herein and a beta chain variable domain of the anti-NY-ESO-1 TCR disclosed herein. In some embodiments, the recombinant T cell receptor (TCR) or an antigen binding portion thereof that specifically binds human NY-ESO-1 ("an anti-NY-ESO-1 TCR"), which cross competes for binding to human NY-ESO-1 with a reference TCR; wherein the reference TCR comprises an alpha chain and a beta chain, and wherein the alpha chain comprises an amino acid sequence as set forth in SEQ ID NO: 1 and the beta chain comprises an amino acid sequence as set forth in SEQ ID NO: 2; and wherein the anti-NY-ESO-1 TCR comprises an alpha chain and a beta chain, wherein the alpha chain comprises a constant region, and wherein the beta chain comprises a constant region; wherein (i) the alpha chain constant region comprises an amino acid sequence having a least 1, at least 2, at least 3, at least 4, or at least 5 amino acid substitutions relative to a constant region present in the amino acid sequence set forth in SEQ ID NO: 1 or (ii) the beta chain constant region comprises an amino acid sequence having a least 1, at least 2, at least 3, at least 4, or at least 5 amino acid substitutions relative to a constant region present in the amino acid sequence of SEQ ID NO: 2.

Certain aspects of the present disclosure are directed to a recombinant T cell receptor (TCR) or an antigen binding portion thereof that specifically binds human NY-ESO-1 ("an anti-NY-ESO-1 TCR"), which binds the same epitope or an overlapping epitope of human NY-ESO-1 as a reference TCR; wherein the reference TCR comprises an alpha chain and a beta chain, and wherein the alpha chain comprises an amino acid sequence as set forth in SEQ ID NO: 1 and the beta chain comprises an amino acid sequence as set forth in SEQ ID NO: 2; and wherein the anti-NY-ESO-1 TCR comprises an alpha chain and a beta chain, wherein the alpha chain comprises a constant region, and wherein the beta chain comprises a constant region; wherein (i) the alpha chain constant region comprises an amino acid sequence having a least 1, at least 2, at least 3, at least 4, or at least 5 amino acid substitutions relative to a constant region present in the amino acid sequence set forth in SEQ ID NO: 1 or (ii) the beta chain constant region comprises an amino acid sequence having a least 1, at least 2, at least 3, at least 4, or at least 5 amino acid substitutions relative to a constant region present in the amino acid sequence set forth in SEQ ID NO: 2. In some embodiments, the anti-NY-ESO-1 TCR binds to an epitope of NY-ESO-1 consisting of an amino acid sequence as set forth in SEQ ID NO: 13.

In some embodiments, the epitope is complexed with an HLA class I molecule. In some embodiments, the HLA class I molecule is an HLA-A, HLA-B, HLA-C, HLA-E, HLA-F, or HLA-G allele. In some embodiments, the HLA class I molecule is an HLA-B*40 allele. In some embodiments, the HLA class I molecule is selected from an HLA-B*40:01 allele, an HLA-B*40:02 allele, an HLA-B*40:03 allele, an HLA-B*40:04 allele, an HLA-B*40:05 allele, and an HLA-B*40:06 allele. In some embodiments, the HLA class I molecule is an HLA-B*40:01 allele.

In some embodiments, the alpha chain of the anti-NY-ESO-1 TCR comprises a variable domain comprising an alpha chain CDR1, an alpha chain CDR2, and an alpha chain CDR3; and wherein the beta chain of the anti-NY-ESO-1 TCR comprises variable domain comprising a beta chain CDR1, a beta chain CDR2, and a beta chain CDR3; wherein the alpha chain CDR3 of the anti-NY-ESO-1 comprises an amino acid sequence as set forth in SEQ ID NO: 7. In some embodiments, the beta chain CDR3 of the anti-NY-ESO-1 TCR comprises an amino acid sequence as set forth in SEQ ID NO: 10.

In some embodiments, the alpha chain of the anti-NY-ESO-1 TCR comprises a variable domain comprising an alpha chainCDR1, an alpha chain CDR2, and an alpha chain CDR3; and wherein the beta chain of the anti-NY-ESO-1 TCR comprises a variable domain comprising a beta chain CDR1, a beta chain CDR2, and a beta chain CDR3; wherein the beta chain CDR3 of the anti-NY-ESO-1 TCR comprises an amino acid sequence as set forth in SEQ ID NO: 10. In some embodiments, the alpha chain CDR3 of the anti-NY-ESO-1 TCR comprises an amino acid sequence as set forth in SEQ ID NO: 7.

In some embodiments, the alpha chain CDR1 of the anti-NY-ESO-1 TCR comprises an amino acid sequence as set forth in SEQ ID NO: 5. In some embodiments, the beta chain CDR1 of the anti-NY-ESO-1 TCR comprises an amino acid sequence as set forth in SEQ ID NO: 8. In some embodiments, the alpha chain CDR2 of the anti-NY-ESO-1 TCR comprises an amino acid sequence as set forth in SEQ ID NO: 6. In some embodiments, the beta chain CDR2 of the anti-NY-ESO-1 TCR comprises an amino acid sequence as set forth in SEQ ID NO: 9.

In some embodiments, the alpha chain variable domain of the anti-NY-ESO-1 TCR comprises an amino acid sequence of a variable domain present in the amino acid sequence set forth in SEQ ID NO: 1. In some embodiments, the beta chain variable domain of the anti-NY-ESO-1 TCR comprises an amino acid sequence of a variable domain present in the amino acid sequence set forth in SEQ ID NO: 2.

In some embodiments, the alpha chain constant region comprises an amino acid sequence having at least about 85%, at least about 90%, at least about 95%, at least about 96%, at least about 97%, at least about 98%, or at least about 99% sequence identity to the amino acid sequence of a constant region present in the amino acid sequence set forth in SEQ ID NO: 1.

In some embodiments, the beta chain constant region comprises an amino acid sequence having at least about 85%, at least about 90%, at least about 95%, at least about 96%, at least about 97%, at least about 98%, or at least about 99% sequence identity to the amino acid sequence of a constant region present in the amino acid sequence set forth in SEQ ID NO: 2.

In some embodiments, the alpha chain of the anti-NY-ESO-1 TCR comprises an amino acid sequence as set forth in SEQ ID NO: 1. In some embodiments, the beta chain of the anti-NY-ESO-1 TCR comprises an amino acid sequence as set forth in SEQ ID NO: 2.

Certain aspects of the present disclosure are directed to a bispecific TCR comprising a first antigen-binding domain and a second antigen-binding domain, wherein the first antigen-binding domain comprises a TCR or an antigen-binding portion thereof disclosed herein or a TCR or an antigen-binding portion thereof disclosed herein. In some embodiments, the first antigen-binding domain comprises a single chain variable fragment ("scFv"). In some embodiments, the second antigen-binding domain binds specifically to a protein expressed on the surface of a T cell. In some embodiments, the second antigen-binding domain binds specifically to CD3. In some embodiments, the second antigen-binding domain comprises an scFv. In some embodiments, the first antigen-binding domain and the second antigen-binding domain are linked or associated by a covalent bond. In some embodiments, the first antigen-binding domain and the second antigen-binding domain are linked by a peptide bond.

Certain aspects of the present disclosure are directed to a cell comprising a nucleic acid molecule disclosed herein, a vector disclosed herein, a TCR disclosed herein, a recombinant TCR disclosed herein, or a bispecific TCR disclosed herein. In some embodiments, the cell further expresses CD3. In some embodiments, the cell is selected from the group consisting of a T cell, a natural killer (NK) cell, an natural killer T (NKT) cell, or an ILC cell.

Certain aspects of the present disclosure are directed to a method of treating a cancer in a subject in need thereof, comprising administering to the subject a cell disclosed herein. In some embodiments, the cancer is selected from the group consisting of melanoma, bone cancer, pancreatic cancer, skin cancer, cancer of the head or neck, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, other B cell malignancies, and combinations of said cancers.

In some embodiments, the cancer is relapsed or refractory. In some embodiments, the cancer is locally advanced. In some embodiments, the cancer is advanced. In some embodiments, the cancer is metastatic.

In some embodiments, the cells are obtained from the subject. In some embodiments, the cells are obtained from a donor other than the subject. In some embodiments, the subject is preconditioned prior to the administering of the cells. In some embodiments, the preconditioning comprises administering to the subject a chemotherapy, a cytokine, a protein, a small molecule, or any combination thereof. In some embodiments, the preconditioning comprises administering an interleukin. In some embodiments, the preconditioning comprises administering IL-2, IL-4, IL-7, IL-9, IL-15, IL-21, or any combination thereof. In some embodiments, the preconditioning comprises administering a preconditioning agent selected from the group consisting of cyclophosphamide, fludarabine, vitamin C, an AKT inhibitor, ATRA, Rapamycin, or any combination thereof. In some embodiments, the preconditioning comprises administering cyclophosphamide, fludarabine, or both.

Certain aspects of the present disclosure are directed to a method of engineering an antigen-targeting cell, comprising transducing a cell collected from a subject in need of a T cell therapy with a nucleic acid disclosed herein or a vector disclosed herein. In some embodiments, the antigen-targeting cell further expresses CD3. In some embodiments, the cell is a T cell or a natural killer (NK) cell.

Certain aspects of the present disclosure are directed to an HLA class I molecule complexed to a peptide, wherein the HLA class I molecule comprises an a1 domain, an a2 domain, an a3 domain and a B2m, and wherein the peptide consists of an amino acid sequence as set forth in SEQ ID NO: 14.

In some embodiments, the HLA class I molecule is an HLA-A, HLA-B, HLA-C, HLA-E, HLA-F, or HLA-G. In some embodiments, the HLA class I molecule an HLA-B. In some embodiments, the HLA class I molecule is an HLA-B*40 allele. In some embodiments, the HLA class I molecule is selected from an HLA-B*40:01 allele, HLA-B*40:02 allele, an HLA-B*40:03 allele, an HLA-B*40:04 allele, an HLA-B*40:05 allele, and an HLA-B*40:06 allele. In some embodiments, the HLA class I molecule is an HLA-B*40:01 allele. In some embodiments, the HLA class I molecule is an HLA-B*40:02 allele.

In some embodiments, the HLA class I molecule is a monomer. In some embodiments, the HLA class I molecule is a dimer. In some embodiments, the HLA class I molecule is a trimer. In some embodiments, the HLA class I molecule is a tetramer. In some embodiments, the HLA class I molecule is a pentamer.

Certain aspects of the present disclosure are directed to an antigen presenting cell (APC), comprising an HLA class I molecule disclosed herein. In some embodiments, the HLA class I molecule is expressed on the surface of the APC.

Certain aspects of the present disclosure are directed to a method of enriching a target population of T cells obtained from a human subject, comprising contacting the T cells with an HLA class I molecule disclosed herein or an APC disclosed herein, wherein following the contacting, the enriched population of T cells comprises a higher number of T cells capable of binding the HLA class I molecule relative to the number of T cells capable of binding the HLA class I molecule prior to the contacting.

Certain aspects of the present disclosure are directed to a method of enriching a target population of T cells obtained from a human subject, comprising contacting the T cells in vitro with a peptide, wherein the peptide consists of an amino acid sequence as set forth in SEQ ID NO: 13, wherein following the contacting, the enriched population of T cells comprises a higher number of T cells capable of targeting a tumor cell relative to the number of T cells capable of targeting a tumor cell prior to the contacting.

In some embodiments, the T cells obtained from the human subject are tumor infiltrating lymphocyte (TIL).

Certain aspects of the present disclosure are directed to a method of treating a tumor in a subject in need thereof, comprising administering to the subject an enriched population of T cells disclosed herein.

Certain aspects of the present disclosure are directed to a method of enhancing cytotoxic T cell-mediated targeting of cancer cells in a subject afflicted with a cancer, comprising administering to the subject a peptide having an amino acid sequence as set forth in SEQ ID NO: 13.

Certain aspects of the present disclosure are directed to a cancer vaccine comprising a peptide having an amino acid sequence as set forth in SEQ ID NO: 13.

Certain aspects of the present disclosure are directed to a method of selecting a T cell capable of targeting a tumor cell, comprising contacting a population of isolated T cells in vitro with a peptide, wherein the peptide consists of an amino acid sequence as set forth in SEQ ID NO: 11. In some embodiments, the T cell is a tumor infiltrating lymphocyte (TIL).

BRIEF DESCRIPTION OF THE DRAWINGS

FIGS. 2A and 2C) and 14 days after stimulation (day 14; FIGS. 2B and 2D) are shown. The percentage of multimer cells in CD8 T cells is shown.

(FIGS. 4D, 4E, and 4F), B*40:01/unexchanged multimer (FIGS. 4G, 4H, and 4I), and A*02:01/NY-ESO-1$_{157-165}$ TCR (clone 1G4LY; FIGS. 4C, 4F, and 4I) as well as untransduced Jurkat 76/CD8 cells (FIGS. 4A, 4D, and 4G) were employed as controls The percentage of multimer CD8 cells is shown.

DETAILED DESCRIPTION OF THE DISCLOSURE

Figure 1:
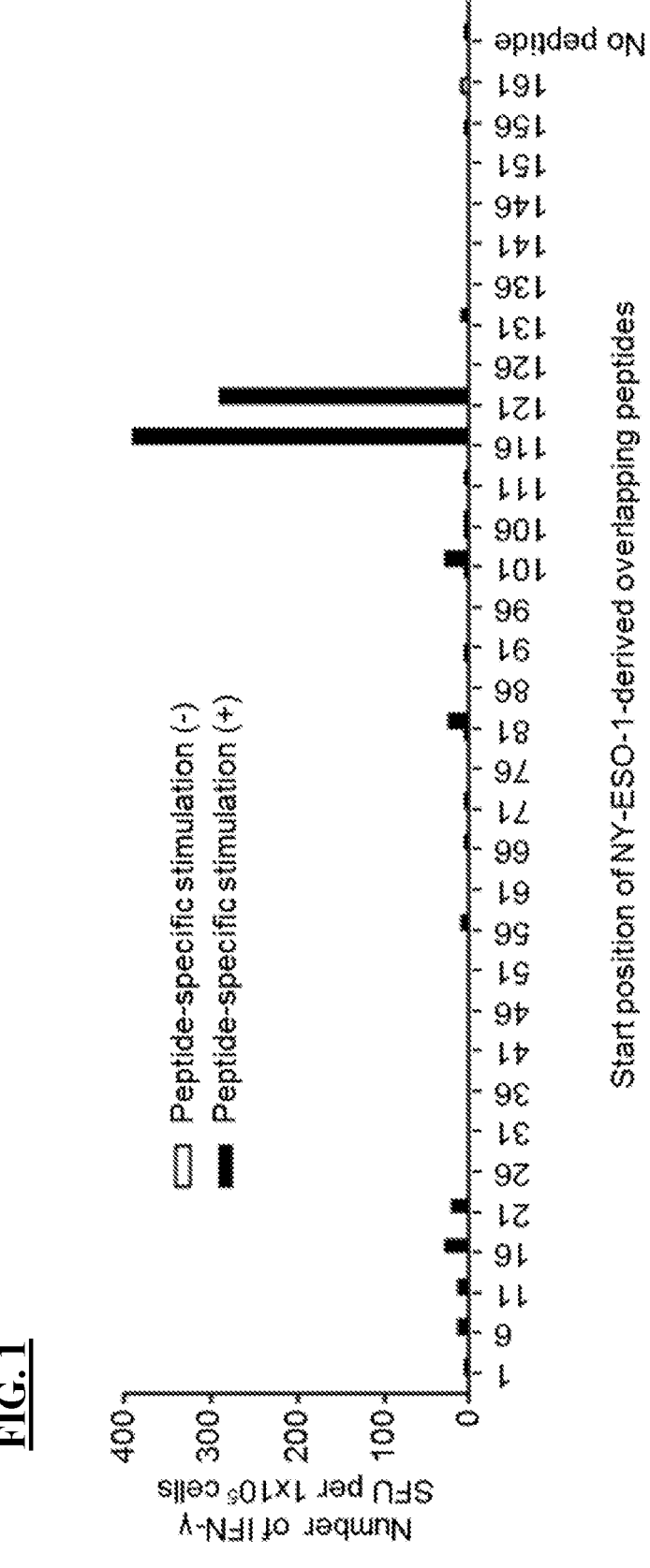
FIG. 1 is a bar graph illustrating the number of B*40:01/NY-ESO-1 T cells in melanoma TILs following stimulation with artificial APCs pulsed with overlapping peptides. The TILs stimulated once with B*40:01-artificial APCs pulsed with overlapping peptides to cover the whole protein of NY-ESO-1 were employed as responder cells in IFN-γ ELISPOT analysis. B*40:01-artificial APCs pulsed with NY-ESO-1-derived overlapping peptides were used as stimulator cells. Following one controlled peptide-specific stimulation, the TILs showed positive responses to two adjacent peptides with the shared sequence 121 VLLKEFTVSGNILTI135 (see also Table 5).

The present disclosure is directed to TCRs or antigen binding portions thereof that specifically bind to an epitope on NY-ESO-1, nucleic acid molecules that encode the same, and cells that comprise the TCR or the nucleic acid molecule. Some aspects of the present disclosure are directed to methods of treating a caner in a subject in need thereof, comprising administering to the subject the cell. Other aspects of the present disclosure are directed to HLA class I molecules complexed to a peptide comprising the epitope of NY-ESO-1.

I. Terms

In order that the present disclosure can be more readily understood, certain terms are first defined. As used in this application, except as otherwise expressly provided herein, each of the following terms shall have the meaning set forth below. Additional definitions are set forth throughout the application.

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "about" is used herein to mean approximately, roughly, around, or in the regions of. When the term "about" is used in conjunction with a numerical range, it modifies that range by extending the boundaries above and below the numerical values set forth. In general, the term "about" is used herein to modify a numerical value above and below the stated value by a variance of 10 percent, up or down (higher or lower).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, nucleotide sequences are written left to right in 5' to 3' orientation. Amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

"Administering" refers to the physical introduction of an agent to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

The term "T cell receptor" (TCR), as used herein, refers to a heteromeric cell-surface receptor capable of specifically interacting with a target antigen. As used herein, "TCR" includes but is not limited to naturally occurring and non-naturally occurring TCRs; full-length TCRs and antigen binding portions thereof; chimeric TCRs; TCR fusion constructs; and synthetic TCRs. In human, TCRs are expressed on the surface of T cells, and they are responsible for T cell recognition and targeting of antigen presenting cells. Antigen presenting cells (APCs) display fragments of foreign proteins (antigens) complexed with the major histocompatibility complex (MHC; also referred to herein as complexed with an HLA molecule, e.g., an HLA class 1 molecule). A TCR recognizes and binds to the antigen: HLA complex and recruits CD3 (expressed by T cells), activating the TCR. The activated TCR initiates downstream signaling and an immune response, including the destruction of the EPC.

In general, a TCR can comprise two chains, an alpha chain and a beta chain (or less commonly a gamma chain and a delta chain), interconnected by disulfide bonds. Each chain comprises a variable domain (alpha chain variable domain and beta chain variable domain) and a constant region (alpha chain constant region and beta chain constant region). The variable domain is located distal to the cell membrane, and the variable domain interacts with an antigen. The constant region is located proximal to the cell membrane. A TCR can further comprises a transmembrane region and a short cytoplasmic tail. As used herein, the term "constant region" encompasses the transmembrane region and the cytoplasmic tail, when present, as well as the traditional "constant region."

The variable domains can be further subdivided into regions of hypervariability, termed complementarity determining regions (CDRs), interspersed with regions that are more conserved, termed framework regions (FR). Each alpha chain variable domain and beta chain variable domain comprises three CDRs and four FRs: FR1, CDR1, FR2, CDR2, FR3, CDR3, FR4. Each variable domain contains a binding domain that interacts with an antigen. Though all three CDRs on each chain are involved in antigen binding, CDR3 is believed to be the primary antigen binding region. CDR1 is also interacts with the antigen, while CD2 is believed to primarily recognize the HLA complex.

Where not expressly stated, and unless the context indicates otherwise, the term "TCR" also includes an antigen-binding fragment or an antigen-binding portion of any TCR disclosed herein, and includes a monovalent and a divalent fragment or portion, and a single chain TCR. The term "TCR" is not limited to naturally occurring TCRs bound to the surface of a T cell. As used herein, the term "TCR" further refers to a TCR described herein that is expressed on the surface of a cell other than a T cell (e.g., a cell that naturally expresses or that is modified to express CD3, as described herein), or a TCR described herein that is free from a cell membrane (e.g., an isolated TCR or a soluble TCR).

An "antigen binding molecule," "portion of a TCR," or "TCR fragment" refers to any portion of an TCR less than the whole. An antigen binding molecule can include the antigenic complementarity determining regions (CDRs).

An "antigen" refers to any molecule, e.g., a peptide, that provokes an immune response or is capable of being bound by a TCR. An "epitope," as used herein, refers to a portion of a polypeptide that provokes an immune response or is capable of being bound by a TCR. The immune response may involve either antibody production, or the activation of specific immunologically-competent cells, or both. A person of skill in the art would readily understand that any macromolecule, including virtually all proteins or peptides, can serve as an antigen. An antigen and/or an epitope can be endogenously expressed, i.e. expressed by genomic DNA, or can be recombinantly expressed. An antigen and/or an epitope can be specific to a certain tissue, such as a cancer cell, or it can be broadly expressed. In addition, fragments of larger molecules can act as antigens. In one embodiment, antigens are tumor antigens. An epitope can be present in a longer polypeptide (e.g., in a protein), or an epitope can be present as a fragment of a longer polypeptide. In some embodiments, an epitope is complexed with a major histocompatibility complex (MHC; also referred to herein as complexed with an HLA molecule, e.g., an HLA class 1 molecule).

"NY-ESO-1," "New York esophageal squamous cell carcinoma 1," "cancer-testis antigen 1B," or "CTAG1B," as used herein, refers to a tumor antigen with expression in numerous cancer types. NY-ESO-1 is a member of the cancer-testis antigen family, which are characterized by expression that is largely limited to the testicular germ cells and placenta trophoblasts, with little or no expression in healthy adult somatic cells. NY-ESO-1 expression can be detected during embryonic development, and NY-ESO-1 expression is maintained in the spermatogonia and primary spermatocytes. In females, NY-ESO-1 expression quickly decreases in the female oogonia. NY-ESO-1 RNA has been detected at low levels in ovarian and endometrial tissue; however, NY-ESO-1 protein has not been found in these tissues. The NY-ESO-1 protein (SEQ ID NO: 52; Table 1) is an 18-kDa protein with 180 amino acids. See, e.g., Thomas et al., *Front. Immunol.* 9:947 (2018).

TABLE 1

| NY-ESO-1 Amino Acid Sequence | |
| --- | --- |
| SEQ ID NO: | NY-ESO-1 Amino Acid Sequence |
| 52 | MQAEGRGTGGSTGDADGPGGPGIPDGPGGNAGGPGEAGATG GRGPRGAGAARASGPGGGAPRGPHGGAASGLNGCCRCGARG PESRLLEFYLAMPFATPMEAELARRSLAQDAPPLPVPGVLL KEFTVSGNILTIRLTAADHRQLQLSISSCLQQLSLLMWITQ CFLPVFLAQPPSGQRR |

The term "HLA," as used herein, refers to the human leukocyte antigen. HLA genes encode the major histocompatibility complex (MHC) proteins in humans. MHC proteins are expressed on the surface of cells, and are involved in activation of the immune response. HLA class I genes encode MHC class I molecules, which are expressed on the surface of cells in complex with peptide fragments (antigens) of self or non-self proteins. T cells expressing TCR and CD3 recognize the antigen: MHC class I complex and initiate an immune response to target and destroy antigen presenting cells displaying non-self proteins.

As used herein, an "HLA class I molecule" or "HLA class I molecule" refers to a protein product of a wild-type or variant HLA class I gene encoding an MHC class I molecule. Accordingly, "HLA class I molecule" and "MHC class I molecule" are used interchangeably herein.

The MHC Class I molecule comprises two protein chains: the alpha chain and the B2-microglobulin (B2m) chain. Human B2m is encoded by the B2M gene. The amino acid sequence of B2m is set forth in SEQ ID NO: 16 (Table 2). The alpha chain of the MHC Class I molecule is encoded by the HLA gene complex. The HLA complex is located within the 6p21.3 region on the short arm of human chromosome 6 and contains more than 220 genes of diverse function. The HLA gene are highly variant, with over 20,000 HLA alleles and related alleles, including over 15,000 HLA Class I alleles, known in the art, encoding thousands of HLA proteins, including over 10,000 HLA Class I proteins (see, e.g., hla.alleles.org, last visited Feb. 27, 2019). There are at least three genes in the HLA complex that encode an MHC Class I alpha chain protein: HLA-A, HLA-B, and HLA-C. In addition, HLA-E, HLA-F, and HLA-G encode proteins that associate with the MHC Class I molecule.

TABLE 2

| Amino Acid Sequence of Human β2m | |
| --- | --- |
| SEQ ID NO: | Sequence |
| 16 | MSRSVALAVLALLSLSGLEAIQRTPKIQVYSRHPAENGKSNF LNCYVSGFHPSDIEVDLLKNGERIEKVEHSDLSFSKDWSFYL LYYTEFTPTEKDEYACRVNHVTLSQPKIVKWDRDM |

The term "autologous" refers to any material derived from the same individual to which it is later to be re-introduced. For example, an autologous T cell therapy comprises administering to a subject a T cell that was isolated from the same subject. The term "allogeneic" refers to any material derived from one individual which is then introduced to another individual of the same species. For example, an allogeneic T cell transplantation comprises administering to a subject a T cell that was obtained from a donor other than the subject.

A "cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" can include a tumor. Examples of cancers that can be treated by the methods of the present invention include, but are not limited to, cancers of the immune system including lymphoma, leukemia, and other leukocyte malignancies. In some embodiments, the methods of the present invention can be used to reduce the tumor size of a tumor derived from, for example, bone cancer, renal cancer, prostate cancer, breast cancer, colon cancer, lung cancer, cutaneous or intraocular malignant melanoma, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia (AML), chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, other B cell malignancies, and combinations of said cancers. The particular cancer can be responsive to chemo- or radiation therapy or the cancer can be refractory. A refractory cancer refers to a cancer that is not amendable to surgical intervention, and the cancer is either initially unresponsive to chemo- or radiation therapy or the cancer becomes unresponsive over time.

An "anti-tumor effect" as used herein, refers to a biological effect that can present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect can also refer to the prevention of the occurrence of a tumor, e.g., a vaccine.

The term "progression-free survival," which can be abbreviated as PFS, as used herein refers to the time from the treatment date to the date of disease progression per the revised IWG Response Criteria for Malignant Lymphoma or death from any cause.

"Disease progression" or "progressive disease," which can be abbreviated as PD, as used herein, refers to a worsening of one or more symptom associated with a particular disease. For example, disease progression for a subject afflicted with a cancer can include an increase in the number or size of one or more malignant lesions, tumor metastasis, and death.

The "duration of response," which can be abbreviated as DOR, as used herein refers to the period of time between a subject's first objective response to the date of confirmed disease progression, per the revised IWG Response Criteria for Malignant Lymphoma, or death.

The term "overall survival," which can be abbreviated as OS, is defined as the time from the date of treatment to the date of death.

A "cytokine," as used herein, refers to a non-antibody protein that is released by one cell in response to contact with a specific antigen, wherein the cytokine interacts with a second cell to mediate a response in the second cell. A cytokine can be endogenously expressed by a cell or administered to a subject. Cytokines may be released by immune cells, including macrophages, B cells, T cells, and mast cells to propagate an immune response. Cytokines can induce various responses in the recipient cell. Cytokines can include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines can promote an inflammatory response. Examples of homeostatic cytokines include, but are not limited to, IL-2, IL-4, IL-5, IL-7, IL-10, IL-12p40, IL-12p70, IL-15, and interferon (IFN) gamma. Examples of pro-inflammatory cytokines include, but are not limited to, IL-1a, IL-1b, IL-6, IL-13, IL-17a, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), and perforin. Examples of acute phase-proteins include, but are not limited to, C-reactive protein (CRP) and serum amyloid A (SAA).

"Chemokines" are a type of cytokine that mediates cell chemotaxis, or directional movement. Examples of chemokines include, but are not limited to, IL-8, IL-16, eotaxin, eotaxin-3, macrophage-derived chemokine (MDC or CCL22), monocyte chemotactic protein 1 (MCP-1 or CCL2), MCP-4, macrophage inflammatory protein 1α (MIP-1α, MIP-1a), MIP-1β (MIP-1b), gamma-induced protein 10 (IP-10), and thymus and activation regulated chemokine (TARC or CCL17).

Other examples of analytes and cytokines of the present invention include, but are not limited to chemokine (C-C motif) ligand (CCL) 1, CCL5, monocyte-specific chemokine 3 (MCP3 or CCL7), monocyte chemoattractant protein 2 (MCP-2 or CCL8), CCL13, IL-1, IL-3, IL-9, IL-11, IL-12, IL-14, IL-17, IL-20, IL-21, granulocyte colony-stimulating factor (G-CSF), leukemia inhibitory factor (LIF), oncostatin M (OSM), CD154, lymphotoxin (LT) beta, 4-1BB ligand (4-1BBL), a proliferation-inducing ligand (APRIL), CD70, CD153, CD178, glucocorticoid-induced TNFR-related ligand (GITRL), tumor necrosis factor superfamily member 14 (TNFSF14), OX40L, TNF- and ApoL-related leukocyte-expressed ligand 1 (TALL-1), or TNF-related apoptosis-inducing ligand (TRAIL).

A "therapeutically effective amount," "effective dose," "effective amount," or "therapeutically effective dosage" of a drug or therapeutic agent is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

The term "lymphocyte" as used herein includes natural killer (NK) cells, T cells, or B cells. NK cells are a type of cytotoxic (cell toxic) lymphocyte that represent a major component of the inherent immune system. NK cells reject tumors and cells infected by viruses. It works through the process of apoptosis or programmed cell death. They were termed "natural killers" because they do not require activation in order to kill cells. T-cells play a major role in cell-mediated-immunity (no antibody involvement). T-cell receptors (TCR) differentiate T cells from other lymphocyte types. The thymus, a specialized organ of the immune system, is primarily responsible for the T cell's maturation. There are six types of T-cells, namely: Helper T-cells (e.g., CD4+ cells), Cytotoxic T-cells (also known as TC, cytotoxic T lymphocyte, CTL, T-killer cell, cytolytic T cell, CD8+ T-cells or killer T cell), Memory T-cells ((i) stem memory $T_{SCM}$ cells, like naive cells, are CD45RO−, CCR7+, CD45RA+, CD62L+ (L-selectin), CD27+, CD28+ and IL-7Rα+, but they also express large amounts of CD95, IL-2RB, CXCR3, and LFA-1, and show numerous functional attributes distinctive of memory cells); (ii) central memory $T_{CM}$ cells express L-selectin and the CCR7, they secrete IL-2, but not IFNγ or IL-4, and (iii) effector memory TEM cells, however, do not express L-selectin or CCR7 but produce effector cytokines like IFNγ and IL-4), Regulatory T-cells (Tregs, suppressor T cells, or CD4+CD25+ regulatory T cells), Natural Killer T-cells (NKT) and Gamma Delta T-cells. B-cells, on the other hand, play a principal role in humoral immunity (with antibody involvement). A B cell makes antibodies and antigens and performs the role of antigen-presenting cells (APCs) and turns into memory B-cells after activation by antigen interaction. In mammals, immature B-cells are formed in the bone marrow, where its name is derived from.

The term "genetically engineered" or "engineered" refers to a method of modifying the genome of a cell, including, but not limited to, deleting a coding or non-coding region or a portion thereof or inserting a coding region or a portion thereof. In some embodiments, the cell that is modified is a lymphocyte, e.g., a T cell or a modified cell that expresses CD3, which can either be obtained from a patient or a donor. The cell can be modified to express an exogenous construct, such as, e.g., a T cell receptor (TCR) disclosed herein, which is incorporated into the cell's genome. In some embodiments, the cell is modified to express CD3.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy include, but are not limited to, T cell therapies. T cell therapy can include adoptive T cell therapy, tumor-infiltrating lymphocyte (TIL) immunotherapy, autologous cell therapy, engineered autologous cell therapy (eACT), and allogeneic T cell transplantation.

Cells used in an immunotherapy described herein can come from any source known in the art. For example, T cells can be differentiated in vitro from a hematopoietic stem cell population, or T cells can be obtained from a subject. T cells can be obtained from, e.g., peripheral blood mononuclear cells, bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by references in its entirety. An immunotherapy can also comprise administering a modified cell to a subject, wherein the modified cell expresses CD3 and a TCR disclosed herein. In some embodiments, the modified cell is not a T cell.

A "patient" as used herein includes any human who is afflicted with a cancer (e.g., a lymphoma or a leukemia). The terms "subject" and "patient" are used interchangeably herein.

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

"Stimulation," as used herein, refers to a primary response induced by binding of a stimulatory molecule with its cognate ligand, wherein the binding mediates a signal transduction event. A "stimulatory molecule" is a molecule on a T cell, e.g., the T cell receptor (TCR)/CD3 complex, that specifically binds with a cognate stimulatory ligand present on an antigen present cell. A "stimulatory ligand" is a ligand that when present on an antigen presenting cell (e.g., an aAPC, a dendritic cell, a B-cell, and the like) can specifically bind with a stimulatory molecule on a T cell, thereby mediating a primary response by the T cell, including, but not limited to, activation, initiation of an immune response, proliferation, and the like. Stimulatory ligands include, but are not limited to, an MHC Class I molecule loaded with a peptide, an anti-CD3 antibody, a superagonist anti-CD28 antibody, and a superagonist anti-CD2 antibody.

The terms "conditioning" and "pre-conditioning" are used interchangeably herein and indicate preparing a patient in need of a T cell therapy for a suitable condition. Conditioning as used herein includes, but is not limited to, reducing the number of endogenous lymphocytes, removing a cytokine sink, increasing a serum level of one or more homeostatic cytokines or pro-inflammatory factors, enhancing an effector function of T cells administered after the conditioning, enhancing antigen presenting cell activation and/or availability, or any combination thereof prior to a T cell therapy. In one embodiment, "conditioning" comprises increasing a serum level of one or more cytokines, e.g., interleukin 7 (IL-7), interleukin 15 (IL-15), interleukin 10 (IL-10), interleukin 5 (IL-5), gamma-induced protein 10 (IP-10), interleukin 8 (IL-8), monocyte chemotactic protein 1 (MCP-1), placental growth factor (PLGF), C-reactive protein (CRP), soluble intercellular adhesion molecule 1 (sICAM-1), soluble vascular adhesion molecule 1 (sVCAM-1), or any combination thereof. In another embodiment, "conditioning" comprises increasing a serum level of IL-7, IL-15, IP-10, MCP-1, PLGF, CRP, or any combination thereof.

"Treatment" or "treating" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease. In one embodiment, "treatment" or "treating" includes a partial remission. In another embodiment, "treatment" or "treating" includes a complete remission.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 10% (i.e., ±10%). For example, about 3 mg can include any number between 2.7 mg and 3.3 mg (for 10%). Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

As described herein, any concentration range, percentage range, ratio range or integer range is to be understood to include the value of any integer within the recited range and, when appropriate, fractions thereof (such as one-tenth and one-hundredth of an integer), unless otherwise indicated.

Various aspects of the invention are described in further detail in the following subsections.

II. Compositions of the Disclosure

The present disclosure is directed to T Cell Receptors (TCRs) or antigen binding portions thereof that specifically bind to an epitope on NY-ESO-1, nucleic acid molecules that encode the same, and cells that comprise the TCR or the nucleic acid molecule. Some aspects of the present disclosure are directed to methods of treating a caner in a subject in need thereof, comprising administering to the subject a cell comprising the TCRs described herein. Other aspects of the present disclosure are directed to an epitope of NY-ESO-1 that the TCRs bind to and HLA class I molecules complexed to a peptide comprising the epitope of NY-ESO-1.

The T-cell receptor, or TCR, is a molecule found on the surface of T cells, or T lymphocytes, that is responsible for recognizing fragments of antigen as peptides bound to major histocompatibility complex (MHC) molecules. The binding between TCR and antigen peptides is of relatively low affinity and is degenerate: that is, many TCRs recognize the same antigen peptide and many antigen peptides are recognized by the same TCR.

The TCR is composed of two different protein chains (that is, it is a heterodimer). In humans, in 95% of T cells the TCR consists of an alpha (α) chain and a beta (β) chain (encoded by TRA and TRB, respectively), whereas in 5% of T cells, the TCR consists of gamma and delta (γ/δ) chains (encoded by TRG and TRD, respectively). This ratio changes during ontogeny and in diseased states (such as leukemia). It also differs between species. Orthologues of the 4 loci have been mapped in various species. Each locus can produce a variety of polypeptides with constant and variable regions.

When the TCR engages with antigenic peptide and MHC (peptide/MHC), the T lymphocyte is activated through signal transduction, that is, a series of biochemical events mediated by associated enzymes, co-receptors, specialized adaptor molecules, and activated or released transcription factors.

II.A. Nucleic Acid Molecules

Certain aspects of the present disclosure are directed to nucleic acid molecules comprising (i) a first nucleotide sequence encoding a recombinant TCR or an antigen binding portion thereof that specifically binds human NY-ESO-1 ("anti-NY-ESO-1 TCR"); and (ii) a second nucleotide sequence, wherein the second nucleotide sequence or the polypeptide encoded by the second nucleotide sequence inhibits the expression of an endogenous TCR. In some embodiments, the second nucleotide sequence is a non-naturally occurring sequence. In other embodiments, the second nucleotide sequence is synthetic. In yet other embodiments, the second nucleotide sequence comprises a sequence that targets a nucleotide sequence encoding the endogenous TCR. In some embodiments, the anti-NY-ESO-1 TCR cross competes for binding to human NY-ESO-1 with a reference TCR. In some embodiments, the the amino acid sequence set forth in SEQ ID NO: 2. In some embodiments, the reference TCR comprises an alpha chain and a beta chain, wherein the alpha chain comprises an amino acid sequence as set forth in SEQ ID NO: 1 and the beta chain comprises an amino acid sequence as set forth in SEQ ID NO: 2.

TABLE 3

Alpha Chain and Beta Chain TCR Sequences

| SEQ ID NO: | TCR Chain | Sequence |
|---|---|---|
| 1 | Alpha Chain | METLLGVSLVILWLQLARVNSQQGEEDPQALSIQEGENATMNCSYKTSINNLQW YRQNSGRGLVHLILIRSNEREKHSGRLRVTLDTSKKSSSLLITASRAADTASYF CATDRGTDKLIFGTGTRLQVFPNIQNPDPAVYQLRDSKSSDKSVCLFTDFDSQT NVSQSKDSDVYITDKTVLDMRSMDFKSNSAVAWSNKSDFACANAFNNSIIPEDT FFPSPESSCDVKLVEKSFETDTNLNFQNLSVIGFRILLLKVAGFNLLMTLRLWS SZ |
| 17 | Alpha Chain | ATGGAAACTCTCCTGGGAGTGTCTTTGGTGATTCTATGGCTTCAACTGGCTAGG GTGAACAGTCAACAGGGAGAAGAGGATCCTCAGGCCTTGAGCATCCAGGAGGGT GAAAATGCCACCATGAACTGCAGTTACAAAACTAGTATAAACAATTTACAGTGG TATAGACAAAATTCAGGTAGAGGCCTTGTCCACCTAATTTTAATACGTTCAAAT GAAAGAGAGAAACACAGTGGAAGATTAAGAGTCACGCTTGACACTTCCAAGAAA AGCAGTTCCTTGTTGATCACGGCTTCCCGGGCAGCAGACACTGCTTCTTACTTC TGTGCTACGGACCGGGGCACCGACAAGCTCATCTTTGGGACTGGGACCAGATTA CAAGTCTTTCCAAATATCCAGAACCCTGACCCTGCCGTGTACCAGCTGAGAGAC TCTAAATCCAGTGACAAGTCTGTCTGCCTATTCACCGATTTTGATTCTCAAACA AATGTGTCACAAAGTAAGGATTCTGATGTGTATATCACAGACAAAACTGTGCTA GACATGAGGTCTATGGACTTCAAGAGCAACAGTGCTGTGGCCTGGAGCAACAAA TCTGACTTTGCATGTGCAAACGCCTTCAACAACAGCATTATTCCAGAAGACACC TTCTTCCCCAGCCCAGAAAGTTCCTGTGATGTCAAGCTGGTCGAGAAAAGCTTT GAAACAGATACGAACCTAAACTTTCAAAACCTGTCAGTGATTGGGTTCCGAATC CTCCTCCTGAAAGTGGCCGGGTTTAATCTGCTCATGACGCTGCGGCTGTGGTCC AGCTGA |
| 2 | Beta Chain | MSLGLLCCAAFSLLWAGPVNAGVTQTPKFRVLKTGQSMTLLCAQDMNHEYMYWY RQDPGMGLRLIHYSVGEGTTAKGEVPDGYNVSRLKKQNFLLGLESAAPSQTSVY FCASSPGVGTEAFFGQGTRLTVVEDLNKVFPPEVAVFEPSEAEISHTQKATLVC LATGFFPDHVELSWWVNGKEVHSGVSTDPQPLKEQPALNDSRYCLSSRLRVSAT FWQNPRNHFRCQVQFYGLSENDEWTQDRAKPVTQIVSAEAWGRADCGFTSVSYQ QGVLSATILYEILLGRPPCMLCWSAPCVDGHGQEKZ |
| 18 | Beta Chain | ATGAGCCTCGGGCTCCTGTGCTGTGCAGCCTTTTCTCTCCTGTGGGCAGGTCCA GTGAATGCTGGTGTCACTCAGACCCCAAAATTCCGGGTCCTGAAGACAGGACAG AGCATGACACTGCTGTGTGCCCAGGATATGAACCATGAATACATGTACTGGTAT CGACAAGACCCAGGCATGGGGCTGAGGCTGATTCATTACTCAGTTGGTGAGGGT ACAACTGCCAAAGGAGAGGTCCCTGATGGCTACAATGTCTCCAGATTAAAAAAA CAGAATTTCCTGCTGGGGTTGGAGTCGGCTGCTCCCTCCCAAACATCTGTGTAC TTCTGTGCCAGCAGTCCCGGGGTGGGCACTGAAGCTTTCTTTGGACAAGGCACC AGACTCACAGTTGTAGAGGACCTGAACAAGGTGTTCCCACCCGAGGTCGCTGTG TTTGAGCCATCAGAAGCAGAGATCTCCCACACCCAAAAGGCCACACTGGTGTGC CTGGCCACAGGCTTCTTCCCTGACCACGTGGAGCTGAGCTGGTGGGTGAATGGG AAGGAGGTGCACAGTGGGGTCAGCACGGACCCGCAGCCCCTCAAGGAGCAGCCC GCCCTCAATGACTCCAGATACTGCCTGAGCAGCCGCCTGAGGGTCTCGGCCACC TTCTGGCAGAACCCCCGCAACCACTTCCGCTGTCAAGTCCAGTTCTACGGGCTC TCGGAGAATGACGAGTGGACCCAGGATAGGGCCAAACCCGTCACCCAGATCGTC AGCGCCGAGGCCTGGGGTAGAGCAGACTGTGGCTTTACCTCGGTGTCCTACCAG CAAGGGGTCCTGTCTGCCACCATCCTCTATGAGATCCTGCTAGGAAGGCCACCC TGTATGCTGTGCTGGTCAGCGCCTTGTGTTGATGGCCATGGTCAAGAGAAATGA | anti-NY-ESO-1 TCR binds the same epitope or an overlapping epitope of human NY-ESO-1 as a reference TCR.

In some embodiments, the reference TCR comprises an alpha chain and a beta chain; wherein the alpha chain comprises a complementarity determining region 1 (CDR1), a CDR2, and a CDR3; wherein the beta chain comprises a CDR1, a CDR2, and a CDR3; and wherein the reference TCR comprises the alpha chain CDR3 set forth in SEQ ID NO: 7 and the beta chain CDR3 set forth in SEQ ID NO: 10. In some embodiments, the alpha chain CDR1, CDR2, and CDR3 sequences present in the an amino acid sequence set forth in SEQ ID NO: 1, and reference TCR comprises the beta chain CDR1, CDR2, and CDR3 sequences present in II.A.1. TCR Encoded by the First Nucleotide Sequence The present disclosure is directed to a TCR encoded by the first nucleotide sequence described herein. In some embodiments, the anti-NY-ESO-1 TCR encoded by the first nucleotide sequence comprises an alpha chain and a beta chain, wherein the alpha chain comprises a variable domain comprising an alpha chain CDR1, an alpha chain CDR2, and an alpha chain CDR3; and wherein the beta chain comprises variable domain comprising a beta chain CDR1, a beta chain CDR2, and a beta chain CDR3. In some embodiments, the anti-NY-ESO-1 TCR comprises an alpha chain CDR3 comprising an amino acid sequence as set forth in SEQ ID NO: 7 (CATDRGTDKLIF). In some embodiments, the anti-NY- ESO-1 TCR comprises a beta chain CDR3 comprising an amino acid sequence as set forth in SEQ ID NO: 10 (CASSPGVGTEAFF). In some embodiments, the non-CDR regions in the alpha chain and/or the beta chain are further modified, e.g., substitution or mutation of one amino acid, two amino acids, three amino acids, four amino acids, five amino acids, or six amino acids, thereby the alpha chain and/or the beta chain are not naturally occurring. In some embodiments, the substitutions or mutations can improve the TCRs described herein in various ways, e.g., binding affinity, binding specificity, stability, viscosity, or any combination thereof.

In some embodiments, the anti-NY-ESO-1 TCR encoded by the first nucleotide sequence comprises an alpha chain CDR1, wherein the alpha chain CDR1 of the anti-NY-ESO-1 TCR comprises an amino acid sequence as set forth in SEQ ID NO: 5 (TSINN). In some embodiments, the anti-NY-ESO-1 TCR encoded by the first nucleotide sequence comprises a beta chain CDR1, wherein the beta chain CDR1 of the anti-NY-ESO-1 TCR comprises an amino acid sequence as set forth in SEQ ID NO: 8 (IRS-NERE).

In some embodiments, the anti-NY-ESO-1 TCR encoded by the first nucleotide sequence comprises an alpha chain CDR2, wherein the alpha chain CDR2 of the anti-NY-ESO-1 TCR comprises an amino acid sequence as set forth in SEQ ID NO: 6 (MNHEY). In some embodiments, the anti-NY-ESO-1 TCR encoded by the first nucleotide sequence comprises a beta chain CDR2, wherein the beta chain CDR2 of the anti-NY-ESO-1 TCR comprises an amino acid sequence as set forth in SEQ ID NO: 9 (SVGEGT).

In some embodiments, the anti-NY-ESO-1 TCR encoded by the first nucleotide sequence comprises an alpha chain variable domain having at least about 80%, at least about 85%, at least about 90%, at least about 95%, at least about 96%, at least about 97% at least about 98%, at least about 99%, or about 100% sequence identity with a variable domain of the alpha chain amino acid sequence set forth in SEQ ID NO: 1. In some embodiments, the anti-NY-ESO-1 TCR encoded by the first nucleotide sequence comprises an alpha chain variable domain having at least about 80%, at least about 85%, at least about 90%, at least about 95%, at least about 96%, at least about 97% at least about 98%, or at least about 99% sequence identity with a variable domain of the alpha chain amino acid sequence set forth in SEQ ID NO: 1, wherein the anti-NY-ESO-1 TCR comprises an alpha chain CDR3 comprising an amino acid sequence as set forth in SEQ ID NO: 7. In some embodiments, the anti-NY-ESO-1 TCR encoded by the first nucleotide sequence comprises an alpha chain variable domain present in the alpha chain amino acid sequence set forth in SEQ ID NO: 1.

In some embodiments, the anti-NY-ESO-1 TCR encoded by the first nucleotide sequence comprises a beta chain variable domain having at least about 80%, at least about 85%, at least about 90%, at least about 95%, at least about 96%, at least about 97% at least about 98%, at least about 99%, or about 100% sequence identity with a variable domain of the beta chain amino acid sequence set forth in SEQ ID NO: 2. In some embodiments, the anti-NY-ESO-1 TCR encoded by the first nucleotide sequence comprises a beta chain variable domain having at least about 80%, at least about 85%, at least about 90%, at least about 95%, at least about 96%, at least about 97% at least about 98%, or at least about 99% sequence identity with a variable domain of the beta chain amino acid sequence set forth in SEQ ID NO: 2, wherein the anti-NY-ESO-1 TCR comprises a beta chain CDR3 comprising an amino acid sequence as set forth in SEQ ID NO: 10. In some embodiments, the anti-NY-ESO-1 TCR encoded by the first nucleotide sequence comprises a beta chain variable domain present in the amino acid sequence set forth in SEQ ID NO: 2.

In some embodiments, the anti-NY-ESO-1 TCR encoded by the first nucleotide further comprises an alpha chain constant region, a beta chain constant region, or both an alpha chain constant region and a beta chain constant region. In some embodiments, the anti-NY-ESO-1 TCR encoded by the first nucleotide sequence comprises an alpha chain constant region having at least about 80%, at least about 85%, at least about 90%, at least about 95%, at least about 96%, at least about 97% at least about 98%, at least about 99%, or about 100% sequence identity with a constant region of the alpha chain amino acid sequence set forth in SEQ ID NO: 1. In some embodiments, the anti-NY-ESO-1 TCR encoded by the first nucleotide sequence comprises an alpha chain constant region having at least about 80%, at least about 85%, at least about 90%, at least about 95%, at least about 96%, at least about 97% at least about 98%, or at least about 99% sequence identity with a constant region of the alpha chain amino acid sequence set forth in SEQ ID NO: 1, wherein the anti-NY-ESO-1 TCR comprises an alpha chain CDR3 comprising an amino acid sequence as set forth in SEQ ID NO: 7. In some embodiments, the anti-NY-ESO-1 TCR encoded by the first nucleotide sequence comprises an alpha chain constant region present in the alpha chain amino acid sequence set forth in SEQ ID NO: 1. In some embodiments, the anti-NY-ESO-1 TCR encoded by the first nucleotide further comprises an alpha constant region that is different from endogenous, e.g., naturally occurring, constant regions of the alpha chain. In some embodiments, the alpha chain constant region comprises an amino acid sequence comprising at least 1, at least 2, at least 3, at least 4, or at least 5 amino acid substitutions relative to the amino acid sequence of the constant region of the alpha chain amino acid sequence set forth in SEQ ID NO: 1.

In some embodiments, the anti-NY-ESO-1 TCR encoded by the first nucleotide sequence comprises a beta chain constant region having at least about 80%, at least about 85%, at least about 90%, at least about 95%, at least about 96%, at least about 97% at least about 98%, at least about 99%, or about 100% sequence identity with a constant region of the beta chain amino acid sequence set forth in SEQ ID NO: 2. In some embodiments, the anti-NY-ESO-1 TCR encoded by the first nucleotide sequence comprises a beta chain constant region having at least about 80%, at least about 85%, at least about 90%, at least about 95%, at least about 96%, at least about 97% at least about 98%, or at least about 99% sequence identity with a constant region of the beta chain amino acid sequence set forth in SEQ ID NO: 2, wherein the anti-NY-ESO-1 TCR comprises a beta chain CDR3 comprising an amino acid sequence as set forth in SEQ ID NO: 10. In some embodiments, the anti-NY-ESO-1 TCR encoded by the first nucleotide sequence comprises a beta chain constant region present in the amino acid sequence set forth in SEQ ID NO: 2. In some embodiments, the anti-NY-ESO-1 TCR encoded by the first nucleotide further comprises a beta constant region that is different from endogenous, e.g., naturally occurring, constant regions of the beta chain. In some embodiments, the beta chain constant region comprises an amino acid sequence comprising at least 1, at least 2, at least 3, at least 4, or at least 5 amino acid substitutions relative to the amino acid sequence of the constant region of the beta chain amino acid sequence set forth in SEQ ID NO: 2.

In certain embodiments, the anti-NY-ESO-1 TCR encoded by the first nucleotide sequence comprises an alpha chain having at least about 80%, at least about 85%, at least about 90%, at least about 95%, at least about 96%, at least about 97% at least about 98%, at least about 99%, or about 100% sequence identity with the alpha chain amino acid sequence set forth in SEQ ID NO: 1. In some embodiments, the anti-NY-ESO-1 TCR encoded by the first nucleotide sequence comprises an alpha chain having at least about 80%, at least about 85%, at least about 90%, at least about 95%, at least about 96%, at least about 97% at least about 98%, at least about 99%, or about 100% sequence identity with the alpha chain amino acid sequence set forth in SEQ ID NO: 1, wherein the anti-NY-ESO-1 TCR comprises an alpha chain CDR3 comprising an amino acid sequence as set forth in SEQ ID NO: 7. In some embodiments, the anti-NY-ESO-1 TCR encoded by the first nucleotide sequence comprises an alpha chain comprising the amino acid sequence set forth in SEQ ID NO: 1.

In certain embodiments, the anti-NY-ESO-1 TCR encoded by the first nucleotide sequence comprises a beta chain having at least about 80%, at least about 85%, at least about 90%, at least about 95%, at least about 96%, at least about 97% at least about 98%, at least about 99%, or about 100% sequence identity with the beta chain amino acid sequence set forth in SEQ ID NO: 2. In some embodiments, the anti-NY-ESO-1 TCR encoded by the first nucleotide sequence comprises a beta chain having at least about 80%, at least about 85%, at least about 90%, at least about 95%, at least about 96%, at least about 97% at least about 98%, at least about 99%, or about 100% sequence identity with the beta chain amino acid sequence set forth in SEQ ID NO: 2, wherein the anti-NY-ESO-1 TCR comprises a beta chain CDR3 comprising an amino acid sequence as set forth in SEQ ID NO: 10. In some embodiments, the anti-NY-ESO-1 TCR encoded by the first nucleotide sequence comprises a beta chain comprising the amino acid sequence set forth in SEQ ID NO: 2.

In some embodiments, the anti-NY-ESO-1 TCR encoded by the first nucleotide sequence comprises an alpha chain constant region, a beta chain constant region, or both; and wherein the alpha chain constant region, the beta chain constant region, or both comprises an amino acid sequence having at least 1, at least 2, at least 3, at least 4, or at least 5 substitutions within the target sequence relative to the corresponding amino acid sequence of an endogenous TCR.

II.A.2. Epitopes

In some embodiments, the anti-NY-ESO-1 TCR encoded by the first nucleotide sequence binds the same epitope as a reference TCR. In some embodiments, the anti-NY-ESO-1 TCR binds to an epitope of NY-ESO-1 comprising the amino acid sequence set forth in SEQ ID NO: 13 (EFTVSG-NIL). In some embodiments, the anti-NY-ESO-1 TCR binds to an epitope of NY-ESO-1 consisting of an amino acid sequence as set forth in SEQ ID NO: 13. In some embodiments, the epitope consists of amino acid residues 125-133 of NY-ESO-1 (SEQ ID NO: 52), e.g., "NY-ESO-1$_{125\text{-}133}$."

In certain embodiments, the epitope is complexed with an HLA class I molecule. The human leukocyte antigen (HLA) system (the major histocompatibility complex [MHC] in humans) is an important part of the immune system and is controlled by genes located on chromosome 6. It encodes cell surface molecules specialized to present antigenic peptides to the T-cell receptor (TCR) on T cells. (See also Overview of the Immune System.) MHC molecules that present antigen (Ag) are divided into 2 main classes: Class I MHC molecules and Class II MHC molecules.

Class I MHC molecules are present as transmembrane glycoproteins on the surface of all nucleated cells. Intact class I molecules consist of an alpha heavy chain bound to a beta-2 microglobulin molecule. The heavy chain consists of 2 peptide-binding domains, an Ig-like domain, and a transmembrane region with a cytoplasmic tail. The heavy chain of the class I molecule is encoded by genes at HLA-A, HLA-B, and HLA-C loci. T cells that express CD8 molecules react with class I MHC molecules. These lymphocytes often have a cytotoxic function, requiring them to be capable of recognizing any infected cell. Because every nucleated cell expresses class I MHC molecules, all infected cells can act as antigen-presenting cells for CD8 T cells (CD8 binds to the nonpolymorphic part of the class I heavy chain). Some class I MHC genes encode nonclassical MHC molecules, such as HLA-G (which may play a role in protecting the fetus from the maternal immune response) and HLA-E (which presents peptides to certain receptors on natural killer [NK] cells).

In some embodiments, the HLA class 1 molecule is selected from an HLA-A, HLA-B, and HLA-C allele. In some embodiments, the HLA class 1 molecule is selected from an HLA-E, HLA-F, and HLA-G allele. In certain embodiments, the HLA class 1 molecule is an HLA-A allele. In certain embodiments, the HLA class 1 molecule is an HLA-B allele. In certain embodiments, the HLA class 1 molecule is an HLA-C allele.

Many HLA-A, HLA-B, and HLA-C alleles are known in the art, and any of the known alleles can be used in the present disclosure. An updated list of HLA alleles is available at hla.alleles.org/(last visited on Feb. 27, 2019). In some embodiments, the HLA class 1 molecule is an HLA-B allele selected from an HLA-B*07, an HLA-B*08, an HLA-B*13, an HLA-B*14, an HLA-B*15, an HLA-B*18, an HLA-B*27, an HLA-B*35, an HLA-B*37, an HLA-B*38, an HLA-B*39, an HLA-B*40, an HLA-B*41, an HLA-B*42, an HLA-B*44, an HLA-B*45, an HLA-B*46, an HLA-B*47, an HLA-B*48, an HLA-B*49, an HLA-B*50, an HLA-B*51, an HLA-B*52, an HLA-B*53, an HLA-B*54, an HLA-B*55, an HLA-B*56, an HLA-B*57, an HLA-B*58, an HLA-B*59, an HLA-B*67, an HLA-B*73, an HLA-B*78, an HLA-B*79, an HLA-B*81, an HLA-B*82, and an HLA-B*83. In certain embodiments, the HLA-B allele is an HLA-B*40:01 allele. In certain embodiments, the HLA-B allele is an HLA-B*40:02 allele. In certain embodiments, the HLA-B allele is an HLA-B*40:03 allele. In certain embodiments, the HLA-B allele is an HLA-B*40:04 allele. In certain embodiments, the HLA-B allele is an HLA-B*40:05 allele. In certain embodiments, the HLA-B allele is an HLA-B*40:06 allele.

In certain embodiments, the HLA class 1 molecule is an HLA-B allele selected from the group consisting of HLA-B*40:01:01, HLA-B*40:01:02:01, HLA-B*40:01:02:02, HLA-B*40:01:02:03, HLA-B*40:01:02:04, HLA-B*40:01:02:05, HLA-B*40:01:02:06, HLA-B*40:01:02:07, HLA-B*40:01:02:08, HLA-B*40:01:02:09, HLA-B*40:01:03, HLA-B*40:01:04, HLA-B*40:01:05, HLA-B*40:01:06, HLA-B*40:01:07, HLA-B*40:01:08, HLA-B*40:01:09, HLA-B*40:01:10, HLA-B*40:01:11, HLA-B*40:01:12, HLA-B*40:01:13, HLA-B*40:01:14, HLA-B*40:01:15, HLA-B*40:01:16, HLA-B*40:01:17, HLA-B*40:01:18, HLA-B*40:01:19, HLA-B*40:01:20, HLA-B*40:01:21, HLA-B*40:01:22, HLA-B*40:01:23, HLA-B*40:01:24, HLA-B*40:01:25, HLA-B*40:01:26, HLA-B*40:01:27, HLA-B*40:01:28, HLA-B*40:01:29, HLA-B*40:01:30, HLA-B*40:01:31, HLA-B*40:01:32, HLA-B*40:01:33, HLA-B*40:01:34, HLA-B*40:01:35, HLA-B*40:01:36, HLA-B*40:01:37, HLA-B*40:01:38, HLA-B*40:01:39, HLA-B*40:01:40, HLA-B*40:01:41, HLA-B*40:01:42, HLA-B*40:01:43, HLA-B*40:01:44, HLA-B*40:01:45, HLA-B*40:01:46, HLA-B*40:01:47, HLA-B*40:01:48, HLA-B*40:01:49, HLA-B*40:01:50, HLA-B*40:01:51, HLA-B*40:01:52, HLA-B*40:01:53, HLA-B*40:01:54, HLA-B*40:01:55, HLA-B*40:01:56, HLA-B*40:01:57, HLA-B*40:01:58, HLA-B*40:01:59, HLA-B*40:01:60, HLA-B*40:02:01:01, HLA-B*40:02:01:02, HLA-B*40:02:01:03, HLA-B*40:02:01:04, HLA-B*40:02:01:05, HLA-B*40:02:01:06, HLA-B*40:02:01:07, HLA-B*40:02:01:08, HLA-B*40:02:02, HLA-B*40:02:03, HLA-B*40:02:04, HLA-B*40:02:05, HLA-B*40:02:06, HLA-B*40:02:07, HLA-B*40:02:08, HLA-B*40:02:09, HLA-B*40:02:10, HLA-B*40:02:11, HLA-B*40:02:12, HLA-B*40:02:13, HLA-B*40:02:14, HLA-B*40:02:15, HLA-B*40:02:16, HLA-B*40:02:17, HLA-B*40:02:18, HLA-B*40:02:19, HLA-B*40:02:20, HLA-B*40:02:21, HLA-B*40:02:22, HLA-B*40:02:23, HLA-B*40:02:24, HLA-B*40:02:25, HLA-B*40:02:26, HLA-B*40:03:01:01, HLA-B*40:03:01:02, HLA-B*40:04:01, HLA-B*40:04:02, HLA-B*40:05:01:01, HLA-B*40:05:01:02, HLA-B*40:06:01:01, HLA-B*40:06:01:02, HLA-B*40:06:02, HLA-B*40:06:03, HLA-B*40:06:04:01, HLA-B*40:06:04:02, HLA-B*40:06:05, HLA-B*40:06:06, HLA-B*40:06:07, HLA-B*40:06:08, HLA-B*40:06:09, HLA-B*40:06:10, HLA-B*40:06:11, HLA-B*40:06:12, HLA-B*40:06:13, HLA-B*40:06:14, HLA-B*40:06:15, HLA-B*40:06:16, HLA-B*40:06:17, HLA-B*40:06:18, HLA-B*40:07, HLA-B*40:08, HLA-B*40:09, HLA-B*40:100, HLA-B*40:101, HLA-B*40:102, HLA-B*40:103, HLA-B*40:104, HLA-B*40:105, HLA-B*40:106, HLA-B*40:107, HLA-B*40:108, HLA-B*40:109, HLA-B*40:10:01:01, HLA-B*40:10:01:02, HLA-B*40:10:02, HLA-B*40:110, HLA-B*40:111, HLA-B*40:112, HLA-B*40:113, HLA-B*40:114:01, HLA-B*40:114:02, HLA-B*40:115, HLA-B*40:116, HLA-B*40:117, HLA-B*40:118, HLA-B*40:119, HLA-B*40:11:01, HLA-B*40:11:02, HLA-B*40:12, HLA-B*40:120, HLA-B*40:121, HLA-B*40:122, HLA-B*40:123, HLA-B*40:124:01, HLA-B*40:124:02, HLA-B*40:125:01, HLA-B*40:125:02, HLA-B*40:126, HLA-B*40:127, HLA-B*40:128, HLA-B*40:129, HLA-B*40:13, HLA-B*40:130:01, HLA-B*40:130:02, HLA-B*40:131, HLA-B*40:132, HLA-B*40:133, HLA-B*40:134, HLA-B*40:135, HLA-B*40:136, HLA-B*40:137, HLA-B*40:138, HLA-B*40:139, HLA-B*40:140, HLA-B*40:141, HLA-B*40:142, HLA-B*40:143, HLA-B*40:144, HLA-B*40:145, HLA-B*40:146, HLA-B*40:147, HLA-B*40:148, HLA-B*40:149, HLA-B*40:14:01, HLA-B*40:14:02, HLA-B*40:14:03, HLA-B*40:15, HLA-B*40:150, HLA-B*40:151, HLA-B*40:152, HLA-B*40:153, HLA-B*40:154, HLA-B*40:155:01, HLA-B*40:155:02, HLA-B*40:156, HLA-B*40:157, HLA-B*40:158, HLA-B*40:159, HLA-B*40:16, HLA-B*40:160:01, HLA-B*40:160:02, HLA-B*40:161, HLA-B*40:162, HLA-B*40:163, HLA-B*40:164, HLA-B*40:165, HLA-B*40:166, HLA-B*40:167, HLA-B*40:168, HLA-B*40:169, HLA-B*40:170, HLA-B*40:171, HLA-B*40:172, HLA-B*40:173, HLA-B*40:174, HLA-B*40:175, HLA-B*40:176, HLA-B*40:177, HLA-B*40:178, HLA-B*40:179, HLA-B*40:18, HLA-B*40:180, HLA-B*40:181, HLA-B*40:182, HLA-B*40:183, HLA-B*40:184, HLA-B*40:185, HLA-B*40:186:01, HLA-B*40:186:02, HLA-B*40:187, HLA-B*40:188, HLA-B*40:189, HLA-B*40:19, HLA-B*40:190, HLA-B*40:191, HLA-B*40:192, HLA-B*40:193, HLA-B*40:194, HLA-B*40:195, HLA-B*40:196, HLA-B*40:197, HLA-B*40:198, HLA-B*40:199, HLA-B*40:200, HLA-B*40:201, HLA-B*40:

202, HLA-B*40:203, HLA-B*40:204, HLA-B*40:205, HLA-B*40:206, HLA-B*40:207, HLA-B*40:208, HLA-B*40:209, HLA-B*40:20:01:01, HLA-B*40:20:01:02, HLA-B*40:21, HLA-B*40:210, HLA-B*40:211, HLA-B*40:212, HLA-B*40:213, HLA-B*40:214, HLA-B*40:215, HLA-B*40:216, HLA-B*40:217, HLA-B*40:218, HLA-B*40:219, HLA-B*40:220, HLA-B*40:221, HLA-B*40:222, HLA-B*40:223, HLA-B*40:224, HLA-B*40:225, HLA-B*40:226, HLA-B*40:227, HLA-B*40:228, HLA-B*40:229, HLA-B*40:22 57, HLA-B*40:23, HLA-B*40:230, HLA-B*40:231, HLA-B*40:232, HLA-B*40:233, HLA-B*40:234, HLA-B*40:235, HLA-B*40:236, HLA-B*40:237, HLA-B*40:238, HLA-B*40:239, HLA-B*40:24, HLA-B*40:240, HLA-B*40:241, HLA-B*40:242, HLA-B*40:243, HLA-B*40:244, HLA-B*40:245, HLA-B*40:246, HLA-B*40:247, HLA-B*40:248, HLA-B*40:249, HLA-B*40:25, HLA-B*40:250, HLA-B*40:251, HLA-B*40:252, HLA-B*40:253, HLA-B*40:254, HLA-B*40:255, HLA-B*40:256, HLA-B*40:257, HLA-B*40:258, HLA-B*40:259, HLA-B*40:26, HLA-B*40:260, HLA-B*40:261, HLA-B*40:262, HLA-B*40:263, HLA-B*40:264, HLA-B*40:265, HLA-B*40:266, HLA-B*40:267, HLA-B*40:268, HLA-B*40:269, HLA-B*40:270, HLA-B*40:271, HLA-B*40:272, HLA-B*40:273, HLA-B*40:274, HLA-B*40:275, HLA-B*40:276, HLA-B*40:277, HLA-B*40:278, HLA-B*40:279, HLA-B*40:27:01, HLA-B*40:27:02, HLA-B*40:28, HLA-B*40:280, HLA-B*40:281, HLA-B*40:282, HLA-B*40:283, HLA-B*40:284, HLA-B*40:285, HLA-B*40:286, HLA-B*40:287, HLA-B*40:288, HLA-B*40:289, HLA-B*40:29, HLA-B*40:290, HLA-B*40:291, HLA-B*40:292, HLA-B*40:293, HLA-B*40:294, HLA-B*40:295, HLA-B*40:296, HLA-B*40:297, HLA-B*40:298:01, HLA-B*40:298:02, HLA-B*40:299, HLA-B*40:30, HLA-B*40:300, HLA-B*40:301, HLA-B*40:302, HLA-B*40:303, HLA-B*40:304, HLA-B*40:305, HLA-B*40:306, HLA-B*40:307, HLA-B*40:308, HLA-B*40:309, HLA-B*40:31, HLA-B*40:310, HLA-B*40:311, HLA-B*40:312, HLA-B*40:313, HLA-B*40:314, HLA-B*40:315, HLA-B*40:316, HLA-B*40:317, HLA-B*40:318, HLA-B*40:319, HLA-B*40:32, HLA-B*40:320, HLA-B*40:321, HLA-B*40:322, HLA-B*40:323, HLA-B*40:324, HLA-B*40:325, HLA-B*40:326, HLA-B*40:327, HLA-B*40:328, HLA-B*40:329, HLA-B*40:33, HLA-B*40:330, HLA-B*40:331, HLA-B*40:332, HLA-B*40:333, HLA-B*40:334, HLA-B*40:335, HLA-B*40:336, HLA-B*40:337 98, HLA-B*40:338, HLA-B*40:339, HLA-B*40:34, HLA-B*40:340, HLA-B*40:341, HLA-B*40:342, HLA-B*40:343, HLA-B*40:344, HLA-B*40:345, HLA-B*40:346, HLA-B*40:347, HLA-B*40:348, HLA-B*40:349, HLA-B*40:350, HLA-B*40:351, HLA-B*40:352, HLA-B*40:353, HLA-B*40:354, HLA-B*40:355, HLA-B*40:356, HLA-B*40:357, HLA-B*40:358, HLA-B*40:359, HLA-B*40:35:01, HLA-B*40:35:02, HLA-B*40:36, HLA-B*40:360, HLA-B*40:361 86, HLA-B*40:362, HLA-B*40:363, HLA-B*40:364, HLA-B*40:365, HLA-B*40:366, HLA-B*40:367, HLA-B*40:368, HLA-B*40:369, HLA-B*40:37, HLA-B*40:370, HLA-B*40:371, HLA-B*40:372, HLA-B*40:373, HLA-B*40:374, HLA-B*40:375, HLA-B*40:376, HLA-B*40:377, HLA-B*40:378, HLA-B*40:379, HLA-B*40:38, HLA-B*40:380, HLA-B*40:381, HLA-

B*40:382, HLA-B*40:383, HLA-B*40:384, HLA-B*40:
385, HLA-B*40:386, HLA-B*40:387, HLA-B*40:388,
HLA-B*40:389, HLA-B*40:39, HLA-B*40:390, HLA-
B*40:391, HLA-B*40:392, HLA-B*40:393, HLA-B*40:
394, HLA-B*40:395, HLA-B*40:396, HLA-B*40:397,
HLA-B*40:398, HLA-B*40:399 57, HLA-B*40:40, HLA-
B*40:400, HLA-B*40:401, HLA-B*40:402, HLA-B*40:
403, HLA-B*40:404, HLA-B*40:406, HLA-B*40:407,
HLA-B*40:408, HLA-B*40:409, HLA-B*40:410, HLA-
B*40:411, HLA-B*40:412, HLA-B*40:413, HLA-B*40:
414, HLA-B*40:42, HLA-B*40:43, HLA-B*40:44, HLA-
B*40:45, HLA-B*40:46, HLA-B*40:47, HLA-B*40:48,
HLA-B*40:49, HLA-B*40:50, HLA-B*40:51, HLA-B*40:
52, HLA-B*40:53, HLA-B*40:54, HLA-B*40:55, HLA-
B*40:56, HLA-B*40:57, HLA-B*40:58, HLA-B*40:59,
HLA-B*40:60, HLA-B*40:61, HLA-B*40:62, HLA-B*40:
63, HLA-B*40:64:01:01, HLA-B*40:64:01:02, HLA-B*40:
65, HLA-B*40:66, HLA-B*40:67, HLA-B*40:68, HLA-
B*40:69, HLA-B*40:70:01, HLA-B*40:70:02, HLA-B*40:
71, HLA-B*40:72:01, HLA-B*40:72:02, HLA-B*40:73,
HLA-B*40:74, HLA-B*40:75, HLA-B*40:76, HLA-B*40:
77, HLA-B*40:78, HLA-B*40:79, HLA-B*40:80, HLA-
B*40:81, HLA-B*40:82, HLA-B*40:83, HLA-B*40:84,
HLA-B*40:85, HLA-B*40:86, HLA-B*40:87:01, HLA-
B*40:87:02, HLA-B*40:88, HLA-B*40:89, HLA-B*40:90,
HLA-B*40:91, HLA-B*40:92, HLA-B*40:93, HLA-B*40:
94, HLA-B*40:95, HLA-B*40:96, HLA-B*40:97, HLA-
B*40:98, and HLA-B*40:99.

II.A.3 The Second Nucleotide Sequence

The second nucleotide sequence of the nucleic acid molecule disclosed herein can be any sequence or can encode for any polypeptide that is capable of inhibiting the expression of an endogenous TCR. In some embodiments, the second nucleotide sequence is one or more siRNAs. In some embodiments, the one or more siRNAs are complementary to a target sequence within a nucleotide sequence encoding a constant region of an endogenous TCR. In certain embodiments, the one or more siRNAs are complementary to a target sequence within a nucleotide sequence encoding a constant region of wild-type, human TCR. In some embodiments, the one or more siRNAs are complementary to a target sequence within a nucleotide sequence encoding a constant region of the alpha chain of wild-type TCR. In some embodiments, the one or more siRNAs are complementary to a target sequence within a nucleotide sequence encoding a constant region of the beta chain of wild-type TCR. In some embodiments, the one or more siRNAs comprise (i) one or more siRNA's that are complementary to a target sequence within a nucleotide sequence encoding a constant region of the alpha chain of wild-type TCR and (ii) one or more siRNA's that are complementary to a target sequence within a nucleotide sequence encoding a constant region of the beta chain of wild-type TCR.

In some embodiments, the one or more siRNAs comprise a nucleotide sequence selected from the group consisting of SEQ ID NOs: 53-56 (Table 4). In some embodiments, the second nucleotide sequence of the nucleic acid molecule encodes one or more siRNAs, wherein the one or more siRNAs are complementary to a target sequence within a nucleotide sequence encoding a constant region of the alpha chain of wild-type TCR, and wherein the one or more siRNAs comprise the nucleic acid sequences set forth in SEQ ID NOs: 53 and 54.

TABLE 4 siRNA Sequences

| SEQ ID NO: | siRNA | Sequence (Nucleotides 1-19 are are ribonucleotides; nucleotides 20-21 are deoxyribonucleotides) |
|---|---|---|
| 53 | siRNA-TCRa-1 | GUAAGGAUUCUGAUGUGUAUU |
| 54 | siRNA-TCRa-2 | UACACAUCAGAAUCCUUACUU |
| 55 | siRNA-TCRb-1 | CCACCAUCCUCUAUGAGAUU |
| 56 | siRNA-TCRb-2 | AUCUCAUAGAGGAUGGUGGUU |

In some embodiments, the second nucleotide sequence of the nucleic acid molecule encodes one or more siRNAs, wherein the one or more siRNAs are complementary to a target sequence within a nucleotide sequence encoding a constant region of the beta chain of wild-type TCR, and wherein the one or more siRNAs comprise the nucleic acid sequences set forth in SEQ ID NOs: 55 and 56. In some embodiments, the second nucleotide sequence of the nucleic acid molecule encodes one or more siRNAs, wherein the one or more siRNAs comprise (i) one or more siRNAs that are complementary to a target sequence within a nucleotide sequence encoding a constant region of the alpha chain of wild-type TCR, wherein the one or more siRNAs comprise the nucleic acid sequences set forth in SEQ ID NOs: 53 and 54; and (ii) one or more siRNAs that are complementary to a target sequence within a nucleotide sequence encoding a constant region of the beta chain of wild-type TCR, wherein the one or more siRNAs comprise the nucleic acid sequences set forth in SEQ ID NOs: 55 and 56.

In some embodiments, the second nucleotide sequence of the nucleic acid molecule comprises SEQ ID NOs: 53-56. In some embodiments, the second nucleotide sequence comprises SEQ ID NOs: 53-56, wherein one or more of SEQ ID NOs: 53-56 is separated by one or more nucleic acids that do not encode an siRNA. In certain embodiments, the one or more siRNAs are selected from the siRNAs disclosed in U.S. Publication No. 2010/0273213 A1, which is incorporated by reference herein in its entirety.

In some embodiments, the second nucleotide sequence of the nucleic acid molecule encodes a protein, wherein the protein is capable of inhibiting the expression of application Ser. No. 17/436,931 Clean Version an endogenous, e.g., wild-type, TCR. In some embodiments, the second nucleotide sequence encodes Cas9.

II.A.3 Vectors

Certain aspects of the present disclosure are directed to vectors comprising a nucleic acid molecule disclosed herein. In some embodiments, the vector is a viral vector. In some embodiments, the vector is a viral particle or a virus. In some embodiments, the vector is a mammalian vector. In some embodiments, the vector is a bacterial vector.

In certain embodiments, the vector is a retroviral vector. In some embodiments, the vector is selected from the group consisting of an adenoviral vector, a lentivirus, a Sendai virus, a baculoviral vector, an Epstein Barr viral vector, a papovaviral vector, a vaccinia viral vector, a herpes simplex viral vector, and an adeno associated virus (AAV) vector. In particular embodiments, the vector is an AAV vector. In some embodiments, the vector is a lentivirus. In particular embodiments, the vector is an AAV vector. In some embodiments, the vector is a Sendai virus. In some embodiments, the vector is a hybrid vector. Examples of hybrid vectors that can be used in the present disclosure can be found in Huang and Kamihira, *Biotechnol. Adv.* 31 (2): 208-23 (2103), which is incorporated by reference herein in its entirety.

II.B. Recombinant T Cell Receptors (TCRs)

Certain aspects of the present disclosure are directed to recombinant T cell receptors (TCRs) or an antigen binding portion thereof that specifically bind human NY-ESO-1 ("an anti-NY-ESO-1 TCR"). In some embodiments, the anti-NY-ESO-1 TCR is encoded by the a nucleic acid molecule disclosed herein.

In some embodiments, the anti-NY-ESO-1 TCR cross competes for binding to human NY-ESO-1 with a reference TCR. In some embodiments, the anti-NY-ESO-1 TCR binds the same epitope or an overlapping epitope of human NY-ESO-1 as a reference TCR. In some embodiments, the reference TCR comprises an alpha chain and a beta chain, and the alpha chain comprises of the reference TCR comprises an amino acid sequence as set forth in SEQ ID NO: 1. In some embodiments, the beta chain of the reference TCR comprises an amino acid sequence as set forth in SEQ ID NO: 2.

In some embodiments, the anti-NY-ESO-1 TCR comprises an alpha chain and a beta chain, wherein the alpha chain comprises a constant region, and wherein the beta chain comprises a constant region; wherein the alpha chain constant region comprises an amino acid sequence having a least 1, at least 2, at least 3, at least 4, or at least 5 amino acid substitutions relative to the constant region of an alpha chain comprising the amino acid sequence set forth in SEQ ID NO: 1. In some embodiments, the anti-NY-ESO-1 TCR comprises an alpha chain and a beta chain, wherein the alpha chain comprises a constant region, and wherein the beta chain comprises a constant region; wherein the beta chain constant region comprises an amino acid sequence having a least 1, at least 2, at least 3, at least 4, or at least 5 amino acid substitutions relative to the constant region of a beta chain comprising the amino acid sequence set forth in SEQ ID NO: 2.

In some embodiments, the anti-NY-ESO-1 TCR comprises an alpha chain and a beta chain, wherein the alpha chain comprises a constant region, and wherein the beta chain comprises a constant region; wherein (i) the alpha chain constant region comprises an amino acid sequence having a least 1, at least 2, at least 3, at least 4, or at least 5 amino acid substitutions relative to the constant region of an alpha chain comprising the amino acid sequence set forth in SEQ ID NO: 1; and (ii) the beta chain constant region comprises an amino acid sequence having a least 1, at least 2, at least 3, at least 4, or at least 5 amino acid substitutions relative to the constant region of a beta chain comprising the amino acid sequence set forth in SEQ ID NO: 2.

In some embodiments, the alpha chain of the anti-NY-ESO-1 TCR comprises a variable domain comprising an alpha chain CDR1, an alpha chain CDR2, and an alpha chain CDR3; and the beta chain of the anti-NY-ESO-1 TCR comprises a variable domain comprising a beta chain CDR1, a beta chain CDR2, and a beta chain CDR3. In some embodiments, the anti-NY-ESO-1 TCR comprises an alpha chain CDR3 comprising an amino acid sequence as set forth in SEQ ID NO: 7. In some embodiments, the anti-NY-ESO-1 TCR comprises a beta chain CDR3 comprising an amino acid sequence as set forth in SEQ ID NO: 10.

In some embodiments, the alpha chain CDR1 of the anti-NY-ESO-1 TCR comprises an amino acid sequence as set forth in SEQ ID NO: 5. In some embodiments, the beta chain CDR1 of the anti-NY-ESO-1 TCR comprises an amino acid sequence as set forth in SEQ ID NO: 8.

In some embodiments, the alpha chain CDR2 of the anti-NY-ESO-1 TCR comprises an amino acid sequence as set forth in SEQ ID NO: 6. In some embodiments, the beta chain CDR2 of the anti-NY-ESO-1 TCR comprises an amino acid sequence as set forth in SEQ ID NO: 9.

In some embodiments, the anti-NY-ESO-1 TCR comprises an alpha chain variable domain having at least about 80%, at least about 85%, at least about 90%, at least about 95%, at least about 96%, at least about 97% at least about 98%, at least about 99%, or about 100% sequence identity with a variable domain of the alpha chain amino acid sequence set forth in SEQ ID NO: 1. In some embodiments, the anti-NY-ESO-1 TCR comprises an alpha chain variable domain having at least about 80%, at least about 85%, at least about 90%, at least about 95%, at least about 96%, at least about 97% at least about 98%, or at least about 99% sequence identity with a variable domain of the alpha chain amino acid sequence set forth in SEQ ID NO: 1, wherein the anti-NY-ESO-1 TCR comprises an alpha chain CDR3 comprising an amino acid sequence as set forth in SEQ ID NO: 7. In some embodiments, the anti-NY-ESO-1 TCR comprises an alpha chain variable domain present in the alpha chain amino acid sequence set forth in SEQ ID NO: 1.

In some embodiments, the anti-NY-ESO-1 TCR comprises a beta chain variable domain having at least about 80%, at least about 85%, at least about 90%, at least about 95%, at least about 96%, at least about 97% at least about 98%, at least about 99%, or about 100% sequence identity with a variable domain of the beta chain amino acid sequence set forth in SEQ ID NO: 2. In some embodiments, the anti-NY-ESO-1 TCR comprises a beta chain variable domain having at least about 80%, at least about 85%, at least about 90%, at least about 95%, at least about 96%, at least about 97% at least about 98%, or at least about 99% sequence identity with a variable domain of the beta chain amino acid sequence set forth in SEQ ID NO: 2, wherein the anti-NY-ESO-1 TCR comprises a beta chain CDR3 comprising an amino acid sequence as set forth in SEQ ID NO: 10. In some embodiments, the anti-NY-ESO-1 TCR comprises a beta chain variable domain present in the beta chain amino acid sequence set forth in SEQ ID NO: 2.

In some embodiments, the anti-NY-ESO-1 TCR encoded by the first nucleotide further comprises an alpha chain constant region, a beta chain constant region, or both an alpha chain constant region and a beta chain constant region. In some embodiments, the anti-NY-ESO-1 TCR comprises an alpha chain constant region having at least about 80%, at least about 85%, at least about 90%, at least about 95%, at least about 96%, at least about 97% at least about 98%, at least about 99%, or about 100% sequence identity with a constant region of the alpha chain amino acid sequence set forth in SEQ ID NO: 1. In some embodiments, the anti-NY-ESO-1 TCR comprises an alpha chain constant region having at least about 80%, at least about 85%, at least about 90%, at least about 95%, at least about 96%, at least about 97% at least about 98%, or at least about 99% sequence identity with a constant region of the alpha chain amino acid sequence set forth in SEQ ID NO: 1, wherein the anti-NY-ESO-1 TCR comprises an alpha chain CDR3 comprising an amino acid sequence as set forth in SEQ ID NO: 7. In some embodiments, the anti-NY-ESO-1 TCR comprises an alpha chain constant region present in the alpha chain amino acid sequence set forth in SEQ ID NO: 1. In some embodiments, the anti-NY-ESO-1 TCR encoded by the first nucleotide further comprises an alpha constant region that is different from endogenous, e.g., naturally occurring, constant regions of the alpha chain. In some embodiments, the alpha chain constant region comprises an amino acid sequence comprising at least 1, at least 2, at least 3, at least 4, or at least 5 amino acid substitutions relative to the amino acid sequence of the constant region of the alpha chain amino acid sequence set forth in SEQ ID NO: 1.

In some embodiments, the anti-NY-ESO-1 TCR comprises a beta chain constant region having at least about 80%, at least about 85%, at least about 90%, at least about 95%, at least about 96%, at least about 97% at least about 98%, at least about 99%, or about 100% sequence identity with a constant region of the beta chain amino acid sequence set forth in SEQ ID NO: 2. In some embodiments, the anti-NY-ESO-1 TCR comprises a beta chain constant region having at least about 80%, at least about 85%, at least about 90%, at least about 95%, at least about 96%, at least about 97% at least about 98%, or at least about 99% sequence identity with a constant region of the beta chain amino acid sequence set forth in SEQ ID NO: 2, wherein the anti-NY-ESO-1 TCR comprises a beta chain CDR3 comprising an amino acid sequence as set forth in SEQ ID NO: 10. In some embodiments, the anti-NY-ESO-1 TCR comprises a beta chain constant region present in the beta chain amino acid sequence set forth in SEQ ID NO: 2. In some embodiments, the anti-NY-ESO-1 TCR encoded by the first nucleotide further comprises a beta constant region that is different from endogenous, e.g., naturally occurring, constant regions of the beta chain. In some embodiments, the beta chain constant region comprises an amino acid sequence comprising at least 1, at least 2, at least 3, at least 4, or at least 5 amino acid substitutions relative to the amino acid sequence of the constant region of the beta chain amino acid sequence set forth in SEQ ID NO: 2.

In certain embodiments, the anti-NY-ESO-1 TCR comprises an alpha chain having at least about 80%, at least about 85%, at least about 90%, at least about 95%, at least about 96%, at least about 97% at least about 98%, at least about 99%, or about 100% sequence identity with the alpha chain amino acid sequence set forth in SEQ ID NO: 1. In some embodiments, the anti-NY-ESO-1 TCR comprises an alpha chain having at least about 80%, at least about 85%, at least about 90%, at least about 95%, at least about 96%, at least about 97% at least about 98%, at least about 99%, or about 100% sequence identity with the alpha chain amino acid sequence set forth in SEQ ID NO: 1, wherein the anti-NY-ESO-1 TCR comprises an alpha chain CDR3 comprising an amino acid sequence as set forth in SEQ ID NO: 7. In some embodiments, the anti-NY-ESO-1 TCR comprises an alpha chain comprising the amino acid sequence set forth in SEQ ID NO: 1.

In certain embodiments, the anti-NY-ESO-1 TCR comprises a beta chain having at least about 80%, at least about 85%, at least about 90%, at least about 95%, at least about 96%, at least about 97% at least about 98%, at least about 99%, or about 100% sequence identity with the beta chain amino acid sequence set forth in SEQ ID NO: 2. In some embodiments, the anti-NY-ESO-1 TCR comprises a beta chain having at least about 80%, at least about 85%, at least about 90%, at least about 95%, at least about 96%, at least about 97% at least about 98%, at least about 99%, or about 100% sequence identity with the beta chain amino acid sequence set forth in SEQ ID NO: 2, wherein the anti-NY-ESO-1 TCR comprises a beta chain CDR3 comprising an amino acid sequence as set forth in SEQ ID NO: 10. In some embodiments, the anti-NY-ESO-1 TCR comprises a beta chain comprising the amino acid sequence set forth in SEQ ID NO: 2.

In some embodiments, the anti-NY-ESO-1 TCR comprises an alpha chain constant region, a beta chain constant region, or both; and wherein the alpha chain constant region, the beta chain constant region, or both comprises an amino acid sequence having at least 1, at least 2, at least 3, at least 4, or at least 5 substitutions within the target sequence relative to the corresponding amino acid sequence of an endogenous TCR.

II.B.2. Epitopes

In some embodiments, the anti-NY-ESO-1 TCR binds the same epitope as a reference TCR. In some embodiments, the anti-NY-ESO-1 TCR binds to an epitope of NY-ESO-1 comprising the amino acid sequence set forth in SEQ ID NO: 13. In some embodiments, the anti-NY-ESO-1 TCR binds to an epitope of NY-ESO-1 consisting of an amino acid sequence as set forth in SEQ ID NO: 13. In some embodiments, the epitope consists of amino acid residues 125-133 of NY-ESO-1 (SEQ ID NO: 52), e.g., "NY-ESO-$1_{125\text{-}133}$."

In certain embodiments, the epitope is complexed with an HLA class I molecule. In some embodiments, the HLA class 1 molecule is selected from an HLA-A, HLA-B, and HLA-C allele. In some embodiments, the HLA class 1 molecule is selected from an HLA-E, HLA-F, and HLA-G allele. In certain embodiments, the HLA class 1 molecule is an HLA-A allele. In certain embodiments, the HLA class 1 molecule is an HLA-B allele. In certain embodiments, the HLA class 1 molecule is an HLA-C allele.

Many HLA-A, HLA-B, and HLA-C alleles are known in the art, and any of the known alleles can be used in the present disclosure. An updated list of HLA alleles is available at hla.alleles.org/(last visited on Feb. 27, 2019). In some embodiments, the HLA class 1 molecule is an HLA-B allele selected from an HLA-B*07, an HLA-B*08, an HLA-B*13, an HLA-B*14, an HLA-B*15, an HLA-B*18, an HLA-B*27, an HLA-B*35, an HLA-B*37, an HLA-B*38, an HLA-B*39, an HLA-B*40, an HLA-B*41, an HLA-B*42, an HLA-B*44, an HLA-B*45, an HLA-B*46, an HLA-B*47, an HLA-B*48, an HLA-B*49, an HLA-B*50, an HLA-B*51, an HLA-B*52, an HLA-B*53, an HLA-B*54, an HLA-B*55, an HLA-B*56, an HLA-B*57, an HLA-B*58, an HLA-B*59, an HLA-B*67, an HLA-B*73, an HLA-B*78, an HLA-B*79, an HLA-B*81, an HLA-B*82, and an HLA-B*83. In certain embodiments, the HLA-B allele is an HLA-B*40:01 allele. In certain embodiments, the HLA-B allele is an HLA-B*40:02 allele. In certain embodiments, the HLA-B allele is an HLA-B*40:03 allele. In certain embodiments, the HLA-B allele is an HLA-B*40:04 allele. In certain embodiments, the HLA-B allele is an HLA-B*40:05 allele. In certain embodiments, the HLA-B allele is an HLA-B*40:06 allele.

In certain embodiments, the HLA class 1 molecule is an HLA-B allele selected from the group consisting of HLA-B*40:01:01, HLA-B*40:01:02:01, HLA-B*40:01:02:02, HLA-B*40:01:02:03, HLA-B*40:01:02:04, HLA-B*40:01:02:05, HLA-B*40:01:02:06, HLA-B*40:01:02:07, HLA-B*40:01:02:08, HLA-B*40:01:02:09, HLA-B*40:01:03, HLA-B*40:01:04, HLA-B*40:01:05, HLA-B*40:01:06, HLA-B*40:01:07, HLA-B*40:01:08, HLA-B*40:01:09, HLA-B*40:01:10, HLA-B*40:01:11, HLA-B*40:01:12, HLA-B*40:01:13, HLA-B*40:01:14, HLA-B*40:01:15, HLA-B*40:01:16, HLA-B*40:01:17, HLA-B*40:01:18, HLA-B*40:01:19, HLA-B*40:01:20, HLA-B*40:01:21, HLA-B*40:01:22, HLA-B*40:01:23, HLA-B*40:01:24, HLA-B*40:01:25, HLA-B*40:01:26, HLA-B*40:01:27, HLA-B*40:01:28, HLA-B*40:01:29, HLA-B*40:01:30, HLA-B*40:01:31, HLA-B*40:01:32, HLA-B*40:01:33, HLA-B*40:01:34, HLA-B*40:01:35, HLA-B*40:01:36, HLA-B*40:01:37, HLA-B*40:01:38, HLA-B*40:01:39, HLA-B*40:01:40, HLA-B*40:01:41, HLA-B*40:01:42, HLA-B*40:01:43, HLA-B*40:01:44, HLA-B*40:01:45, HLA-B*40:01:46, HLA-B*40:01:47, HLA-B*40:01:48, HLA-B*40:01:49, HLA-B*40:01:50, HLA-B*40:01:51, HLA-B*40:01:52, HLA-B*40:01:53, HLA-B*40:01:54, HLA-B*40:01:55, HLA-B*40:01:56, HLA-HLA-B*40:01:58, HLA-B*40:01:59, HLA-B*40:01:60, HLA-B*40:01:57, B*40:02:01:01, HLA-B*40:02:01:02, HLA-B*40:02:01:03, HLA-B*40:02:01:04, HLA-B*40:02:01:05, HLA-B*40:02:01:06, HLA-B*40:02:01:07, HLA-B*40:02:01:08, HLA-B*40:02:02, HLA-B*40:02:03, HLA-B*40:02:04, HLA-B*40:02:05, HLA-B*40:02:06, HLA-B*40:02:07, HLA-B*40:02:08, HLA-B*40:02:09, HLA-B*40:02:10, HLA-B*40:02:11, HLA-B*40:02:12, HLA-B*40:02:13, HLA-B*40:02:14, HLA-B*40:02:15, HLA-B*40:02:16, HLA-B*40:02:17, HLA-B*40:02:18, HLA-B*40:02:19, HLA-B*40:02:20, HLA-B*40:02:21, HLA-B*40:02:22, HLA-B*40:02:23, HLA-B*40:02:24, HLA-B*40:02:25, HLA-B*40:02:26, HLA-B*40:03:01:01, HLA-B*40:03:01:02, HLA-B*40:04:01, HLA-B*40:04:02, HLA-B*40:05:01:01, HLA-B*40:05:01:02, HLA-B*40:06:01:01, HLA-B*40:06:01:02, HLA-B*40:06:02, HLA-B*40:06:03, HLA-B*40:06:04:01, HLA-B*40:06:04:02, HLA-B*40:06:05, HLA-B*40:06:06, HLA-B*40:06:07, HLA-B*40:06:08, HLA-B*40:06:09, HLA-B*40:06:10, HLA-B*40:06:11, HLA-B*40:06:12, HLA-B*40:06:13, HLA-B*40:06:14, HLA-B*40:06:15, HLA-B*40:06:16, HLA-B*40:06:17, HLA-B*40:06:18, HLA-B*40:07, HLA-B*40:08, HLA-B*40:09, HLA-B*40:100, HLA-B*40:101, HLA-B*40:102, HLA-B*40:103, HLA-B*40:104, HLA-B*40:105, HLA-B*40:106, HLA-B*40:107, HLA-B*40:108, HLA-B*40:109, HLA-B*40:10:01:01, HLA-B*40:10:01:02, HLA-B*40:10:02, HLA-B*40:110, HLA-B*40:111, HLA-B*40:112, HLA-B*40:113, HLA-B*40:114:01, HLA-B*40:114:02, HLA-B*40:115, HLA-B*40:116, HLA-B*40:117, HLA-B*40:118, HLA-B*40:119, HLA-B*40:11:01, HLA-B*40:11:02, HLA-B*40:12, HLA-B*40:120, HLA-B*40:121, HLA-B*40:122, HLA-B*40:123, HLA-B*40:124:01, HLA-B*40:124:02, HLA-B*40:125:01, HLA-B*40:125:02, HLA-B*40:126, HLA-B*40:127, HLA-B*40:128, HLA-B*40:129, HLA-B*40:13, HLA-B*40:130:01, HLA-B*40:130:02, HLA-B*40:131, HLA-B*40:132, HLA-B*40:133, HLA-B*40:134, HLA-B*40:135, HLA-B*40:136, HLA-B*40:137, HLA-B*40:138, HLA-B*40:139, HLA-B*40:140, HLA-B*40:141, HLA-B*40:142, HLA-B*40:143, HLA-B*40:144, HLA-B*40:145, HLA-B*40:146, HLA-B*40:147, HLA-B*40:148, HLA-B*40:149, HLA-B*40:14:01, HLA-B*40:14:02, HLA-B*40:14:03, HLA-B*40:15, HLA-B*40:150, HLA-B*40:151, HLA-B*40:152, HLA-B*40:153, HLA-B*40:154, HLA-B*40:155:01, HLA-B*40:155:02, HLA-B*40:156, HLA-B*40:157, HLA-B*40:158, HLA-B*40:159, HLA-B*40:16, HLA-B*40:160:01, HLA-B*40:160:02, HLA-B*40:161, HLA-B*40:162, HLA-B*40:163, HLA-B*40:164, HLA-B*40:165, HLA-B*40:166, HLA-B*40:167, HLA-B*40:168, HLA-B*40:169, HLA-B*40:170, HLA-B*40:171, HLA-B*40:172, HLA-B*40:173, HLA-B*40:174, HLA-B*40:175, HLA-B*40:176, HLA-B*40:177, HLA-B*40:178, HLA-B*40:179, HLA-B*40:18, HLA-B*40:180, HLA-B*40:181, HLA-B*40:182, HLA-B*40:183, HLA-B*40:184, HLA-B*40:185, HLA-B*40:186:01, HLA-B*40:186:02, HLA-B*40:187, HLA-B*40:188, HLA-B*40:189, HLA- B*40:19, HLA-B*40:190, HLA-B*40:191, HLA-B*40:192, HLA-B*40:193, HLA-B*40:194, HLA-B*40:195, HLA-B*40:196, HLA-B*40:197, HLA-B*40:198, HLA-B*40:199, HLA-B*40:200, HLA-B*40:201, HLA-B*40:202, HLA-B*40:203, HLA-B*40:204, HLA-B*40:205, HLA-B*40:206, HLA-B*40:207, HLA-B*40:208, HLA-B*40:209, HLA-B*40:20:01:01, HLA-B*40:20:01:02, HLA-B*40:21, HLA-B*40:210, HLA-B*40:211, HLA-B*40:212, HLA-B*40:213, HLA-B*40:214, HLA-B*40:215, HLA-B*40:216, HLA-B*40:217, HLA-B*40:218, HLA-B*40:219, HLA-B*40:220, HLA-B*40:221, HLA-B*40:222, HLA-B*40:223, HLA-B*40:224, HLA-B*40:225, HLA-B*40:226, HLA-B*40:227, HLA-B*40:228, HLA-B*40:229, HLA-B*40:22 57, HLA-B*40:23, HLA-B*40:230, HLA-B*40:231, HLA-B*40:232, HLA-B*40:233, HLA-B*40:234, HLA-B*40:235, HLA-B*40:236, HLA-B*40:237, HLA-B*40:238, HLA-B*40:239, HLA-B*40:24, HLA-B*40:240, HLA-B*40:241, HLA-B*40:242, HLA-B*40:243, HLA-B*40:244, HLA-B*40:245, HLA-B*40:246, HLA-B*40:247, HLA-B*40:248, HLA-B*40:249, HLA-B*40:25, HLA-B*40:250, HLA-B*40:251, HLA-B*40:252, HLA-B*40:253, HLA-B*40:254, HLA-B*40:255, HLA-B*40:256, HLA-B*40:257, HLA-B*40:258, HLA-B*40:259, HLA-B*40:26, HLA-B*40:260, HLA-B*40:261, HLA-B*40:262, HLA-B*40:263, HLA-B*40:264, HLA-B*40:265, HLA-B*40:266, HLA-B*40:267, HLA-B*40:268, HLA-B*40:269, HLA-B*40:270, HLA-B*40:271, HLA-B*40:272, HLA-B*40:273, HLA-B*40:274, HLA-B*40:275, HLA-B*40:276, HLA-B*40:277, HLA-B*40:278, HLA-B*40:279, HLA-B*40:27:01, HLA-B*40:27:02, HLA-B*40:28, HLA-B*40:280, HLA-B*40:281, HLA-B*40:282, HLA-B*40:283, HLA-B*40:284, HLA-B*40:285, HLA-B*40:286, HLA-B*40:287, HLA-B*40:288, HLA-B*40:289, HLA-B*40:29, HLA-B*40:290, HLA-B*40:291, HLA-B*40:292, HLA-B*40:293, HLA-B*40:294, HLA-B*40:295, HLA-B*40:296, HLA-B*40:297, HLA-B*40:298:01, HLA-B*40:298:02, HLA-B*40:299, HLA-B*40:30, HLA-B*40:300, HLA-B*40:301, HLA-B*40:302, HLA-B*40:303, HLA-B*40:304, HLA-B*40:305, HLA-B*40:306, HLA-B*40:307, HLA-B*40:308, HLA-B*40:309, HLA-B*40:31, HLA-B*40:310, HLA-B*40:311, HLA-B*40:312, HLA-B*40:313, HLA-B*40:314, HLA-B*40:315, HLA-B*40:316, HLA-B*40:317, HLA-B*40:318, HLA-B*40:319, HLA-B*40:32, HLA-B*40:320, HLA-B*40:321, HLA-B*40:322, HLA-B*40:323, HLA-B*40:324, HLA-B*40:325, HLA-B*40:326, HLA-B*40:327, HLA-B*40:328, HLA-B*40:329, HLA-B*40:33, HLA-B*40:330, HLA-B*40:331, HLA-B*40:332, HLA-B*40:333, HLA-B*40:334, HLA-B*40:335, HLA-B*40:336, HLA-B*40:337 98, HLA-B*40:338, HLA-B*40:339, HLA-B*40:34, HLA-B*40:340, HLA-B*40:341, HLA-B*40:342, HLA-B*40:343, HLA-B*40:344, HLA-B*40:345, HLA-B*40:346, HLA-B*40:347, HLA-B*40:348, HLA-B*40:349, HLA-B*40:350, HLA-B*40:351, HLA-B*40:352, HLA-B*40:353, HLA-B*40:354, HLA-B*40:355, HLA-B*40:356, HLA-B*40:357, HLA-B*40:358, HLA-B*40:359, HLA-B*40:35:01, HLA-B*40:35:02, HLA-B*40:36, HLA-B*40:360, HLA-B*40:361 86, HLA-B*40:362, HLA-B*40:363, HLA-B*40:364, HLA-B*40:365, HLA-B*40:366, HLA-B*40:367, HLA-B*40:368, HLA-B*40:369, HLA-B*40:37, HLA-B*40:370, HLA-B*40:371, HLA-B*40:372, HLA-B*40:373, HLA-B*40:374, HLA-B*40:375, HLA-B*40:376, HLA-B*40:377, HLA-B*40:378, HLA-B*40:379, HLA-B*40:38, HLA-B*40:380, HLA-B*40:381, HLA-B*40:382, HLA-B*40:383, HLA-B*40:384, HLA-B*40:385, HLA-B*40:386, HLA-B*40:387, HLA-B*40:388, HLA-B*40:389, HLA-B*40:39, HLA-B*40:390, HLA-B*40:391, HLA-B*40:392, HLA-B*40:393, HLA-B*40:394, HLA-B*40:395, HLA-B*40:396, HLA-B*40:397, HLA-B*40:398, HLA-B*40:399 57, HLA-B*40:40, HLA-B*40:400, HLA-B*40:401, HLA-B*40:402, HLA-B*40:403, HLA-B*40:404, HLA-B*40:406, HLA-B*40:407, HLA-B*40:408, HLA-B*40:409, HLA-B*40:410, HLA-B*40:411, HLA-B*40:412, HLA-B*40:413, HLA-B*40:414, HLA-B*40:42, HLA-B*40:43, HLA-B*40:44, HLA-B*40:45, HLA-B*40:46, HLA-B*40:47, HLA-B*40:48, HLA-B*40:49, HLA-B*40:50, HLA-B*40:51, HLA-B*40:52, HLA-B*40:53, HLA-B*40:54, HLA-B*40:55, HLA-B*40:56, HLA-B*40:57, HLA-B*40:58, HLA-B*40:59, HLA-B*40:60, HLA-B*40:61, HLA-B*40:62, HLA-B*40:63, HLA-B*40:64:01:01, HLA-B*40:64:01:02, HLA-B*40:65, HLA-B*40:66, HLA-B*40:67, HLA-B*40:68, HLA-B*40:69, HLA-B*40:70:01, HLA-B*40:70:02, HLA-B*40:71, HLA-B*40:72:01, HLA-B*40:72:02, HLA-B*40:73, HLA-B*40:74, HLA-B*40:75, HLA-B*40:76, HLA-B*40:77, HLA-B*40:78, HLA-B*40:79, HLA-B*40:80, HLA-B*40:81, HLA-B*40:82, HLA-B*40:83, HLA-B*40:84, HLA-B*40:85, HLA-B*40:86, HLA-B*40:87:01, HLA-B*40:87:02, HLA-B*40:88, HLA-B*40:89, HLA-B*40:90, HLA-B*40:91, HLA-B*40:92, HLA-B*40:93, HLA-B*40:94, HLA-B*40:95, HLA-B*40:96, HLA-B*40:97, HLA-B*40:98, and HLA-B*40:99.

II.B.3. Bispecific T Cell Receptors (TCRs)

Certain aspects of the present disclosure are directed to a bispecific TCR comprising a first antigen-binding domain and a second antigen-binding domain, wherein the first antigen-binding domain comprises a TCR or an antigen-binding portion thereof disclosed herein. In some embodiments, the first antigen-binding domain comprises a single chain variable fragment ("scFv").

In some embodiments, the second antigen-binding domain binds specifically to a protein expressed on the surface of a T cell. Any protein expressed on the surface of a T cell can be targeted by the bispecific antibody disclosed herein. In certain embodiments, the protein expressed on the surface of a T cell is not expressed by other cells. In some embodiments, the protein expressed on the surface of a T cell is expressed on the surface of one or more other human immune cells. In some embodiments, the protein expressed on the surface of a T cell is expressed on the surface of one or more other human immune cells, but it is not expressed on the surface of a human non-immune cell. In some embodiments, the second antigen-binding domain binds specifically to a protein expressed on the surface of a T cell selected from CD3, CD2, CD5, CD6, CD8, CD11a (LFA-1a), CD43, CD45, and CD53. In certain embodiments, the second antigen-binding domain binds specifically to CD3. In some embodiments, the second antigen-binding domain comprises an scFv.

In some embodiments, the first antigen-binding domain and the second antigen-binding domain are linked or associated by a covalent bond. In some embodiments, the first antigen-binding domain and the second antigen-binding domain are linked by a peptide bond.

II.C. Cells Expressing TCRs

Certain aspects of the present disclosure are directed to cells comprising a nucleic acid molecule disclosed herein, a vector disclosed herein, a recombinant TCR disclosed herein, a bispecific TCR disclosed herein, or any combination thereof. Any cell can be used in the present disclosure.

In certain embodiments, the cell expresses CD3. CD3 expression can be naturally occurring, e.g., the CD3 is expressed from a nucleic acid sequence that is endogenously expressed by the cell. For example, T cells and natural killer (NK) cells naturally express CD3. Thus, in some embodiments, the cell is a T cell or a natural killer cell. In certain embodiments, the cell is a T cell selected from a natural killer T (NKT) cell and an innate lymphoid cell (ILC).

In some embodiments, the T cell is isolated from a human subject. In some embodiments, the human subject is the same subject that will ultimately receive the T cell therapy. In other embodiments, the subject is a donor subject, wherein the donor subject is not the same subject that will receive the T cell therapy.

In some embodiments, the cell is a cell that does not naturally express CD3, wherein the cell has been modified to express CD3. In some embodiments, the cell comprises a transgene encoding CD3, wherein the transgene is expressed by the cell. In some embodiments, the cell comprises a transgene encoding a protein that activates expression of endogenous CD3 by the cell. In some embodiments, the cell comprises a transgene encoding a protein or siRNA that inhibits an inhibitor of CD3 expression in the cell. In some embodiments, the transgene is incorporated into the genome of the cell. In some embodiments, the transgene is not incorporated into the genome of the cell.

In some embodiments, the cell that is modified to express CD3 is isolated from a human subject. In some embodiments, the human subject is the same subject that will ultimately receive the cell therapy. In other embodiments, the subject is a donor subject, wherein the donor subject is not the same subject that will receive the cell therapy.

II.D. HLA Class I Molecules

Certain aspects of the present disclosure are directed to a HLA class I molecule complexed to a peptide, wherein the peptide comprises the amino acid sequence set forth in SEQ ID NO: 13. In some embodiments, he peptide consists of the amino acid sequence set forth in SEQ ID NO: 13.

In some embodiments, the HLA Class I molecule is an HLA-A, HLA-B, or an HLA-C. In some embodiments, the HLA Class I molecule is an HLA-E, HLA-F, or HLA-G. In some embodiments, the HLA class 1 molecule is an HLA-B allele selected from an HLA-B*07, an HLA-B*08, an HLA-B*13, an HLA-B*14, an HLA-B*15, an HLA-B*18, an HLA-B*27, an HLA-B*35, an HLA-B*37, an HLA-B*38, an HLA-B*39, an HLA-B*40, an HLA-B*41, an HLA-B*42, an HLA-B*44, an HLA-B*45, an HLA-B*46, an HLA-B*47, an HLA-B*48, an HLA-B*49, an HLA-B*50, an HLA-B*51, an HLA-B*52, an HLA-B*53, an HLA-B*54, an HLA-B*55, an HLA-B*56, an HLA-B*57, an HLA-B*58, an HLA-B*59, an HLA-B*67, an HLA-B*73, an HLA-B*78, an HLA-B*79, an HLA-B*81, an HLA-B*82, and an HLA-B*83. In certain embodiments, the HLA-B allele is an HLA-B*40:01 allele. In certain embodiments, the HLA-B allele is an HLA-B*40:02 allele. In certain embodiments, the HLA-B allele is an HLA-B*40:03 allele. In certain embodiments, the HLA-B allele is an HLA-B*40:04 allele. In certain embodiments, the HLA-B allele is an HLA-B*40:05 allele. In certain embodiments, the HLA-B allele is an HLA-B*40:06 allele. In some embodiments, the HLA allele is any HLA allele disclosed herein, e.g., supra.

In some embodiments, the HLA Class I molecule comprises an alpha chain and a B2m. In some embodiments, the alpha chain comprises an a1 domain, an a2 domain, an a3 domain. In some embodiments, the β2m comprises an amino acid sequence having at least about 80%, at least about 85%, at least about 90%, at least about 95%, at least about 96%, at least about 97% at least about 98%, at least about 99%, or about 100% sequence identity with the amino acid sequence set forth in SEQ ID NO: 16. In some embodiments, the sequence of the alpha chain is selected from any of the HLA protein sequences available at hla.alleles.org (last visited Feb. 27, 2019).

In some embodiments, the HLA class I molecule is a monomer. In some embodiments, the HLA class I molecule is a dimer. In some embodiments, the HLA class I molecule is a multimer. In some embodiments, the HLA class I molecule is a trimer. In some embodiments, the HLA class I molecule is a tetramer. In some embodiments, the HLA class I molecule is a pentamer.

Certain aspects of the present disclosure are directed to antigen presenting cells (APCs) comprising any HLA class I molecule disclosed herein. In certain embodiments, the APC expressed the HLA class I molecule on the surface of the APC. In certain embodiments, the APC comprises more than one HLA class I molecule disclosed herein.

II.D. Vaccines

Certain aspects of the present disclosure a cancer vaccine comprising a peptide comprising an amino acid sequence as set forth in SEQ ID NO: 13. In some embodiments, the cancer vaccine comprises a peptide that consists of the amino acid sequence set forth in SEQ ID NO: 13. In some embodiments, the vaccine further comprises one or more excipient. In some embodiments, the vaccine further comprises one or more additional peptides. In some embodiments, the one or more additional peptides comprise one or more additional epitopes.

III. Methods of the Disclosure

Certain aspects of the present disclosure are directed to methods of treating a cancer in a subject in need thereof. Other aspects of the present disclosure are directed to Naoto HIRANO-49-Substitute Specification application Ser. No. 17/436,931 Clean Version methods of engineering an antigen-targeting cell. Other aspects of the present disclosure are directed to methods of enriching a target population of T cells obtained from a human subject.

III.A. Methods of Treating Cancer

Certain aspects of the present disclosure are directed to methods of treating a cancer in a subject in need thereof, comprising administering to the subject a nucleic acid molecule disclosed herein, a recombinant TCR disclosed herein, a bispecific TCR disclosed herein, an epitope disclosed herein, or an HLA class I molecule disclosed herein, or a vector or cell comprising any of the above.

In some embodiments, the cancer is selected from melanoma, bone cancer, renal cancer, prostate cancer, breast cancer, colon cancer, lung cancer, cutaneous or intraocular malignant melanoma, pancreatic cancer, skin cancer, cancer of the head or neck, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia (AML), chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, other B cell malignancies, and combinations of said cancers. In some embodiments, the cancer melanoma.

In some embodiments, the cancer is relapsed. In some embodiments, the cancer is refractory. In some embodiments, the cancer is advanced. In some embodiments, the cancer is metastatic.

In some embodiments, the methods disclosed herein treat a cancer in a subject. In some embodiments, the methods disclosed herein reduce the severity of one or more symptom of the cancer. In some embodiments, the methods disclosed herein reduce the size or number of a tumor derived from the cancer. In some embodiments, the methods disclosed herein increase the overall survival of the subject, relative to a subject not provided the methods disclosed herein. In some embodiments, the methods disclosed herein increase the progressive-free survival of the subject, relative to a subject not provided the methods disclosed herein. In some embodiments, the methods disclosed herein lead to a partial response in the subject. In some embodiments, the methods disclosed herein lead to a complete response in the subject.

In some embodiments, the methods disclosed herein comprise treating a cancer in a subject in need thereof, comprising administering to the subject a cell described herein, wherein the cell comprises a nucleic acid molecule disclosed herein, a vector disclosed herein, a recombinant TCR disclosed herein, and/or a bispecific antibody disclosed herein. In some embodiments, the cell is a T cell. In some embodiments, the cell is a cell that is modified to express CD3.

In some embodiments, the cell, e.g., a T cell, is obtained from the subject. In some embodiments, the cell, e.g., a T cell, is obtained from a donor other than the subject.

In some embodiments, the subject is preconditioned prior to administering the cells. The preconditioning can comprise any substance that promotes T cell function and/or survival. In some embodiments, the preconditioning comprises administering to the subject a chemotherapy, a cytokine, a protein, a small molecule, or any combination thereof. In some embodiments, the preconditioning comprises administering an interleukin. In some embodiments, the preconditioning comprises administering IL-2, IL-4, IL-7, IL-9, IL-15, IL-21, or any combination thereof. In some embodiments, the preconditioning comprises administering cyclophosphamide, fludarabine, or both. In some embodiments, the preconditioning comprises administering vitamin C, an AKT inhibitor, ATRA (vesanoid, tretinoin), rapamycin, or any combination thereof.

III.B. Methods of Engineering an Antigen-Targeting Cell

Certain aspects of the present disclosure are directed to methods of engineering an antigen-targeting cell. In some embodiments, the antigen is an NY-ESO-1 antigen. In some embodiments, the method comprises transducing a cell with a nucleic acid molecule disclosed herein or a vector disclosed herein. The cell can be any cell described herein. In some embodiments, the cell is a T cell described herein. In some embodiments, the cell is a cell that is modified to express CD3, as described herein. In some embodiments, the cell, e.g., the T cell, is obtained from a subject in need of a T cell therapy. In some embodiments, the cell is obtained from a donor other than the subject in need of the T cell therapy. In some embodiments, the cell is a T cell or a natural killer cell.

III.C. Methods of Enriching a Target Population of T Cells

Certain aspects of the present disclosure are directed to methods of enriching a target population of T cells obtained from a human subject. In some embodiments, the method comprises contacting the T cells with an HLA class I molecule disclosed herein. In some embodiments, the method comprises contacting the T cells with an APC disclosed herein. In some embodiments, following the contacting, the enriched population of T cells comprises a higher number of T cells capable of binding the HLA class I molecule relative to the number of T cells capable of binding the HLA class I molecule prior to the contacting.

In some embodiments, the method comprises contacting the T cells in vitro with a peptide, wherein the peptide comprises the amino acid sequence set forth in SEQ ID NO: 13. In some embodiments, the method comprises contacting the T cells in vitro with a peptide, wherein the peptide consists of the amino acid sequence set forth in SEQ ID NO: 13. In some embodiments, following the contacting, the enriched population of T cells comprises a higher number of T cells capable of binding the HLA class I molecule relative to the number of T cells capable of binding the HLA class I molecule prior to the contacting.

Some aspects of the present disclosure are directed to a method of selecting a T cell capable of targeting a tumor cell. In some embodiments, the method comprises contacting a population of isolated T cells in vitro with a peptide, wherein the peptide consists of an amino acid sequence as set forth in SEQ ID NO: 13. In some embodiments, the T cells are obtained from a human subject.

The T cells obtained from the human subject can be any T cells disclosed herein. In some embodiments, the T cells obtained from the human subject are tumor infiltrating lymphocytes (TIL).

In some embodiments, the method further comprises administering to the human subject the enriched T cells. In some embodiments, the subject is preconditioned prior to receiving the T cells, as described herein.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference.

Having generally described this disclosure, a further understanding can be obtained by reference to the examples provided herein. These examples are for purposes of illustration only and are not intended to be limiting.

EXAMPLES

Example 1

TILs were isolated from a metastatic melanoma patient, then polyclonally expanded in vitro, and their NY-ESO-1 antigen specificity for HLA-B*40:01 allele was examined. The combination of structure-based analysis using peptide/HLA (pHLA) multimers and functional analysis has been used to measure antigen-specific T cell responses.

Figure 2:
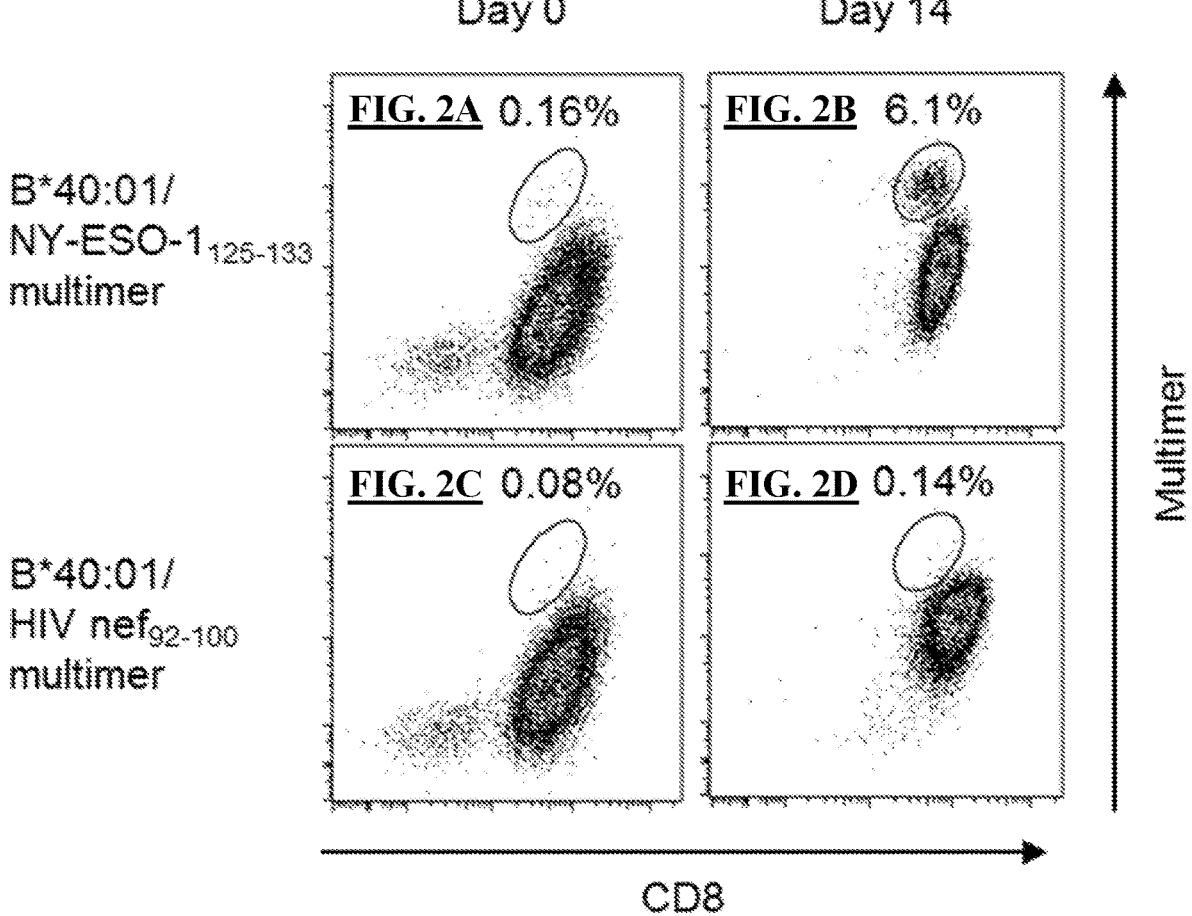
FIGS. 2A-2D are graphical representations of B*40:01/NY-ESO-1$_{125-133}$ multimer staining of melanoma TILs. The TILs were stimulated once with B*40:01-artificial APCs pulsed with the NY-ESO-1$_{125}$EFTVSGNIL$_{133}$ peptide. Data on B*40:01/NY-ESO-1$_{125-133}$ (FIGS. 2A-2B) or control B*40:01/HIV nef$_{92-100}$ (FIGS. 2C-2D) multimer staining before stimulation (day 0.
Figure 3:
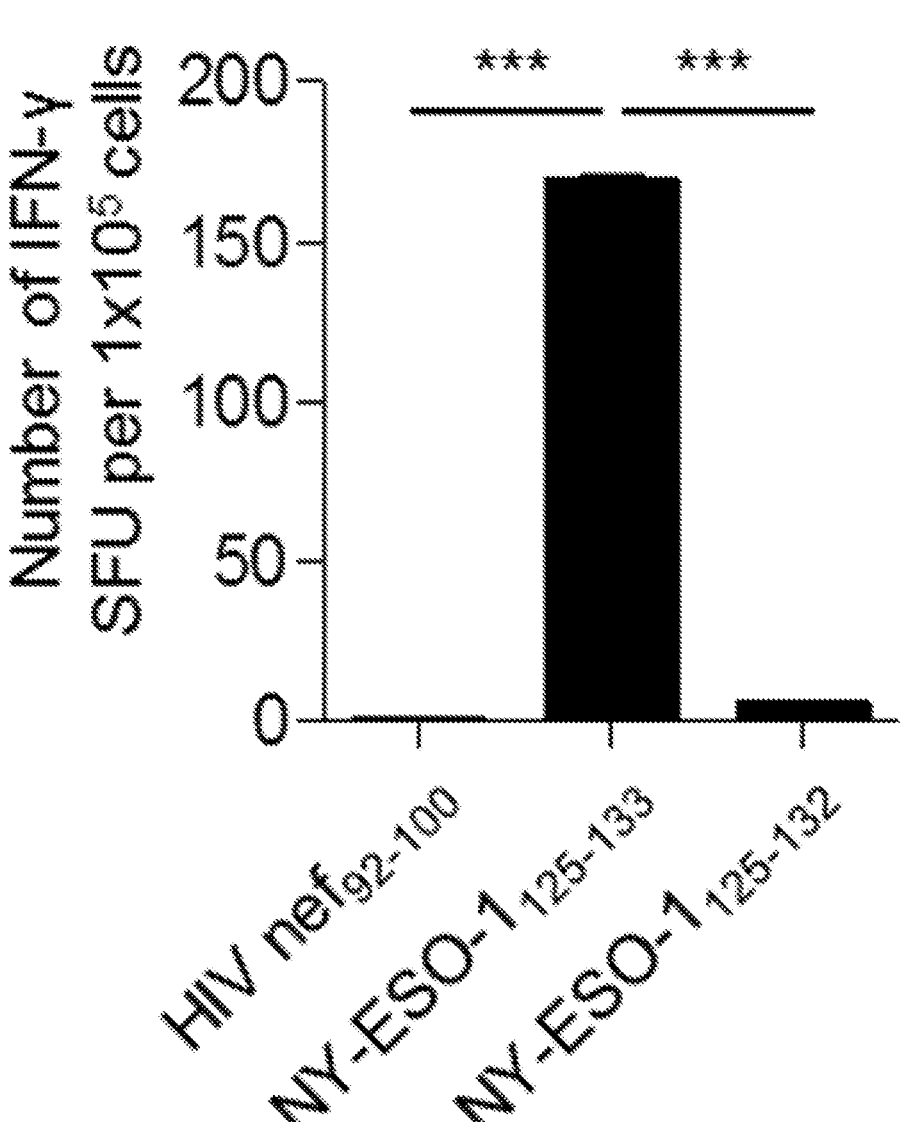
FIG. 3 is a bar graph illustrating the functional assessment of B*40:01/NY-ESO-1$_{125-133}$ multimer-positive melanoma TILs. IFN-γ production by the TILs in a B*40:01/NY-ESO-1$_{125-133}$-specific manner following one peptide-specific stimulation. The TILs stimulated once with B*40:01-artificial APCs pulsed with the NY-ESO-1$_{125-133}$ peptide were employed as responder cells in IFN-γ ELISPOT analysis. B*40:01-artificial APCs pulsed with the indicated peptides were used as stimulator cells. The HIV nef$_{92-100}$ and NY-ESO-1$_{125-132}$ peptides were employed as controls. Experiments were carried out in triplicate, and error bars depict SD. ***P<0.001.

Since pHLA multimer production requires the use of a peptide with a known exact sequence, it is not straightforward or practical to conduct high-throughput screening for new epitope peptides using a pHLA multimer-based strategy. In addition to structure-based analysis using pHLA multimers, functional analysis can be applied to determine the antigen specificity of T cells. We conducted functional assays using artificial antigen-presenting cells (APCs), which can take up and process longer peptides and present epitope peptides via class I molecules, as stimulator cells. B*40:01-artificial APCs were pulsed with overlapping peptides to cover the whole protein of NY-ESO-1 (Table 5) and used as stimulators in cytokine ELISPOT assays. Following one controlled stimulation with B*40:01-artificial APCs pulsed with the NY-ESO-1-derived overlapping peptides, B*40:01 melanoma TILs showed positive responses to two adjacent peptides with the shared sequence $_{121}$VLLKEFTVSGNILTI135 (SEQ ID NO: 63) in the IFN-$\gamma$ ELISPOT analysis (FIG. 1). Using a series of mutant deletion peptides, we determined the minimally required peptide epitope, $_{125}$EFTVSGNIL$_{133}$ (SEQ ID NO: 13) presented by B*40:01 molecules. We identified HLA-B*40:01/NY-ESO-1$_{125-133}$ T cells, which accounted for 0.16% of CD8 T cells among the polyclonally expanded TILs (FIG. 2). Following one controlled peptide-specific stimulation with B*40:01-artificial APCs, the frequency of B*40:01/NY-ESO-1$_{125-133}$ T cells increased to 6.1%, excluding the possibility that the low percentage of staining represented false positivity (FIG. 2). The multimer-positive T cells secreted detectable IFN-$\gamma$ in an HLA-restricted peptide-specific manner according to ELISPOT analysis (FIG. 3).

TABLE 5

NY-ESO-1 Overlapping Peptides.

| Position | Peptide sequence | SEQ ID NO |
|---|---|---|
| 1 | MQAEGRGTGGSTGDADGPGG | 19 |
| 6 | RGTGGSTGDADGPGGPGIPD | 20 |
| 11 | STGDADGPGGPGIPDGPGGN | 21 |
| 16 | DGPGGPGIPDGPGGNAGGPG | 22 |
| 21 | PGIPDGPGGNAGGPGEAGAT | 23 |
| 26 | GPGGNAGGPGEAGATGGRGP | 24 |
| 31 | AGGPGEAGATGGRGPRGAGA | 25 |
| 36 | EAGATGGRGPRGAGAARASG | 26 |
| 41 | GGRGPRGAGAARASGPGGGA | 27 |
| 46 | RGAGAARASGPGGGAPRGPH | 28 |
| 51 | ARASGPGGGAPRGPHGGAAS | 29 |
| 56 | PGGGAPRGPHGGAASGLNGC | 30 |
| 61 | PRGPHGGAASGLNGCCRCGA | 31 |
| 66 | GGAASGLNGCCRCGARGPES | 32 |
| 71 | GLNGCCRCGARGPESRLLEF | 33 |
| 76 | CRCGARGPESRLLEFYLAMP | 34 |
| 81 | RGPESRLLEFYLAMPFATPM | 35 |
| 86 | RLLEFYLAMPFATPMEAELA | 36 |
| 91 | YLAMPFATPMEAELARRSLA | 37 |
| 96 | FATPMEAELARRSLAQDAPP | 38 |
| 101 | EAELARRSLAQDAPPLPVPG | 39 |

TABLE 5-continued

NY-ESO-1 Overlapping Peptides.

| Position | Peptide sequence | SEQ ID NO |
|---|---|---|
| 106 | RRSLAQDAPPLPVPGVLLKE | 40 |
| 111 | QDAPPLPVPGVLLKEFTVSG | 41 |
| 116 | LPVPGVLLKEFTVSGNILTI | 42 |
| 121 | VLLKEFTVSGNILTIRLTAA | 43 |
| 126 | FTVSGNILTIRLTAADHRQL | 44 |
| 131 | NILTIRLTAADHRQLQLSIS | 45 |
| 136 | RLTAADHRQLQLSISSCLQQ | 46 |
| 141 | DHRQLQLSISSCLQQLSLLM | 47 |
| 146 | QLSISSCLQQLSLLMWITQC | 48 |
| 151 | SCLQQLSLLMWITQCFLPVF | 49 |
| 156 | LSLLMWITQCFLPVFLAQPP | 50 |
| 161 | WITQCFLPVFLAQPPSGQRR | 51 |

Figure 4:
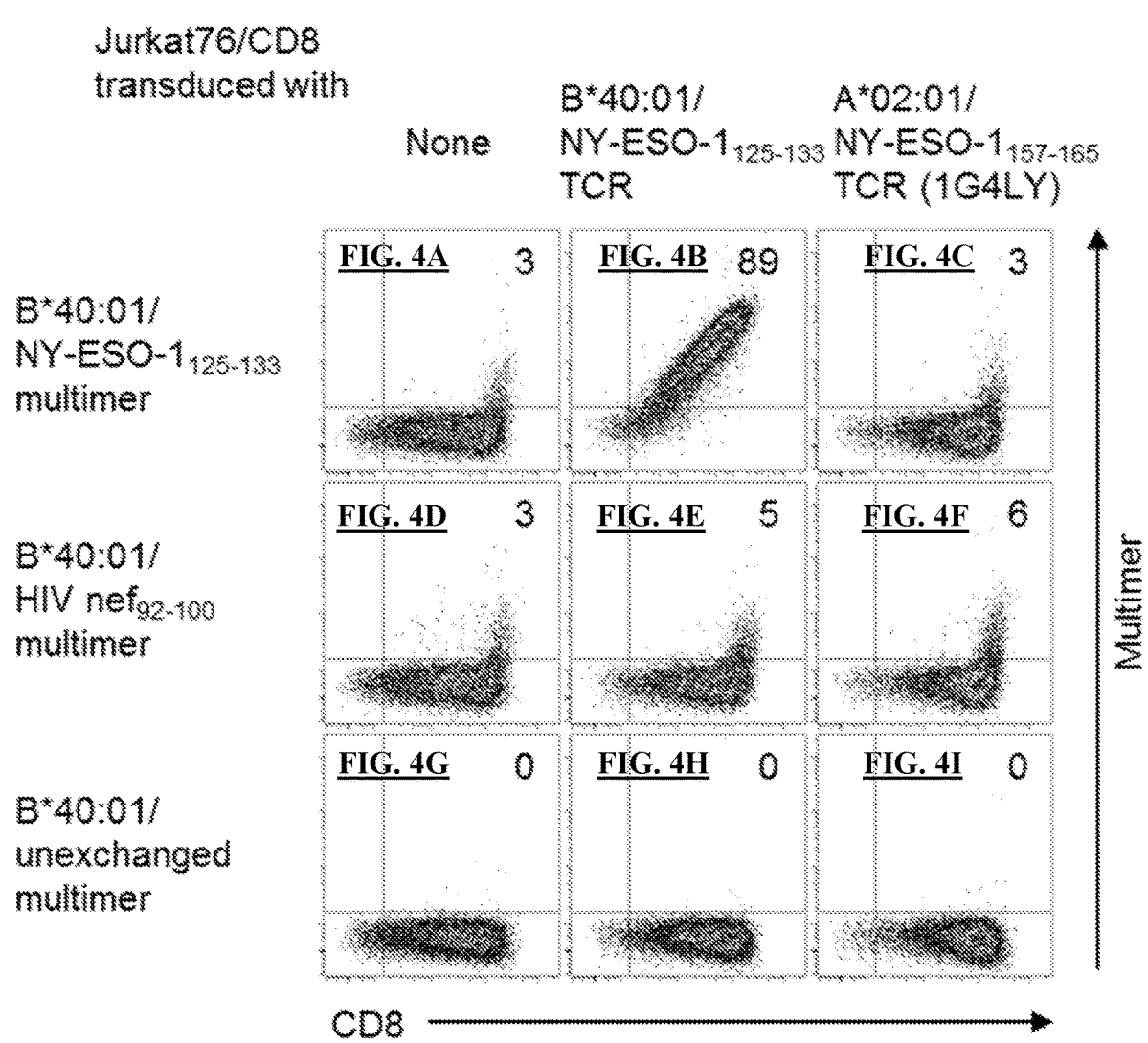
FIGS. 4A-4I are graphical representations of positive staining of Jurkat 76/CD8 cells transduced with B*40:01/NY-ESO-1$_{125-133}$ TCR genes with a cognate multimer. Jurkat 76/CD8 cells transduced with the B*40:01/NY-ESO-1$_{125-133}$ TCR (FIGS. 4B, 4E, and 4H) were stained with the B*40:01/NY-ESO-1$_{125-133}$ multimer (FIG. 4B).
Figure 5:
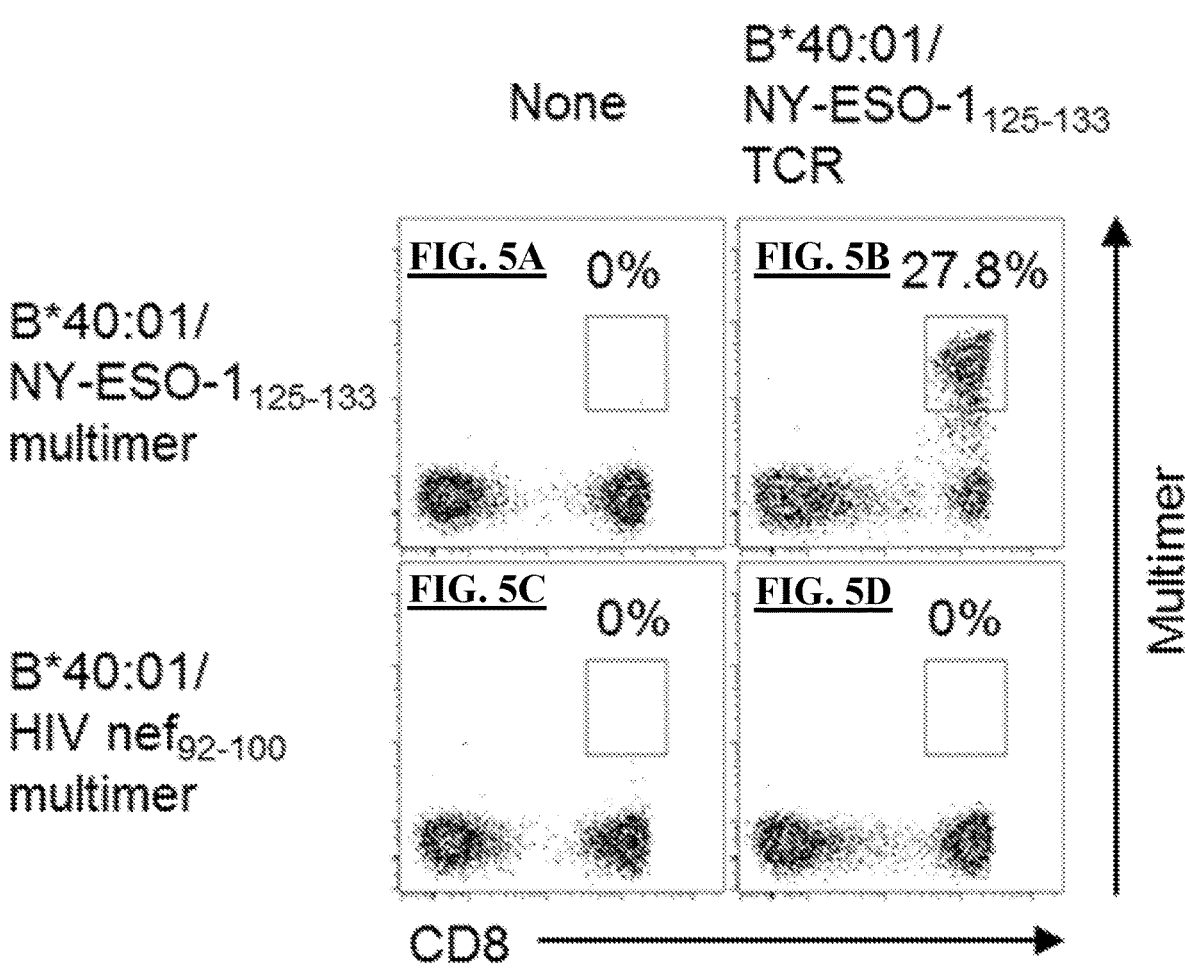
FIGS. 5A-5D are graphical representations of positive staining of human primary T cells transduced with B*40:01/NY-ESO-1$_{125-133}$ TCR genes (FIGS. 5B and 5D) with a cognate multimer. Primary T cells transduced with the B*40:01/NY-ESO-1$_{125-133}$ TCR were stained with the B*40:01/NY-ESO-1$_{125-133}$ (FIG. 5B) or B*40:01/HIV nef$_{92-100}$ control multimer (FIG. 5D). Untransduced primary T cells were employed as negative controls (FIGS. 5A and 5C). The percentage of multimer CD8 T cells is shown.
Figure 6:
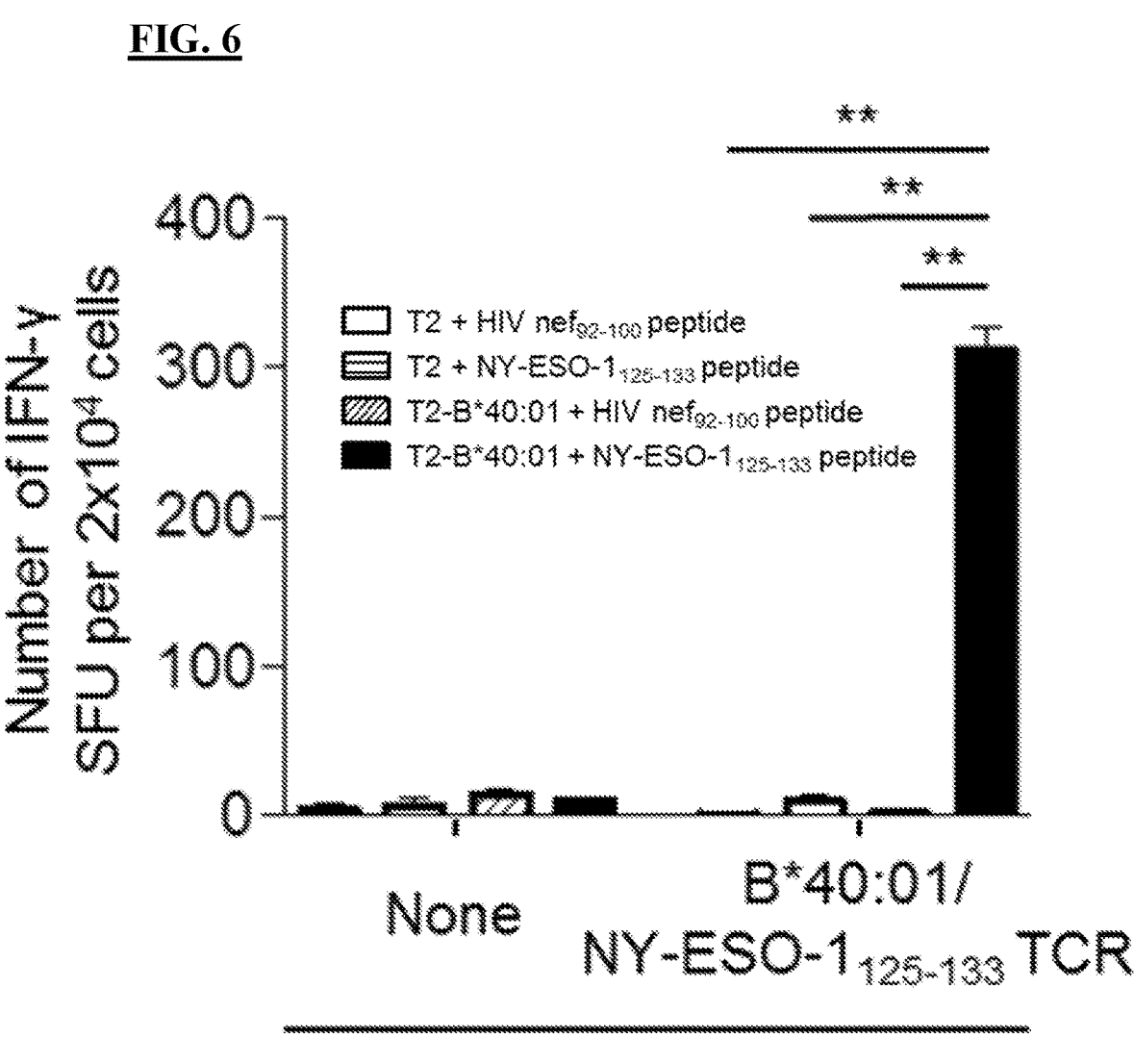
FIG. 6 is a bar graph illustrating that human primary T cells transduced with B*40:01/NY-ESO-1$_{125-133}$ TCR genes react strongly with the cognate peptide presented by the target class I molecule. Primary T cells transduced with B*40:01/NY-ESO-1$_{125-133}$ TCR genes or untransduced primary T cells were used as responder cells in IFN-γ ELISPOT analysis. HLA-B*40:01-transduced T2 cells (T2-B*40:01) were generated. T2 or T2-B*40:01 cells pulsed with the NY-ESO-1$_{125-133}$ or HIV nef$_{92-100}$ peptide (control) were used as stimulator cells. Experiments were carried out in triplicate, and error bars depict SD. **P<0.01.
Figures 7A, 7B:
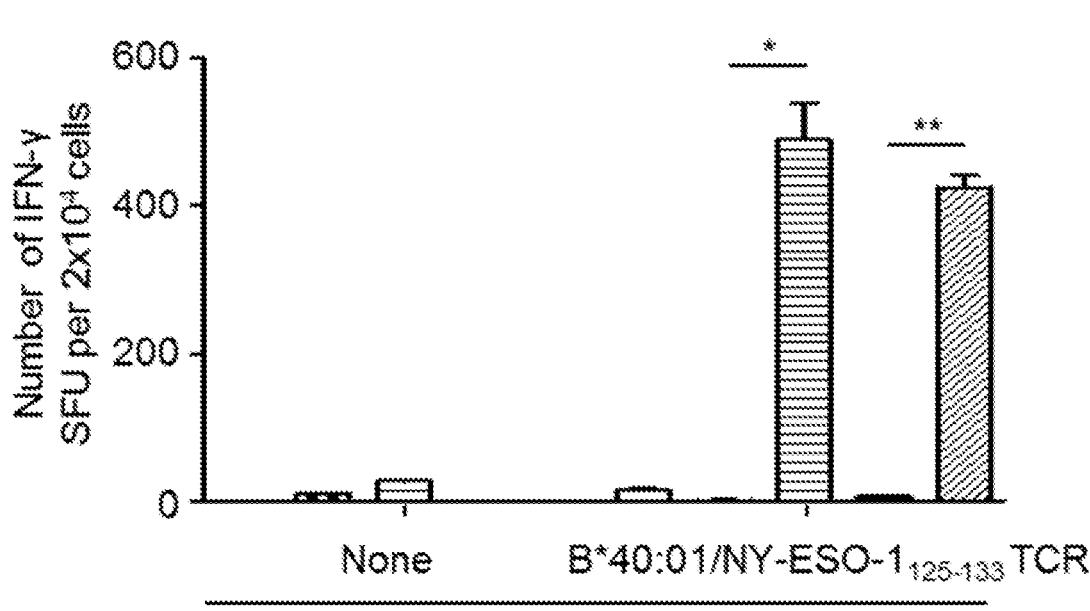
FIGS. 7A and 7B are a graphical representation of illustrating that primary T cells transduced with B*40:01/NY-ESO-1$_{125-133}$ TCR genes recognize tumor cells (FIG. 7B) and its legend (FIG. 7B). Primary T cells transduced with B*40:01/NY-ESO-1$_{125-133}$ TCR genes or untransduced primary T cells were employed as responder cells in IFN-γ ELISPOT analysis. SK-MEL-21, A375, and SK-MEL-28 cells that were either untransduced or transduced with HLA-B*40:01 or NY-ESO-1, as indicated in FIG. 7B (legend for FIG. 7A), were employed as stimulator cells. Experiments were carried out in triplicate, and error bars depict SD. *P<0.05, **P<0.01.
Figures 8A, 8B, 8C, 8D:
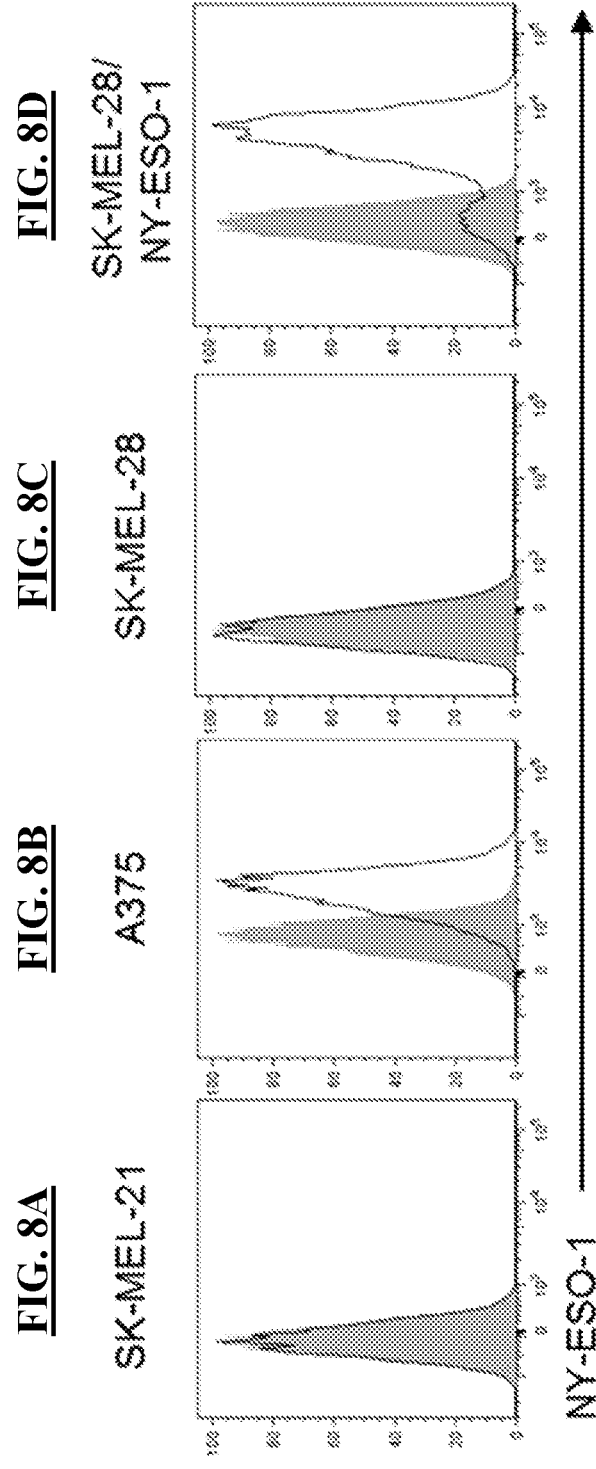
FIGS. 8A-8D are graphical representations of the expression of NY-ESO-1 derived from endogenous or transduced full-length gene. The expression of NY-ESO-1 derived from endogenous or transduced full-length gene in target cells was analyzed via intracellular flow cytometry following staining with anti-NY-ESO-1 mAb (open curve) and an isotype control (filled curve).
Figures 9A, 9B:
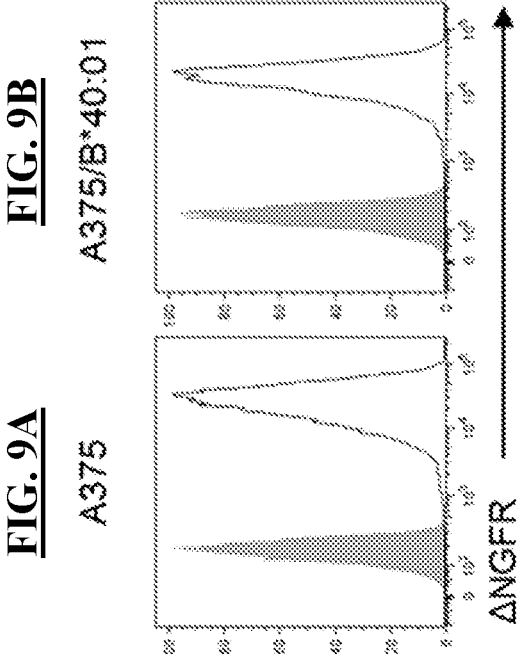
FIGS. 9A-9B are graphical representations of the expression of ANGFR in target cells transduced with the full-length HLA-B*40:01 gene tagged with ANGFR (FIG. 9B). Surface expression of ANGFR in target cells transduced with the full-length HLA-B*40:01 gene tagged with ANGFR was analyzed by flow cytometry following staining with an anti-NGFR mAb (open curve) and an isotype control (filled curve). ANGFR alone was used as a control (FIG. 9A).

The multimer-positive antitumor T cells were collected and their TCR genes were molecularly cloned (FIG. 4, SEQ ID NOs: 1 and 2). The antigen specificity and functional reactivity of the cloned TCR were verified by multimer staining and ELISPOT assay of TCR-reconstituted T cells. When reconstituted on primary T cells, B*40:01/NY-ESO-$1_{125\text{-}133}$ TCR-transduced T cells were successfully stained with the cognate multimer (FIG. 5) and strongly reacted with the NY-ESO-$1_{125\text{-}133}$ peptide presented by surface B*40:01 molecules (FIG. 6). Importantly, these cells were able to recognize B*40:01-matched and peptide-unpulsed tumor cells naturally expressing the NY-ESO-1 gene. Although A375 melanoma cells are negative for B*40:01, they express the NY-ESO-1 gene endogenously. When B*40:01 molecules were ectopically expressed, they were successfully recognized by B*40:01/NY-ESO-$1_{125\text{-}133}$ TCR-transduced T cells. Moreover, SK-MEL-28 melanoma cells, which lack endogenous expression of NY-ESO-1, became reactive to B*40*01/NY-ESO-$1_{125\text{-}133}$ TCR-transduced T cells when the full-length NY-ESO-1 gene was transduced (FIGS. 7-9). These results clearly demonstrate that the B*40:01/NY-ESO-$1_{125\text{-}133}$ TCR-transduced T cells were sufficiently avid to recognize tumor cells and that the cloned B*40:01/NY-ESO-$1_{125\text{-}133}$ TCR was tumor-reactive.

The use of the newly cloned tumor-reactive B*40:01-restricted NY-ESO-1 TCR genes may widen the applicability of anti-NY-ESO-1 TCR gene therapy beyond HLA-A*02:01-positive cancer patients.

Methods

Cell Samples

Peripheral blood samples were obtained from healthy donors after Institutional Review Board approval. Mononuclear cells were obtained via density gradient centrifugation (Ficoll-Paque PLUS; GE Healthcare). K562 is an erythroleukemic cell line with defective HLA expression. T2 is an HLA-A*02:01$^{+}$ T cell leukemia/B-LCL hybrid cell line. Jurkat 76 is a T cell leukemic cell line lacking TCR and CD8 expression. SK-MEL-21, A375, and SK-MEL-28 are melanoma cell lines. The melanoma cell lines were grown in DMEM supplemented with 10% FBS and 50 µg/ml gentamicin (Invitrogen). The K562, T2, and Jurkat 76 cell lines were cultured in RPMI 1640 supplemented with 10% FBS and 50 µg/ml gentamicin. The K562, T2, A375, and SK-MEL-28 cells were obtained from the American Type Culture Collection (ATCC, Manassas, VA). TILs isolated from a metastatic melanoma patient were grown in vitro.

Peptides

Synthetic peptides were dissolved to 50 µg/ml in DMSO. Peptides used were 20-mer overlapping peptides to cover the whole protein of NY-ESO-1 and B*40:01-restricted NY-ESO-$1_{125\text{-}133}$ (EFTVSGNIL; SEQ ID NO: 13) and HIV nef$_{92\text{-}100}$ (KEKGGLEGL; SEQ ID NO: 62) peptides. The HIV nef$_{92\text{-}100}$ peptide was utilized as a negative control.

Genes

The HLA-B*40:01 gene was fused with a truncated version of the human nerve growth factor receptor (ANGFR) via the internal ribosome entry site. ANGFR-transduced cells were isolated using anti-NGFR monoclonal antibody (mAb). The full-length NY-ESO-1 gene was cloned from Me275 cells via RT-PCR according to the published sequence. TCR genes were cloned by 5'-rapid amplification of cDNA ends (RACE) PCR using a SMARTer RACE cDNA amplification kit (Takara Bio). To clone TCRα genes, for the first round of PCR, cDNA was amplified using a supplied 5'-RACE primer and a 3'-TCRα untranslated region primer (5'-GGAGAGTTCCCTCTGTTTGGAGAG-3'; SEQ ID NO: 57). The second-round PCR was performed using a modified 5'-RACE primer (5'-GTGTGGTGGTACGGGAATT-CAAGCAGTGGTATCAACGCAGAGT-3'; SEQ ID NO: 58) and a 3'-TCRα primer (5'-AC-CACTGTGCTGGCGGCCGCTCAGCTGGAC-CACAGCCGCAGCG-3'; SEQ ID NO: 59). To clone TCRβ genes, for the first round of PCR, cDNA was amplified using a supplied 5'-RACE primer and β C region-specific reverse primers, 3'-Cβ-1 (5'-ATCGTCGAC-CACTGTGCTGGCGGCCGCTCGAGTTCCAGGGCTGC CTTCAGAA ATCC-3'; SEQ ID NO: 60) and 3'-Cβ-2 (5'-GACCACTGTGCTGGCGGCCGCTCGAGCTAGC CTCTGGAATCCTTTCTCTTGAC CATTGC-3'; SEQ ID NO: 61). The second-round PCR was performed using a modified 5'-RACE primer and β C region-specific reverse primers. TCRα and β gene allele names are in accordance with International ImMunoGeneTics Information System unique gene nomenclatures (www.imgt.org). All genes were cloned into the pMX retrovirus vector and transduced using the 293GPG cell-based retrovirus system.

Transfectants

Jurkat 76/CD8 cells were transduced with individual TCRα and TCRβ genes. The Jurkat 76/CD8-derived TCR transfectants were purified (>95% purity) using CD3 Micro-beads (Miltenyi Biotec). The K562-based artificial APCs individually expressing various HLA class I genes as a single HLA allele in conjunction with CD80 and CD83 have been reported previously (Butler and Hirano, *Immunol. Rev.* 257:191-209 (2014); Hirano et al., *Clin. Cancer Res.* 12:2967-75 (2006)). PG13-derived retrovirus supernatants were used to transduce TCR genes into human primary T cells. TransIT293 (Mirus Bio) was used to transfect TCR genes into the 293GPG cell line. NY-ESO-1-SK-MEL-28 cells were retrovirally transduced with the full-length NY-ESO-1 gene to generate SK-MEL-28/NY-ESO-1 cells. The expression of transduced NY-ESO-1 was evaluated by flow cytometry after staining with an anti-NY-ESO-1 mAb (clone DIQ2U; Cell Signaling Technology).

HLA-B*40:01-A375 cells were retrovirally transduced with HLA-B*40:01 to generate A375/B*40:01 cells. HLA-B*40:01 gene were tagged with the ANGFR gene as described above, and the ANGFR cells were purified (>95% purity) and used in subsequent experiments. The ANGFR gene alone was retrovirally transduced as a control.

Flow Cytometry and Cell Sorting

Cell surface molecules were stained with a PC5-conjugated anti-CD8 mAb (clone B9.11; Beckman Coulter), FITC-conjugated anti-NGFR (clone ME20.4; Biolegend), and APC/Cy7-conjugated anti-CD3 (clone UCHT1; Biolegend). Dead cells were discriminated with the LIVE/DEAD Fixable Aqua Dead Cell Stain kit (Life Technologies). For intracellular staining, cells were fixed and permeabilized by using a Cytofix/Cytoperm kit (BD Biosciences). Stained cells were analyzed with flow cytometry (BD Biosciences), and data analysis was performed using FlowJo (Tree Star). Cell sorting was conducted using a FACS Aria II (BD Bioscience).

Cytokine ELISPOT Analysis

IFN-γ ELISPOT assays were conducted as described previously (see, e.g., Kagoya et al., *Nat. Commun.* 9:1915 (2018); Anczurowski et al., *Sci. Rep.* 8:4804 (2018); and Yamashita et al., *Nat Commun.* 8:15244 (2017)). PVDF plates (Millipore, Bedford, MA) were coated with the capture mAb (1-DIK; MABTECH, Mariemont, OH), and T cells were incubated with $2 \times 10^4$ target cells per well in the presence or absence of a peptide for 20-24 hours at 37° C. The plates were subsequently washed and incubated with a biotin-conjugated detection mAb (7-B6-1; MABTECH). HRP-conjugated SA (Jackson ImmunoResearch) was then added, and IFN-γ spots were developed. The reaction was stopped by rinsing thoroughly with cold tap water. ELISPOT plates were scanned and counted using an ImmunoSpot plate reader and ImmunoSpot version 5.0 software (Cellular Technology Limited, Shaker Heights, OH).

Expansion of CD8⁺ TILs in an HLA-Restricted Peptide-Specific Manner

CD8⁺ TILs were purified through negative magnetic selection using the CD8 T Cell Isolation Kit (Miltenyi Biotec). B*40:01-artificial APCs were pulsed with 10 μg/mL NY-ESO-1 peptides for 6 hours. The artificial APCs were then irradiated at 200 Gy, washed, and added to the TILs at an effector to target (E:T) ratio of 20:1. Starting on the next day, 10 IU/ml IL-2 (Novartis), 10 ng/ml IL-15 (Peprotech), and 30 ng/ml IL-21 (Peprotech) were added to the cultures every three days.

Expansion of Primary CD8⁺ T Cells Transduced with the Cloned TOR

CD3⁺ T cells were purified through negative magnetic selection using a Pan T Cell Isolation Kit (Miltenyi Biotec). Purified T cells were stimulated with artificial APC/mOKT3 irradiated with 200 Gy at an E:T ratio of 20:1. Starting on the next day, activated T cells were retrovirally transduced with the cloned TCR genes via centrifugation for 1 hour at 1,000 g at 32° C. for 3 consecutive days. On the following day, 100 IU/ml IL-2 and 10 ng/ml IL-15 were added to the TCR-transduced T cells. The culture medium was replenished every 2-3 days.

Production of Mammalian Cell-Based pHLA Multimers

The affinity-matured HLA class I gene was engineered to carry a Glu (E) residue in lieu of the Gln (Q) residue at position 115 of the α2 domain and a mouse $K^b$ gene-derived α3 domain instead of the HLA class I α3 domain. By fusing the extracellular domain of the affinity-matured HLA class I gene with a Gly-Ser (GS) flexible linker followed by a 6× His tag, we generated the soluble HLA class $I^{Q115E}$-$K^b$ gene. HEK293T cells were individually transduced with various soluble HLA class $I^{Q115E}$-$K^b$ genes along with the B2m gene using the 293GPG cell-based retrovirus system[43]. Stable HEK293T cells ectopically expressing soluble affinity-matured class $I^{Q115E}$-$K^b$ were grown until confluent, and the medium was then changed. Forty-eight hours later, the conditioned medium was harvested and immediately used or frozen until use. The soluble HLA class $I^{Q115E}$-$K^b$-containing supernatant produced by the HEK293T transfectants was incubated with 100-1000 μg/ml of class I-restricted peptide of interest overnight at 37° C. for in vitro peptide exchange. Soluble monomeric class $I^{Q115E}$-$K^b$ loaded with the peptide was dimerized using an anti-His mAb (clone AD1.1.10; Abcam) conjugated to a fluorochrome such as phycoerythrin (PE) at a 2:1 molar ratio for 2 hours at room temperature or overnight at 4° C. The concentration of functional soluble HLA class $I^{Q115E}$-$K^b$ molecules was measured by specific ELISA using an anti-pan class I mAb (clone W6/32, in-house) and an anti-His tag biotinylated mAb (clone AD1.1.10, R&D systems) as capture and detection Abs, respectively.

pHLA Multimer Staining

T cells ($1 \times 10^5$) were incubated for 30 minutes at 37° C. in the presence of 50 nM dasatinib (LC laboratories). The cells were then washed and incubated with 5-10 μg/ml of multimer for 30 minutes at room temperature, and R-phycoerythrin-conjugated AffiniPure Fab fragment goat anti-mouse IgG1 (Jackson ImmunoResearch Laboratories) was added for 15 minutes at 4° C. Next, the cells were washed three times and costained with an anti-CD8 mAb for 15 minutes at 4° C. Dead cells were finally discriminated using the LIVE/DEAD Fixable Dead Cell Stain kit.

Statistical Analysis

Statistical analysis was performed using GraphPad Prism 5.0e. To determine whether two groups were significantly different for a given variable, we conducted an analysis using Welch's t test (two-sided). P values<0.05 were considered significant.

The invention claimed is:

1. A nucleic acid molecule comprising (i) a first nucleotide sequence encoding a recombinant T cell receptor (TCR) or an antigen binding portion thereof that specifically binds human NY-ESO-1 ("anti-NY-ESO-1 TCR"); and (ii) a second nucleotide sequence, wherein the second nucleotide sequence or the polypeptide encoded by the second nucleotide sequence inhibits the expression of an endogenous TCR, wherein the anti-NY-ESO-TCR comprises an alpha chain and a beta chain, wherein the alpha chain comprises a variable region comprising an alpha chain CDR1, an alpha chain CDR2, and an alpha chain CDR3; and wherein the beta chain comprises a variable domain comprising a beta chain CDR1, a beta chain CDR2, and a beta chain CDR3; and wherein:

(i) the beta chain CDR3 of the anti-NY-ESO-TCR comprises the amino acid sequence set forth in SEQ ID NO: 10;

(ii) the beta chain CDR2 of the anti-NY-ESO-TCR comprises the amino acid sequence set forth in SEQ ID NO: 9;

(iii) the beta chain CDR1 of the anti-NY-ESO-TCR comprises the amino acid sequence set forth in SEQ ID NO: 6;

(iv) the alpha chain CDR3 of the anti-NY-ESO-TCR comprises the amino acid sequence set forth in SEQ ID NO: 7;

(v) the alpha chain CDR2 of the anti-NY-ESO-TCR comprises the amino acid sequence set forth in SEQ ID NO: 8; and (vi) the alpha chain CDR1 of the anti-NY-ESO-TCR comprises the amino acid sequence set forth in SEQ ID NO: 5.

2. The nucleic acid molecule of claim 1, wherein the anti-NY-ESO-1 TCR binds to an epitope of NY-ESO-1 consisting of the amino acid sequence set forth in SEQ ID NO: 13.

3. The nucleic acid molecule of claim 2, wherein the epitope is complexed with an HLA class I molecule comprising an HLA-A, HLA-B, HLA-C, HLA-E, HLA-F, or HLA-G allele.

4. The nucleic acid molecule of claim 3, wherein the HLA class I molecule is an HLA-B*40 allele.

5. The nucleic acid molecule of claim 1, wherein (i) the alpha chain variable domain of the anti-NY-ESO-1 TCR comprises the amino acid sequence of a variable domain present in the amino acid sequence set forth in SEQ ID NO: 1;

(ii) the beta chain variable domain of the anti-NY-ESO-1 TCR comprises the amino acid sequence of a variable domain present in the amino acid sequence set forth in SEQ ID NO: 2; or (iii) both (i) and (ii).

6. The nucleic acid molecule of claim 1, wherein:

(a) the alpha chain of the anti-NY-ESO-1 TCR further comprises an alpha chain constant region, wherein the alpha chain constant region is different from a constant region of an endogenous alpha chain, and wherein (i) the alpha chain constant region comprises an amino acid sequence having at least about 85% sequence identity to a constant region present in the amino acid sequence set forth in SEQ ID NO: 1; or (ii) the alpha chain constant region comprises an amino acid sequence comprising at least 1 amino acid substitution relative to a constant region present in the amino acid sequence set forth in SEQ ID NO: 1;

(b) the beta chain of the anti-NY-ESO-1 TCR further comprises a beta chain constant region, wherein the beta chain constant region is different from a constant region of an endogenous beta chain, and wherein (i) the beta chain constant region comprises an amino acid sequence having at least about 85% sequence identity to a constant region present in the amino acid sequence set forth in SEQ ID NO: 2; or (ii) the beta chain constant region comprises an amino acid sequence comprising at least 1 amino acid substitution relative to a constant region present in the amino acid sequence set forth in SEQ ID NO: 2; or (c) both (a) and (b).

7. The nucleic acid molecule of claim 1, wherein (i) the alpha chain of the anti-NY-ESO-1 TCR comprises the amino acid sequence set forth in SEQ ID NO: 1;

(ii) the beta chain of the anti-NY-ESO-1 TCR comprises the amino acid sequence set forth in SEQ ID NO: 2; or (iii) both (i) and (ii).

8. The nucleic acid molecule of claim 1, wherein the second nucleotide sequence (i) is one or more siRNAs that reduce the expression of endogenous TCRs, wherein the one or more siRNAs are complementary to a target sequence within a nucleotide sequence encoding a constant region of the endogenous TCRs;

(ii) encodes Cas9; or (iii) both (i) and (ii).

9. The nucleic acid molecule of claim 1, wherein the anti-NY-ESO-1 TCR comprises an alpha chain constant region, a beta chain constant region, or both; and wherein the alpha chain constant region, the beta chain constant region, or both comprises an amino acid sequence having at least 1 substitution within the target sequence relative to the corresponding amino acid sequence of an endogenous TCR.

10. A vector comprising the nucleic acid molecule of claim 1.

11. A T cell receptor (TCR) or an antigen binding portion thereof comprising the alpha chain variable domain and the beta chain variable domain of the anti-NY-ESO-1 TCR of claim 1.

12. A bispecific TCR comprising a first antigen-binding domain and a second antigen-binding domain, wherein the first antigen-binding domain comprises the TCR or an antigen binding portion thereof of claim 11.

13. A cell comprising the nucleic acid molecule of claim 1.

14. A method of treating a cancer in a subject in need thereof, comprising administering to the subject a cell comprising a vector which comprises a nucleotide sequence encoding a recombinant TCR or an antigen binding portion thereof that specifically binds human NY-ESO-1 ("anti-NY-ESO-1 TCR");

wherein the anti-NY-ESO-TCR comprises an alpha chain and a beta chain, wherein the alpha chain comprises a variable region comprising an alpha chain CDR1, an alpha chain CDR2, and an alpha chain CDR3;

wherein the beta chain comprises a variable domain comprising a beta chain CDR1, a beta chain CDR2, and a beta chain CDR3;

wherein:

(i) the beta chain CDR3 of the anti-NY-ESO-TCR comprises the amino acid sequence set forth in SEQ ID NO: 10;

(ii) the beta chain CDR2 of the anti-NY-ESO-TCR comprises the amino acid sequence set forth in SEQ ID NO: 9;

(iii) the beta chain CDR1 of the anti-NY-ESO-TCR comprises the amino acid sequence set forth in SEQ ID NO: 6;

(iv) the alpha chain CDR3 of the anti-NY-ESO-TCR comprises the amino acid sequence set forth in SEQ ID NO: 7;

(v) the alpha chain CDR2 of the anti-NY-ESO-TCR comprises the amino acid sequence set forth in SEQ ID NO: 8; and (vi) the alpha chain CDR1 of the anti-NY-ESO-TCR comprises the amino acid sequence set forth in SEQ ID NO: 5; and wherein the cancer expresses NY-ESO-1.

15. A method of engineering an antigen-targeting cell, comprising transducing a cell collected from a subject in need of a T cell therapy with a vector comprising a nucleotide sequence encoding a recombinant TCR or an antigen binding portion thereof that specifically binds human NY-ESO-1 ("anti-NY-ESO-1 TCR");

wherein the anti-NY-ESO-TCR comprises an alpha chain and a beta chain, wherein the alpha chain comprises a variable region comprising an alpha chain CDR1, an alpha chain CDR2, and an alpha chain CDR3;

wherein the beta chain comprises variable domain comprising a beta chain CDR1, a beta chain CDR2, and a beta chain CDR3;

wherein:

(i) the beta chain CDR3 of the anti-NY-ESO-TCR comprises the amino acid sequence set forth in SEQ ID NO: 10;

(ii) the beta chain CDR2 of the anti-NY-ESO-TCR comprises the amino acid sequence set forth in SEQ ID NO: 9;

(iii) the beta chain CDR1 of the anti-NY-ESO-TCR comprises the amino acid sequence set forth in SEQ ID NO: 6;

(iv) the alpha chain CDR3 of the anti-NY-ESO-TCR comprises the amino acid sequence set forth in SEQ ID NO: 7;

(v) the alpha chain CDR2 of the anti-NY-ESO-TCR comprises the amino acid sequence set forth in SEQ ID NO: 8; and (vi) the alpha chain CDR1 of the anti-NY-ESO-TCR comprises the amino acid sequence set forth in SEQ ID NO: 5.

16. The nucleic acid molecule of claim 3, wherein the HLA-class I molecule comprises an HLA-B*40:01 allele, an HLA-B*40:02 allele, an HLA-B*40:03 allele, an HLA-B*40:04 allele, an HLA-B*40:05 allele, or an HLA-B*40:06 allele.

17. The method of claim 14, wherein the cancer comprises melanoma, breast cancer, lung cancer, cancer of the head or neck, ovarian cancer, cancer of the esophagus, sarcoma of soft tissue, cancer of the bladder, or squamous cell cancer.

18. The method of claim 17, wherein the cancer comprises melanoma.

19. The method of claim 14, wherein the cancer is relapsed or refractory.

20. The method of claim 14, wherein the cancer is advanced or metastatic.

\* \* \* \* \*

SEQUENCE LISTING

<160> NUMBER OF SEQ ID NOS: 63

<210> SEQ ID NO 1
<211> LENGTH: 272
<212> TYPE: PRT
<213> ORGANISM: Artificial sequence
<220> FEATURE:
<223> OTHER INFORMATION: alpha chain amino acid sequence

<400> SEQUENCE: 1

Met Glu Thr Leu Leu Gly Val Ser Leu Val Ile Leu Trp Leu Gln Leu
1               5                   10                  15

```
Ala Arg Val Asn Ser Gln Gln Gly Glu Glu Asp Pro Gln Ala Leu Ser
            20              25              30

Ile Gln Glu Gly Glu Asn Ala Thr Met Asn Cys Ser Tyr Lys Thr Ser
        35              40              45

Ile Asn Asn Leu Gln Trp Tyr Arg Gln Asn Ser Gly Arg Gly Leu Val
    50              55              60

His Leu Ile Leu Ile Arg Ser Asn Glu Arg Glu Lys His Ser Gly Arg
65              70              75              80

Leu Arg Val Thr Leu Asp Thr Ser Lys Lys Ser Ser Ser Leu Leu Ile
            85              90              95

Thr Ala Ser Arg Ala Ala Asp Thr Ala Ser Tyr Phe Cys Ala Thr Asp
            100             105             110

Arg Gly Thr Asp Lys Leu Ile Phe Gly Thr Gly Thr Arg Leu Gln Val
            115             120             125

Phe Pro Asn Ile Gln Asn Pro Asp Pro Ala Val Tyr Gln Leu Arg Asp
    130             135             140

Ser Lys Ser Ser Asp Lys Ser Val Cys Leu Phe Thr Asp Phe Asp Ser
145             150             155             160

Gln Thr Asn Val Ser Gln Ser Lys Asp Ser Asp Val Tyr Ile Thr Asp
            165             170             175

Lys Thr Val Leu Asp Met Arg Ser Met Asp Phe Lys Ser Asn Ser Ala
            180             185             190

Val Ala Trp Ser Asn Lys Ser Asp Phe Ala Cys Ala Asn Ala Phe Asn
            195             200             205

Asn Ser Ile Ile Pro Glu Asp Thr Phe Phe Pro Ser Pro Glu Ser Ser
    210             215             220

Cys Asp Val Lys Leu Val Glu Lys Ser Phe Glu Thr Asp Thr Asn Leu
225             230             235             240

Asn Phe Gln Asn Leu Ser Val Ile Gly Phe Arg Ile Leu Leu Leu Lys
            245             250             255

Val Ala Gly Phe Asn Leu Leu Met Thr Leu Arg Leu Trp Ser Ser Glx
            260             265             270
```

<210> SEQ ID NO 2
<211> LENGTH: 306
<212> TYPE: PRT
<213> ORGANISM: Artificial sequence
<220> FEATURE:
<223> OTHER INFORMATION: beta chain amino acid sequence

<400> SEQUENCE: 2

```
Met Ser Leu Gly Leu Leu Cys Cys Ala Ala Phe Ser Leu Leu Trp Ala
1               5               10              15

Gly Pro Val Asn Ala Gly Val Thr Gln Thr Pro Lys Phe Arg Val Leu
            20              25              30

Lys Thr Gly Gln Ser Met Thr Leu Leu Cys Ala Gln Asp Met Asn His
        35              40              45

Glu Tyr Met Tyr Trp Tyr Arg Gln Asp Pro Gly Met Gly Leu Arg Leu
    50              55              60

Ile His Tyr Ser Val Gly Glu Gly Thr Thr Ala Lys Gly Glu Val Pro
65              70              75              80

Asp Gly Tyr Asn Val Ser Arg Leu Lys Lys Gln Asn Phe Leu Leu Gly
            85              90              95

Leu Glu Ser Ala Ala Pro Ser Gln Thr Ser Val Tyr Phe Cys Ala Ser
            100             105             110
```

-continued

```
Ser Pro Gly Val Gly Thr Glu Ala Phe Phe Gly Gln Gly Thr Arg Leu
        115                 120                 125

Thr Val Val Glu Asp Leu Asn Lys Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Phe Pro Asp His Val Glu Leu Ser Trp
                165                 170                 175

Trp Val Asn Gly Lys Glu Val His Ser Gly Val Ser Thr Asp Pro Gln
                180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Val Ser Tyr Gln Gln Gly
                260                 265                 270

Val Leu Ser Ala Thr Ile Leu Tyr Glu Ile Leu Leu Gly Arg Pro Pro
        275                 280                 285

Cys Met Leu Cys Trp Ser Ala Pro Cys Val Asp Gly His Gly Gln Glu
        290                 295                 300

Lys Glx
305
```

```
<210> SEQ ID NO 3

<400> SEQUENCE: 3

000

<210> SEQ ID NO 4

<400> SEQUENCE: 4

000

<210> SEQ ID NO 5
<211> LENGTH: 5
<212> TYPE: PRT
<213> ORGANISM: Artificial sequence
<220> FEATURE:
<223> OTHER INFORMATION: alpha CDR1

<400> SEQUENCE: 5

Thr Ser Ile Asn Asn
1               5

<210> SEQ ID NO 6
<211> LENGTH: 5
<212> TYPE: PRT
<213> ORGANISM: Artificial sequence
<220> FEATURE:
<223> OTHER INFORMATION: alpha CDR2

<400> SEQUENCE: 6

Met Asn His Glu Tyr
1               5
```

-continued

```
<210> SEQ ID NO 7
<211> LENGTH: 12
<212> TYPE: PRT
<213> ORGANISM: Artificial sequence
<220> FEATURE:
<223> OTHER INFORMATION: alpha CDR3

<400> SEQUENCE: 7

Cys Ala Thr Asp Arg Gly Thr Asp Lys Leu Ile Phe
1               5                   10

<210> SEQ ID NO 8
<211> LENGTH: 7
<212> TYPE: PRT
<213> ORGANISM: Artificial sequence
<220> FEATURE:
<223> OTHER INFORMATION: beta CDR1

<400> SEQUENCE: 8

Ile Arg Ser Asn Glu Arg Glu
1               5

<210> SEQ ID NO 9
<211> LENGTH: 6
<212> TYPE: PRT
<213> ORGANISM: Artificial sequence
<220> FEATURE:
<223> OTHER INFORMATION: beta CDR2

<400> SEQUENCE: 9

Ser Val Gly Glu Gly Thr
1               5

<210> SEQ ID NO 10
<211> LENGTH: 13
<212> TYPE: PRT
<213> ORGANISM: Artificial sequence
<220> FEATURE:
<223> OTHER INFORMATION: beta CDR3

<400> SEQUENCE: 10

Cys Ala Ser Ser Pro Gly Val Gly Thr Glu Ala Phe Phe
1               5                   10

<210> SEQ ID NO 11

<400> SEQUENCE: 11

000

<210> SEQ ID NO 12

<400> SEQUENCE: 12

000

<210> SEQ ID NO 13
<211> LENGTH: 9
<212> TYPE: PRT
<213> ORGANISM: Artificial sequence
<220> FEATURE:
<223> OTHER INFORMATION: epitope

<400> SEQUENCE: 13

Glu Phe Thr Val Ser Gly Asn Ile Leu
1               5
```

<210> SEQ ID NO 14

<400> SEQUENCE: 14

000

<210> SEQ ID NO 15

<400> SEQUENCE: 15

000

<210> SEQ ID NO 16
<211> LENGTH: 119
<212> TYPE: PRT
<213> ORGANISM: Artificial sequence
<220> FEATURE:
<223> OTHER INFORMATION: B2m amino acid sequence

<400> SEQUENCE: 16

```
Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115
```

<210> SEQ ID NO 17
<211> LENGTH: 816
<212> TYPE: DNA
<213> ORGANISM: Artificial sequence
<220> FEATURE:
<223> OTHER INFORMATION: alpha chain nucleotide sequence

<400> SEQUENCE: 17

```
atggaaactc tcctgggagt gtctttggtg attctatggc ttcaactggc tagggtgaac      60
agtcaacagg gagaagagga tcctcaggcc ttgagcatcc aggagggtga aaatgccacc     120
atgaactgca gttacaaaac tagtataaac aatttacagt ggtatagaca aaattcaggt     180
agaggccttg tccacctaat tttaatacgt tcaaatgaaa gagagaaaca cagtggaaga     240
ttaagagtca cgcttgacac ttccaagaaa agcagttcct tgttgatcac ggcttcccgg     300
gcagcagaca ctgcttctta cttctgtgct acggaccggg gcaccgacaa gctcatcttt     360
gggactggga ccagattaca agtctttcca aatatccaga ccctgacccc tgccgtgtac     420
cagctgagag actctaaatc cagtgacaag tctgtctgcc tattcaccga ttttgattct     480
caaacaaatg tgtcacaaag taaggattct gatgtgtata tcacagacaa aactgtgcta     540
gacatgaggt ctatggactt caagagcaac agtgctgtgg cctggagcaa caaatctgac     600
```

-continued

```
tttgcatgtg caaacgcctt caacaacagc attattccag aagacacctt cttccccagc    660
ccagaaagtt cctgtgatgt caagctggtc gagaaaagct ttgaaacaga tacgaaccta    720
aactttcaaa acctgtcagt gattgggttc cgaatcctcc tcctgaaagt ggccgggttt    780
aatctgctca tgacgctgcg gctgtggtcc agctga                             816
```

<210> SEQ ID NO 18
<211> LENGTH: 918
<212> TYPE: DNA
<213> ORGANISM: Artificial sequence
<220> FEATURE:
<223> OTHER INFORMATION: beta chain nucleotide sequence

<400> SEQUENCE: 18

```
atgagcctcg ggctcctgtg ctgtgcagcc ttttctctcc tgtgggcagg tccagtgaat     60
gctggtgtca ctcagacccc aaaattccgg gtcctgaaga caggacagag catgacactg    120
ctgtgtgccc aggatatgaa ccatgaatac atgtactggt atcgacaaga cccaggcatg    180
gggctgaggc tgattcatta ctcagttggt gagggtacaa ctgccaaagg agaggtccct    240
gatggctaca atgtctccag attaaaaaaa cagaatttcc tgctggggtt ggagtcggct    300
gctccctccc aaacatctgt gtacttctgt gccagcagtc ccggggtggg cactgaagct    360
ttctttggac aaggcaccag actcacagtt gtagaggacc tgaacaaggt gttcccaccc    420
gaggtcgctg tgtttgagcc atcagaagca gagatctccc acacccaaaa ggccacactg    480
gtgtgcctgg ccacaggctt cttccctgac cacgtggagc tgagctggtg ggtgaatggg    540
aaggaggtgc acagtggggt cagcacggac ccgcagcccc tcaaggagca gcccgccctc    600
aatgactcca gatactgcct gagcagccgc ctgagggtct cggccacctt ctggcagaac    660
ccccgcaacc acttccgctg tcaagtccag ttctacgggc tctcggagaa tgacgagtgg    720
acccaggata gggccaaacc cgtcacccag atcgtcagcg ccgaggcctg gggtagagca    780
gactgtggct ttacctcggt gtcctaccag caagggtcc tgtctgccac catcctctat     840
gagatcctgc taggaaggcc accctgtatg ctgtgctggt cagcgccttg tgttgatggc    900
catggtcaag agaaatga                                                 918
```

<210> SEQ ID NO 19
<211> LENGTH: 20
<212> TYPE: PRT
<213> ORGANISM: Artificial sequence
<220> FEATURE:
<223> OTHER INFORMATION: Synthetic Peptide Fragments

<400> SEQUENCE: 19

```
Met Gln Ala Glu Gly Arg Gly Thr Gly Gly Ser Thr Gly Asp Ala Asp
1               5                   10                  15

Gly Pro Gly Gly
            20
```

<210> SEQ ID NO 20
<211> LENGTH: 20
<212> TYPE: PRT
<213> ORGANISM: Artificial sequence
<220> FEATURE:
<223> OTHER INFORMATION: Synthetic Peptide Fragments

<400> SEQUENCE: 20

```
Arg Gly Thr Gly Gly Ser Thr Gly Asp Ala Asp Gly Pro Gly Gly Pro
1               5                   10                  15
```

-continued

```
Gly Ile Pro Asp
            20

<210> SEQ ID NO 21
<211> LENGTH: 20
<212> TYPE: PRT
<213> ORGANISM: Artificial sequence
<220> FEATURE:
<223> OTHER INFORMATION: Synthetic Peptide Fragments

<400> SEQUENCE: 21

Ser Thr Gly Asp Ala Asp Gly Pro Gly Gly Pro Gly Ile Pro Asp Gly
1               5                   10                  15

Pro Gly Gly Asn
            20

<210> SEQ ID NO 22
<211> LENGTH: 20
<212> TYPE: PRT
<213> ORGANISM: Artificial sequence
<220> FEATURE:
<223> OTHER INFORMATION: Synthetic Peptide Fragments

<400> SEQUENCE: 22

Asp Gly Pro Gly Gly Pro Gly Ile Pro Asp Gly Pro Gly Gly Asn Ala
1               5                   10                  15

Gly Gly Pro Gly
            20

<210> SEQ ID NO 23
<211> LENGTH: 20
<212> TYPE: PRT
<213> ORGANISM: Artificial sequence
<220> FEATURE:
<223> OTHER INFORMATION: Synthetic Peptide Fragments

<400> SEQUENCE: 23

Pro Gly Ile Pro Asp Gly Pro Gly Gly Asn Ala Gly Gly Pro Gly Glu
1               5                   10                  15

Ala Gly Ala Thr
            20

<210> SEQ ID NO 24
<211> LENGTH: 20
<212> TYPE: PRT
<213> ORGANISM: Artificial sequence
<220> FEATURE:
<223> OTHER INFORMATION: Synthetic Peptide Fragments

<400> SEQUENCE: 24

Gly Pro Gly Gly Asn Ala Gly Gly Pro Gly Glu Ala Gly Ala Thr Gly
1               5                   10                  15

Gly Arg Gly Pro
            20

<210> SEQ ID NO 25
<211> LENGTH: 20
<212> TYPE: PRT
<213> ORGANISM: Artificial sequence
<220> FEATURE:
<223> OTHER INFORMATION: Synthetic Peptide Fragments

<400> SEQUENCE: 25

Ala Gly Gly Pro Gly Glu Ala Gly Ala Thr Gly Gly Arg Gly Pro Arg
1               5                   10                  15
```

-continued

```
Gly Ala Gly Ala
            20

<210> SEQ ID NO 26
<211> LENGTH: 20
<212> TYPE: PRT
<213> ORGANISM: Artificial sequence
<220> FEATURE:
<223> OTHER INFORMATION: Synthetic Peptide Fragments

<400> SEQUENCE: 26

Glu Ala Gly Ala Thr Gly Gly Arg Gly Pro Arg Gly Ala Gly Ala Ala
1               5                   10                  15

Arg Ala Ser Gly
            20

<210> SEQ ID NO 27
<211> LENGTH: 20
<212> TYPE: PRT
<213> ORGANISM: Artificial sequence
<220> FEATURE:
<223> OTHER INFORMATION: Synthetic Peptide Fragments

<400> SEQUENCE: 27

Gly Gly Arg Gly Pro Arg Gly Ala Gly Ala Ala Arg Ala Ser Gly Pro
1               5                   10                  15

Gly Gly Gly Ala
            20

<210> SEQ ID NO 28
<211> LENGTH: 20
<212> TYPE: PRT
<213> ORGANISM: Artificial sequence
<220> FEATURE:
<223> OTHER INFORMATION: Synthetic Peptide Fragments

<400> SEQUENCE: 28

Arg Gly Ala Gly Ala Ala Arg Ala Ser Gly Pro Gly Gly Gly Ala Pro
1               5                   10                  15

Arg Gly Pro His
            20

<210> SEQ ID NO 29
<211> LENGTH: 20
<212> TYPE: PRT
<213> ORGANISM: Artificial sequence
<220> FEATURE:
<223> OTHER INFORMATION: Synthetic Peptide Fragments

<400> SEQUENCE: 29

Ala Arg Ala Ser Gly Pro Gly Gly Gly Ala Pro Arg Gly Pro His Gly
1               5                   10                  15

Gly Ala Ala Ser
            20

<210> SEQ ID NO 30
<211> LENGTH: 20
<212> TYPE: PRT
<213> ORGANISM: Artificial sequence
<220> FEATURE:
<223> OTHER INFORMATION: Synthetic Peptide Fragments

<400> SEQUENCE: 30

Pro Gly Gly Gly Ala Pro Arg Gly Pro His Gly Gly Ala Ala Ser Gly
```

-continued

```
1               5               10              15

Leu Asn Gly Cys
            20

<210> SEQ ID NO 31
<211> LENGTH: 20
<212> TYPE: PRT
<213> ORGANISM: Artificial sequence
<220> FEATURE:
<223> OTHER INFORMATION: Synthetic Peptide Fragments

<400> SEQUENCE: 31

Pro Arg Gly Pro His Gly Gly Ala Ala Ser Gly Leu Asn Gly Cys Cys
1               5               10              15

Arg Cys Gly Ala
            20

<210> SEQ ID NO 32
<211> LENGTH: 20
<212> TYPE: PRT
<213> ORGANISM: Artificial sequence
<220> FEATURE:
<223> OTHER INFORMATION: Synthetic Peptide Fragments

<400> SEQUENCE: 32

Gly Gly Ala Ala Ser Gly Leu Asn Gly Cys Cys Arg Cys Gly Ala Arg
1               5               10              15

Gly Pro Glu Ser
            20

<210> SEQ ID NO 33
<211> LENGTH: 20
<212> TYPE: PRT
<213> ORGANISM: Artificial sequence
<220> FEATURE:
<223> OTHER INFORMATION: Synthetic Peptide Fragments

<400> SEQUENCE: 33

Gly Leu Asn Gly Cys Cys Arg Cys Gly Ala Arg Gly Pro Glu Ser Arg
1               5               10              15

Leu Leu Glu Phe
            20

<210> SEQ ID NO 34
<211> LENGTH: 20
<212> TYPE: PRT
<213> ORGANISM: Artificial sequence
<220> FEATURE:
<223> OTHER INFORMATION: Synthetic Peptide Fragments

<400> SEQUENCE: 34

Cys Arg Cys Gly Ala Arg Gly Pro Glu Ser Arg Leu Leu Glu Phe Tyr
1               5               10              15

Leu Ala Met Pro
            20

<210> SEQ ID NO 35
<211> LENGTH: 20
<212> TYPE: PRT
<213> ORGANISM: Artificial sequence
<220> FEATURE:
<223> OTHER INFORMATION: Synthetic Peptide Fragments

<400> SEQUENCE: 35
```

```
Arg Gly Pro Glu Ser Arg Leu Leu Glu Phe Tyr Leu Ala Met Pro Phe
1               5                   10                  15

Ala Thr Pro Met
            20

<210> SEQ ID NO 36
<211> LENGTH: 20
<212> TYPE: PRT
<213> ORGANISM: Artificial sequence
<220> FEATURE:
<223> OTHER INFORMATION: Synthetic Peptide Fragments

<400> SEQUENCE: 36

Arg Leu Leu Glu Phe Tyr Leu Ala Met Pro Phe Ala Thr Pro Met Glu
1               5                   10                  15

Ala Glu Leu Ala
            20

<210> SEQ ID NO 37
<211> LENGTH: 20
<212> TYPE: PRT
<213> ORGANISM: Artificial sequence
<220> FEATURE:
<223> OTHER INFORMATION: Synthetic Peptide Fragments

<400> SEQUENCE: 37

Tyr Leu Ala Met Pro Phe Ala Thr Pro Met Glu Ala Glu Leu Ala Arg
1               5                   10                  15

Arg Ser Leu Ala
            20

<210> SEQ ID NO 38
<211> LENGTH: 20
<212> TYPE: PRT
<213> ORGANISM: Artificial sequence
<220> FEATURE:
<223> OTHER INFORMATION: Synthetic Peptide Fragments

<400> SEQUENCE: 38

Phe Ala Thr Pro Met Glu Ala Glu Leu Ala Arg Arg Ser Leu Ala Gln
1               5                   10                  15

Asp Ala Pro Pro
            20

<210> SEQ ID NO 39
<211> LENGTH: 20
<212> TYPE: PRT
<213> ORGANISM: Artificial sequence
<220> FEATURE:
<223> OTHER INFORMATION: Synthetic Peptide Fragments

<400> SEQUENCE: 39

Glu Ala Glu Leu Ala Arg Arg Ser Leu Ala Gln Asp Ala Pro Pro Leu
1               5                   10                  15

Pro Val Pro Gly
            20

<210> SEQ ID NO 40
<211> LENGTH: 20
<212> TYPE: PRT
<213> ORGANISM: Artificial sequence
<220> FEATURE:
<223> OTHER INFORMATION: Synthetic Peptide Fragments

<400> SEQUENCE: 40
```

___

Arg Arg Ser Leu Ala Gln Asp Ala Pro Pro Leu Pro Val Pro Gly Val
1               5                   10                  15

Leu Leu Lys Glu
            20

<210> SEQ ID NO 41
<211> LENGTH: 20
<212> TYPE: PRT
<213> ORGANISM: Artificial sequence
<220> FEATURE:
<223> OTHER INFORMATION: Synthetic Peptide Fragments

<400> SEQUENCE: 41

Gln Asp Ala Pro Pro Leu Pro Val Pro Gly Val Leu Leu Lys Glu Phe
1               5                   10                  15

Thr Val Ser Gly
            20

<210> SEQ ID NO 42
<211> LENGTH: 20
<212> TYPE: PRT
<213> ORGANISM: Artificial sequence
<220> FEATURE:
<223> OTHER INFORMATION: Synthetic Peptide Fragments

<400> SEQUENCE: 42

Leu Pro Val Pro Gly Val Leu Leu Lys Glu Phe Thr Val Ser Gly Asn
1               5                   10                  15

Ile Leu Thr Ile
            20

<210> SEQ ID NO 43
<211> LENGTH: 20
<212> TYPE: PRT
<213> ORGANISM: Artificial sequence
<220> FEATURE:
<223> OTHER INFORMATION: Synthetic Peptide Fragments

<400> SEQUENCE: 43

Val Leu Leu Lys Glu Phe Thr Val Ser Gly Asn Ile Leu Thr Ile Arg
1               5                   10                  15

Leu Thr Ala Ala
            20

<210> SEQ ID NO 44
<211> LENGTH: 20
<212> TYPE: PRT
<213> ORGANISM: Artificial sequence
<220> FEATURE:
<223> OTHER INFORMATION: Synthetic Peptide Fragments

<400> SEQUENCE: 44

Phe Thr Val Ser Gly Asn Ile Leu Thr Ile Arg Leu Thr Ala Ala Asp
1               5                   10                  15

His Arg Gln Leu
            20

<210> SEQ ID NO 45
<211> LENGTH: 20
<212> TYPE: PRT
<213> ORGANISM: Artificial sequence
<220> FEATURE:
<223> OTHER INFORMATION: Synthetic Peptide Fragments

```
<400> SEQUENCE: 45

Asn Ile Leu Thr Ile Arg Leu Thr Ala Ala Asp His Arg Gln Leu Gln
1               5                   10                  15

Leu Ser Ile Ser
            20

<210> SEQ ID NO 46
<211> LENGTH: 20
<212> TYPE: PRT
<213> ORGANISM: Artificial sequence
<220> FEATURE:
<223> OTHER INFORMATION: Synthetic Peptide Fragments

<400> SEQUENCE: 46

Arg Leu Thr Ala Ala Asp His Arg Gln Leu Gln Leu Ser Ile Ser Ser
1               5                   10                  15

Cys Leu Gln Gln
            20

<210> SEQ ID NO 47
<211> LENGTH: 20
<212> TYPE: PRT
<213> ORGANISM: Artificial sequence
<220> FEATURE:
<223> OTHER INFORMATION: Synthetic Peptide Fragments

<400> SEQUENCE: 47

Asp His Arg Gln Leu Gln Leu Ser Ile Ser Ser Cys Leu Gln Gln Leu
1               5                   10                  15

Ser Leu Leu Met
            20

<210> SEQ ID NO 48
<211> LENGTH: 20
<212> TYPE: PRT
<213> ORGANISM: Artificial sequence
<220> FEATURE:
<223> OTHER INFORMATION: Synthetic Peptide Fragments

<400> SEQUENCE: 48

Gln Leu Ser Ile Ser Ser Cys Leu Gln Gln Leu Ser Leu Leu Met Trp
1               5                   10                  15

Ile Thr Gln Cys
            20

<210> SEQ ID NO 49
<211> LENGTH: 20
<212> TYPE: PRT
<213> ORGANISM: Artificial sequence
<220> FEATURE:
<223> OTHER INFORMATION: Synthetic Peptide Fragments

<400> SEQUENCE: 49

Ser Cys Leu Gln Gln Leu Ser Leu Leu Met Trp Ile Thr Gln Cys Phe
1               5                   10                  15

Leu Pro Val Phe
            20

<210> SEQ ID NO 50
<211> LENGTH: 20
<212> TYPE: PRT
<213> ORGANISM: Artificial sequence
<220> FEATURE:
<223> OTHER INFORMATION: Synthetic Peptide Fragments
```

<400> SEQUENCE: 50

Leu Ser Leu Leu Met Trp Ile Thr Gln Cys Phe Leu Pro Val Phe Leu
1               5                   10                  15

Ala Gln Pro Pro
            20

<210> SEQ ID NO 51
<211> LENGTH: 20
<212> TYPE: PRT
<213> ORGANISM: Artificial sequence
<220> FEATURE:
<223> OTHER INFORMATION: Synthetic Peptide Fragments

<400> SEQUENCE: 51

Trp Ile Thr Gln Cys Phe Leu Pro Val Phe Leu Ala Gln Pro Pro Ser
1               5                   10                  15

Gly Gln Arg Arg
            20

<210> SEQ ID NO 52
<211> LENGTH: 180
<212> TYPE: PRT
<213> ORGANISM: Artificial sequence
<220> FEATURE:
<223> OTHER INFORMATION: NY-ESO-1 Amino Acid Sequence

<400> SEQUENCE: 52

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Gly Gly Gly Ala Pro Arg Gly Pro
    50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
        115                 120                 125

Ser Gly Asn Ile Leu Thr Ile Arg Leu Thr Ala Ala Asp His Arg Gln
    130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
            180

<210> SEQ ID NO 53
<211> LENGTH: 21
<212> TYPE: DNA
<213> ORGANISM: Artificial sequence
<220> FEATURE:
<223> OTHER INFORMATION: siRNA-TCRa-1

<400> SEQUENCE: 53
guaaggauuc ugauguguat t                                                      21

<210> SEQ ID NO 54
<211> LENGTH: 21
<212> TYPE: DNA
<213> ORGANISM: Artificial sequence
<220> FEATURE:
<223> OTHER INFORMATION: siRNA-TCRa-2

<400> SEQUENCE: 54
uacacaucag aauccuuact t                                                      21

<210> SEQ ID NO 55
<211> LENGTH: 21
<212> TYPE: DNA
<213> ORGANISM: Artificial sequence
<220> FEATURE:
<223> OTHER INFORMATION: siRNA-TCRb-1

<400> SEQUENCE: 55
ccaccauccu cuaugagaut t                                                      21

<210> SEQ ID NO 56
<211> LENGTH: 21
<212> TYPE: DNA
<213> ORGANISM: Artificial sequence
<220> FEATURE:
<223> OTHER INFORMATION: siRNA-TCRb-2

<400> SEQUENCE: 56
aucucauaga ggaugguggt t                                                      21

<210> SEQ ID NO 57
<211> LENGTH: 24
<212> TYPE: DNA
<213> ORGANISM: Artificial sequence
<220> FEATURE:
<223> OTHER INFORMATION: 3' TCR alpha untranslated region primer

<400> SEQUENCE: 57
ggagagttcc ctctgtttgg agag                                                   24

<210> SEQ ID NO 58
<211> LENGTH: 43
<212> TYPE: DNA
<213> ORGANISM: Artificial sequence
<220> FEATURE:
<223> OTHER INFORMATION: modified 5 RACE primer

<400> SEQUENCE: 58
gtgtggtggt acgggaattc aagcagtggt atcaacgcag agt                             43

<210> SEQ ID NO 59
<211> LENGTH: 43
<212> TYPE: DNA
<213> ORGANISM: Artificial sequence
<220> FEATURE:
<223> OTHER INFORMATION: 3' -TCR primer

<400> SEQUENCE: 59
accactgtgc tggcggccgc tcagctggac cacagccgca gcg                             43

<210> SEQ ID NO 60
<211> LENGTH: 56

-continued

```
<212> TYPE: DNA
<213> ORGANISM: Artificial sequence
<220> FEATURE:
<223> OTHER INFORMATION: Beta C region specific reverse primer 3-C
      Beta-1

<400> SEQUENCE: 60
atcgtcgacc actgtgctgg cggccgctcg agttccaggg ctgccttcag aaatcc        56

<210> SEQ ID NO 61
<211> LENGTH: 59
<212> TYPE: DNA
<213> ORGANISM: Artificial sequence
<220> FEATURE:
<223> OTHER INFORMATION: Beta C region specific reverse primer 3-C
      Beta-2

<400> SEQUENCE: 61
gaccactgtg ctggcggccg ctcgagctag cctctggaat cctttctctt gaccattgc        59

<210> SEQ ID NO 62
<211> LENGTH: 9
<212> TYPE: PRT
<213> ORGANISM: Artificial sequence
<220> FEATURE:
<223> OTHER INFORMATION: HIV nef92-100

<400> SEQUENCE: 62

Lys Glu Lys Gly Gly Leu Glu Gly Leu
1               5

<210> SEQ ID NO 63
<211> LENGTH: 15
<212> TYPE: PRT
<213> ORGANISM: Artificial Sequence
<220> FEATURE:
<223> OTHER INFORMATION: Synthetic construct

<400> SEQUENCE: 63

Val Leu Leu Lys Glu Phe Thr Val Ser Gly Asn Ile Leu Thr Ile
1               5                   10                  15
```